US008420077B2

(12) United States Patent
Altman et al.

(10) Patent No.: US 8,420,077 B2
(45) Date of Patent: *Apr. 16, 2013

(54) SILK FIBROIN HYDROGELS AND USES THEREOF

(75) Inventors: Gregory H. Altman, Arlington, MA (US); Rebecca L. Horan, Arlington, MA (US); Adam L. Collette, Westminister, MA (US); Jingsong Chen, Virginia Beach, VA (US)

(73) Assignee: Allergan, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/764,033

(22) Filed: Apr. 20, 2010

(65) Prior Publication Data
US 2011/0014263 A1 Jan. 20, 2011

Related U.S. Application Data

(60) Provisional application No. 61/170,895, filed on Apr. 20, 2009.

(51) Int. Cl.
*A61F 2/10* (2006.01)
*A61K 35/12* (2006.01)
*A61P 43/00* (2006.01)

(52) U.S. Cl.
USPC ........................................ 424/93.7; 424/423

(58) Field of Classification Search ................ 434/423, 434/93.7
See application file for complete search history.

(56) References Cited

U.S. PATENT DOCUMENTS

| | | | |
|---|---|---|---|
| 4,282,954 A | 8/1981 | Hill | |
| 4,605,691 A | 8/1986 | Balazs | |
| 5,120,829 A | 6/1992 | Pierschbacher et al. | |
| 5,245,012 A | 9/1993 | Lombari et al. | |
| 5,587,456 A | 12/1996 | Pierschbacher et al. | |
| 5,591,822 A | 1/1997 | Pierschbacher et al. | |
| 5,716,404 A | 2/1998 | Vacanti | |
| 5,760,176 A | 6/1998 | Pierschbacher et al. | |
| 6,129,761 A | 10/2000 | Hubbell | |
| 6,287,340 B1 | 9/2001 | Altman et al. | |
| 6,620,917 B1 | 9/2003 | Mello et al. | |
| 6,815,427 B2 | 11/2004 | Tsubouchi et al. | |
| 6,902,932 B2 | 6/2005 | Altman et al. | |
| 7,316,822 B2 | 1/2008 | Binette | |
| 7,635,755 B2 | 12/2009 | Kaplan et al. | |
| 7,662,409 B2 | 2/2010 | Masters | |
| 7,674,882 B2 | 3/2010 | Kaplan et al. | |
| 7,727,575 B2 | 6/2010 | Kaplan et al. | |
| 7,875,296 B2 | 1/2011 | Binette | |
| 2002/0025340 A1 | 2/2002 | Dyer | |
| 2002/0156437 A1 | 10/2002 | McDevitt et al. | |
| 2003/0087433 A1 | 5/2003 | Tsubouchi et al. | |
| 2003/0099630 A1 | 5/2003 | DiBenedetto et al. | |
| 2003/0100108 A1 | 5/2003 | Altman et al. | |
| 2003/0165548 A1 | 9/2003 | Tsubouchi et al. | |
| 2003/0183978 A1 | 10/2003 | Asakura | |
| 2004/0005363 A1 | 1/2004 | Tsukada et al. | |
| 2004/0170827 A1 | 9/2004 | Crighton | |
| 2004/0219630 A1 | 11/2004 | Tsubouchi | |
| 2004/0224406 A1 | 11/2004 | Altman et al. | |
| 2004/0266992 A1 | 12/2004 | Migliaresi et al. | |
| 2005/0089552 A1 | 4/2005 | Altman et al. | |
| 2005/0260706 A1 | 11/2005 | Kaplan et al. | |
| 2006/0153815 A1 | 7/2006 | Seyda et al. | |
| 2006/0205927 A1 | 9/2006 | Valluzzi et al. | |
| 2006/0273279 A1 | 12/2006 | Kaplan et al. | |
| 2007/0187862 A1 | 8/2007 | Kaplan et al. | |
| 2008/0038236 A1 | 2/2008 | Gimble et al. | |
| 2008/0075749 A1 | 3/2008 | Dyer | |
| 2008/0085272 A1 | 4/2008 | Kaplan et al. | |
| 2008/0131509 A1 | 6/2008 | Hossainy et al. | |
| 2008/0176960 A1 | 7/2008 | Tsukada et al. | |
| 2008/0293919 A1 | 11/2008 | Kaplan et al. | |
| 2008/0300683 A1 | 12/2008 | Altman et al. | |
| 2009/0004737 A1 | 1/2009 | Borenstein et al. | |
| 2009/0024162 A1 | 1/2009 | Shalaby et al. | |
| 2009/0030454 A1 | 1/2009 | Knight et al. | |
| 2009/0202614 A1 | 8/2009 | Kaplan et al. | |
| 2009/0214649 A1 | 8/2009 | Gazit et al. | |
| 2009/0232963 A1 | 9/2009 | Kaplan et al. | |
| 2010/0028451 A1 | 2/2010 | Kaplan et al. | |
| 2010/0046902 A1 | 2/2010 | Kaplan et al. | |

(Continued)

FOREIGN PATENT DOCUMENTS

JP 02-245189 9/1990
WO WO 03-022909 3/2003

(Continued)

OTHER PUBLICATIONS

Aoki et al. Bio-Medical Materials and Engineering 13(4):309-316; 2003.*
Yoshimura et al. The Breast J 16(2):169-175, 2010.*
Gould and Auchincloss. Immunology Today 20(2):77-82, 1999.*
Azimzadeh et al. Hematology and Cell Therapy 38(4):331-343, 1997.*
Vepari and Kaplan. Prog Polym Sci 32:991-1007, 2007.*
Belousove, Natalya; et al.: "Modulation of Adenovirus Vector Tropism Via Incorporation of Plypeptide Ligands Into the Fiber Protein" Journal of Virology, vol. 76, No. 17, Sep. 2002, pp. 8621-8631.
Etienne, Olivier; et al.: "Soft Tissue Augmentation Using Silk Gels: and in Vitro and in Vivo Study." Journal of Periodontology, vol. 80, No. 11, Nov. 2009, pp. 1852-1858.
Gil, E.; et al.: "Effect of β-Sheet Crystals on the Thermal and Rheological Behavior of Protein-Based Hydrogels Derived from Gelatin and Silk Fibroin" Macromolecular Bioscience 20050812 vol. 5, No. 8, Aug. 12, 2005, pp. 702-709.

(Continued)

Primary Examiner — Marcia S Noble
(74) Attorney, Agent, or Firm — Stephen Donovan; Debra Condino

(57) ABSTRACT

The present specification provides for methods for purifying fibroins, purified fibroins, methods of conjugating biological and synthetic molecules to fibroins, fibroins conjugated to such molecules, methods of making fibroin hydrogels, fibroin hydrogels and fibroin hydrogel formulations useful for a variety of medical uses, including, without limitation uses as bulking agents, tissue space fillers, templates for tissue reconstruction or regeneration, cell culture scaffolds for tissue engineering and for disease models, surface coating to improve medical device function, or drug delivery devices.

4 Claims, 22 Drawing Sheets

U.S. PATENT DOCUMENTS

| | | |
|---|---|---|
| 2010/0055438 A1 | 3/2010 | Kaplan et al. |
| 2010/0063404 A1 | 3/2010 | Kaplan et al. |
| 2010/0065784 A1 | 3/2010 | Kaplan et al. |
| 2010/0070068 A1 | 3/2010 | Kaplan et al. |
| 2010/0096763 A1 | 4/2010 | Kaplan et al. |
| 2010/0120116 A1 | 5/2010 | Kaplan et al. |
| 2010/0143487 A1 | 6/2010 | Masters |
| 2010/0191328 A1 | 7/2010 | Kaplan et al. |
| 2010/0278405 A1 | 7/2010 | Wang et al. |
| 2010/0196447 A1 | 8/2010 | Kaplan et al. |
| 2010/0196478 A1 | 8/2010 | Masters |
| 2010/0203226 A1 | 8/2010 | Kaplan et al. |
| 2010/0209405 A1 | 8/2010 | Altman et al. |
| 2010/0233267 A1* | 9/2010 | Chen et al. .......... 424/488 |
| 2010/0249924 A1 | 9/2010 | Powell et al. |
| 2010/0256756 A1 | 10/2010 | Altman et al. |
| 2011/0008406 A1 | 1/2011 | Altman et al. |
| 2011/0008436 A1 | 1/2011 | Altman et al. |
| 2011/0008437 A1 | 1/2011 | Altman et al. |
| 2011/0009960 A1 | 1/2011 | Altman et al. |
| 2011/0014263 A1 | 1/2011 | Altman et al. |
| 2011/0014287 A1 | 1/2011 | Altman et al. |
| 2011/0020409 A1 | 1/2011 | Altman et al. |
| 2011/0052695 A1 | 3/2011 | Jiang et al. |
| 2011/0070281 A1 | 3/2011 | Altman |
| 2011/0097381 A1 | 4/2011 | Binette |
| 2011/0111031 A1 | 5/2011 | Jiang et al. |
| 2011/0129531 A1 | 6/2011 | Collette et al. |
| 2011/0167602 A1 | 7/2011 | Altman et al. |
| 2011/0171453 A1 | 7/2011 | Altman et al. |
| 2011/0184227 A1 | 7/2011 | Altman et al. |
| 2011/0189292 A1 | 8/2011 | Lebreton et al. |
| 2011/0189773 A1 | 8/2011 | Altman et al. |
| 2011/0224703 A1 | 9/2011 | Mortarino et al. |
| 2011/0257665 A1 | 10/2011 | Mortarino et al. |
| 2011/0257761 A1 | 10/2011 | Mortarino et al. |

FOREIGN PATENT DOCUMENTS

| | | |
|---|---|---|
| WO | WO 03/022909 | 3/2003 |
| WO | WO 2005/123114 | 12/2005 |
| WO | WO 2010/141133 | 12/2010 |

OTHER PUBLICATIONS

Gil, E.; et al.: "Swelling Behavior and Morphological Evolution of Mixed Gelatin/Silk Fibroin Hydrogels" Biomacromolecules Nov./Dec. 2005 American Chemical Society US, vol. 6, No. 6; Nov. 2005, pp. 3079-3087.

Hersel, U.; et al.: "RGD Modified Polymers: Biomatericals for Stimulated Cell Adhesion and Beyond" Biomatericals, Elsevier Science Publishers, vol. 24, No. 24, Nov. 1, 2003, pp. 4385-4415.

Sofia, S.; et al.: "Functionalized Silk-Based Biomaterials for Bone Formation" Journal of Biomedical Materials Research, vol. 54, No. 1, Jan. 1, 2001, pp. 139-148.

Missana, M.C. et al, Autologous fat transfer in reconstructive breast surgery: Indications, technique and results, EJSO the Journal of Cancer Surgery, EJSO 33, 2007, 685-690, Elsevier.

Spear, Scott L, et al, Fat Injection to Correct Contour Deformities in the Reconstructed Breast, Division of Plastic Surgery, Georgetown University Hospital, Vo. 116, No. 5, Jun. 22, 2004, pp. 1300-1305, Presented at the 21st Annual Plastic Surgery Day and Bernard Sarnat Lectureship at Cedars-Sinai Medical Center, Los Angeles, CA, Apr. 24, 2004.

Coleman, Sydney R. et al, Fat Grafting to the Breast Revisited: Safety and Efficacy, From the New York University School of Medicine. Received for publication Feb. 21, 2006; accepted Jul. 18, 2006. Presented at the American Association of Plastic Surgeons meeting in Hilton Head South Carolina on May 9, 2006. 2007, the American Society of Plastic Surgeons, pp. 775-785.

Zocchi, M.L. et al, Biocompartmental Breast Lipostructuring, published online: Jan. 10, 2008, Springer Science and Business Media, LLC 2008, Aesth Plast Surg 2008, 32:313-328.

Ajisawa, Akiyoshi, Dissolution of silk fibroin with calcium chloride/ ethanol aqueous solution, Nippon Sanshigaku Zasshi (1998), 67(2):91-94.

Asakura, et al., NMR imaging of diffusion of small organic molecules in silk fibroin gel. Macromolecules (1991), 24(2):620-2.

Ayub et al., Mechanism of the gelation of fibroin solution, Bioscience, Biotechnology, and Biochemistry (1993), 57(11):1910-12.

Ayub et al., Quantitative structural analysis and physical properties of silk fibroin hydrogels, (1994) 437-501.

Ayub, et al., Effect of pH on silk fibroin gelation, Sen'i Gakkaishi (1992), 48(3):141-4, Koganei, Japan.

Cappello et al., In-situ self-assembling protein polymer gel systems for administration, delivery, and release of drugs, USA Journal of controlled release: official journal of the Controlled Release Society (Apr. 30, 1998), 53(1-3):105-17, San Diego, CA 92121.

Collette et al., Comparative in vivo evaluation of a novel silk hydrogel injectable for drug delivery, Society for Biomaterials (2007), Chicago, IL, abstract#:719; pp. 1-3.

Fang, Characterization and Evalution of Silk Protein Hydrogels for Drug Delivery, Chem Pharm Bulletin (2006), pp. 156-162.

Freddi, Swelling and Dissolution of Silk Fibroin (Bombyx mori) in N-methyl morpholine N-oxide, International Journal of Biological Macromolecules (1999), pp. 251-263.

Gil, Swelling Behavior and Morphological Evolution of Mixed Gelatin/Silk Fibroin Hydrogels, Biomacromolecules (2005), pp. 3079-3087.

Ha, Structural Studies of Bombyx mori Silk Fibroin During Regeneration from Solutions and Wet Fiber Spinning, Biomacromolecules (2005), pp. 1722-1731.

Hanawa, New Oral Dosage Form for Elderly Patients: Preparation and Characterization of Silk Fibroin Gel, Chem Pharm Bulletin (1995), pp. 284-288.

Hofmann, Silk as a Biomaterial for Controlled Drug Delivery, European Cells and Materials (2005), vol. 10, supple 1 pp. 11.

Hofmann, Silk Fibroin as an Organic Polymer for Controlled Drug Delivery, Journal of Controlled Release (2006), 111:219-227.

Horan et al., In vitro degradation of silk fibroin, USA Biomaterials (Jun. 2005), 26(17):3385-93.

Hossain, Dilute-solution Properties of Regenerated Silk Fibroin, Journal of Physical Chemistry (2003), 107:8066-8073.

Hu et al., Studies on the stability of gel and gelation of silk protein fibroin, Zhejiang Sichou Gongxueyuan Xuebao (1999), 16(3):172-176, Peop. Rep. China, considered abstract only.

Jin, Biomaterial Films of Bombyx mori Silk Fibroin with Poly(ethylene oxide), Biomacromolecules (2004), 5:711-717.

Kim et al., Dissolvable films of silk fibroin for ultrathin, conformal bio-integrated electronics (2010), pp. 1-8.

Kim, et al. Structure and Properties of Silk Hydrogels. Biomacromolecules (2004), 5(3):786-792. Departments of Biomedical Engineering, Chemical and Biological Engineering, and Bioengineering Center, Tufts University, Medford, MA, USA.

Kim, et al., Solution behavior of silk fibroin, Polymeric Materials Science and Engineering (2003), 89:490-491, Medford, MA, USA.

Kobayashi, et al., Rheological behavior of silk fibroin aqueous solution: Gel-sol transition and fiber formation, Abstracts of Papers, 222nd ACS National Meeting, Chicago, IL, United States, Aug. 26-30, 2001, POL Y-113, American Chemical Society, Washington, D. C.

Kobayashi, et al., Study of gel-sol transition of silk fibroin, National Institute of Agrobiological Resources, Abstracts of Papers, 221st ACS National Meeting, San Diego, CA, United States, Apr. 1-5, 2001, PMSE-340.

Kobayashi, et al., Study of the gel-sol transition of silk fibroin, Polymeric Materials Science and Engineering (2001), 84 620.

Kratky, et al., Molecular morphology of silk fibroin, Chemie (1956), 87:269-80.

Lee K Y, Hydrogels for tissue engineering, Chemical reviews (2001), 101(7):1869-79.

Magoshi, et al., Gelation and subsequent molecular orientation of silk fibroin, ACS Symposium Series (1992), 489.

Matsumoto et al., Silk Fibroin Solution Properties Related to Assembly and Structure, Macromolecular Journal (2008) 8:1006-1018.

Migliaresi, et al., Physical and biologcal evaluation of silk fibroin gels, Abstracts of Papers, 228th ACS National Meeting, Philadelphia, PA, United States, Aug. 22-26, 2004, POLY-395.

Min et al., Physical and chemical characteristics of crosslinked silk fibroin gel, *Canye Kexue* (1999) 25(2):108-112.

Phillips, Dissolution and Regeneration of *Bombyx mori* Silk Fibroin Using Ionic Liquids, *Journal of the American Chemical Society* (2004), 126:14350-14351.

Servoli, Surface Properties of Silk Fibroin Films and Their Interatcion with Fibroblasts, *Macromolecular Bioscience* (2005), 5:1175-1183.

Sohn, Phase Behavior and Hydration of silk Fibroin, *Biomacromolecules* (2004), 5:751-757.

Sun, et al., Study of preparation, structure and properties of pure silk fibroin gel. (2003), 24(2), 12-14, China.

Tamada, Y., Symposium Preprints, *The Society of Fiber Science and Technology* (1998) p. S-51

Tsukada, Preparation and application of porous silk fibroin materials, *Journal of Applied Polymer Science* (1994), 54:507-514.

Zhu et al., Gelation of silk sericin and physical properties of the gel. *Nippon Sanshigaku Zasshi* (1995), 64(5):415-19.

Altman et al. "Silk-Based Biomaterials," Biomaterials 24(3): 401-416 (2003).

Cao et al. "Biodegradation of silk biomaterials," Int. J. Mol. Sci. 10(4): 1514-1524 (2009).

Cappello et al. "In-Situ Self-Assembling Protein Polymer Gel Systems for Administration, Delivery, and Release of Drugs," J. Control Release, 53(1-3): 105-17 (1998).

Derwent Record, Abstract of JP 08295697 A2, Production of Aqueous Solution of Silk Fibroin at High Concentration, 2006.

Fang et al. "Characterization and evaluation of silk protein hydrogels for drug delivery," Chem. Pharm. Bull. (Tokyo). 54(2): 156-162 (2006).

Hanawa et al. "New Oral Dosage Form for Elderly Patients: Preparation and Characterization of Silk Fibroin Gel," Chem. Pharm. Bull. (Tokyo) 43(2): 284-288 (1995).

T. Hanawa, et al., New Oral Dosage Form for Elderly Patients. II. Release Behavior of Benfotiamine from Silk Fibroin Gel, Chem. Pharm. Bull. (Tokyo) 43(5): 872-876 (1995).

Hanawa et al. "New Oral Dosage Form for Elderly Patients. III. Stability of Trichloromethiazide in Silk Fibroin Gel and Various Sugar Solutions," Drug Dev. Ind. Pharm. 26(10): 1091-1097 (2000).

Kim et al. "Structure and Properties of Silk Hydrogels," Biomacromolecules 5(3): 786-792 (2004).

Numata et al. "Bioengineered Silk Protein-Based Gene Delivery Systems," Biomaterials. 30(29): 5775-5784 (2009).

Van Tomme et al. "In situ gelling hydrogels for pharmaceutical and biomedical applications," Int. J. Pharm. 355(1-2): 1-18 (2008).

Wang et al. "Stem Cell-Based Tissue Engineering with Silk Biomaterials," Biomaterials 27(36): 6064-6082 (2006).

\* cited by examiner

SEQUENCE LISTING

```
<160> NUMBER OF SEQ ID NOS: 29

<210> SEQ ID NO 1
<211> LENGTH: 23
<212> TYPE: PRT
<213> ORGANISM: Artificial Sequence
<220> FEATURE:
<223> OTHER INFORMATION: Chemically synthesized RGD peptide

<400> SEQUENCE: 1

Gly Arg Gly Asp Ile Pro Ala Ser Ser Lys Gly Gly Gly Gly Ser Arg
1               5                   10                  15

Leu Leu Leu Leu Leu Leu Arg
            20
```

```
<210> SEQ ID NO 2
<211> LENGTH: 23
<212> TYPE: PRT
<213> ORGANISM: Artificial Sequence
<220> FEATURE:
<223> OTHER INFORMATION: Chemically synthesized acylated RGD peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (2)..(2)
<223> OTHER INFORMATION: D form
<220> FEATURE:
<221> NAME/KEY: MOD_RES
<222> LOCATION: (16)..(16)
<223> OTHER INFORMATION: D form
<220> FEATURE:
<221> NAME/KEY: MOD_RES
<222> LOCATION: (23)..(23)
<223> OTHER INFORMATION: D form

<400> SEQUENCE: 2

Gly Arg Gly Asp Ile Pro Ala Ser Ser Lys Gly Gly Gly Gly Ser Arg
1               5                   10                  15

Leu Leu Leu Leu Leu Leu Arg
            20

<210> SEQ ID NO 3
<211> LENGTH: 10
<212> TYPE: PRT
<213> ORGANISM: Artificial Sequence
<220> FEATURE:
<223> OTHER INFORMATION: Chemically synthesized spacer peptide
      SGGGGKSSAP

<400> SEQUENCE: 3

Ser Gly Gly Gly Gly Lys Ser Ser Ala Pro
1               5                   10

<210> SEQ ID NO 4
<211> LENGTH: 6
<212> TYPE: PRT
<213> ORGANISM: Artificial Sequence
<220> FEATURE:
<223> OTHER INFORMATION: Chemically synthesized hydrophilic domain

<400> SEQUENCE: 4

Lys Gln Ala Gly Asp Val
1               5

<210> SEQ ID NO 5
<211> LENGTH: 5
<212> TYPE: PRT
<213> ORGANISM: Artificial Sequence
<220> FEATURE:
<223> OTHER INFORMATION: Chemically synthesized hydrophilic domain

<400> SEQUENCE: 5

Pro His Ser Arg Asn
1               5

<210> SEQ ID NO 6
<211> LENGTH: 5
<212> TYPE: PRT
<213> ORGANISM: Artificial Sequence
<220> FEATURE:
<223> OTHER INFORMATION: Chemically synthesized hydrophilic domain YIGSR
```

```
<400> SEQUENCE: 6

Tyr Ile Gly Ser Arg
1               5

<210> SEQ ID NO 7
<211> LENGTH: 9
<212> TYPE: PRT
<213> ORGANISM: Artificial Sequence
<220> FEATURE:
<223> OTHER INFORMATION: Chemically synthesized hydrophilic domain
      CDPGYIGSR

<400> SEQUENCE: 7

Cys Asp Pro Gly Tyr Ile Gly Ser Arg
1               5

<210> SEQ ID NO 8
<211> LENGTH: 5
<212> TYPE: PRT
<213> ORGANISM: Artificial Sequence
<220> FEATURE:
<223> OTHER INFORMATION: Chemically synthesized hydrophilic domain IKVAV

<400> SEQUENCE: 8

Ile Lys Val Ala Val
1               5

<210> SEQ ID NO 9
<211> LENGTH: 10
<212> TYPE: PRT
<213> ORGANISM: Artificial Sequence
<220> FEATURE:
<223> OTHER INFORMATION: Chemically synthesized hydrophilic domain
      RNIAEIIKDI

<400> SEQUENCE: 9

Arg Asn Ile Ala Glu Ile Ile Lys Asp Ile
1               5                   10

<210> SEQ ID NO 10
<211> LENGTH: 7
<212> TYPE: PRT
<213> ORGANISM: Artificial Sequence
<220> FEATURE:
<223> OTHER INFORMATION: Chemically synthesized hydrophilic domain
      YFQRYLI

<400> SEQUENCE: 10

Tyr Phe Gln Arg Tyr Leu Ile
1               5

<210> SEQ ID NO 11
<211> LENGTH: 5
<212> TYPE: PRT
<213> ORGANISM: Artificial Sequence
<220> FEATURE:
<223> OTHER INFORMATION: Chemically synthesized hydrophilic domain PDSGR

<400> SEQUENCE: 11

Pro Asp Ser Gly Arg
1               5

<210> SEQ ID NO 12
<211> LENGTH: 7
<212> TYPE: PRT
<213> ORGANISM: Artificial Sequence
<220> FEATURE:
```

```
<223> OTHER INFORMATION: Chemically synthesized hydrophilic domain
      FHRRIKA

<400> SEQUENCE: 12

Phe His Arg Arg Ile Lys Ala
1               5

<210> SEQ ID NO 13
<211> LENGTH: 6
<212> TYPE: PRT
<213> ORGANISM: Artificial Sequence
<220> FEATURE:
<223> OTHER INFORMATION: Chemically synthesized hydrophilic domain
      PRRARV

<400> SEQUENCE: 13

Pro Arg Arg Ala Arg Val
1               5

<210> SEQ ID NO 14
<211> LENGTH: 8
<212> TYPE: PRT
<213> ORGANISM: Artificial Sequence
<220> FEATURE:
<223> OTHER INFORMATION: Chemically synthesized hydrophilic domain
      WQPPRARI

<400> SEQUENCE: 14

Trp Gln Pro Pro Arg Ala Arg Ile
1               5

<210> SEQ ID NO 15
<211> LENGTH: 5
<212> TYPE: PRT
<213> ORGANISM: Artificial Sequence
<220> FEATURE:
<223> OTHER INFORMATION: Chemically synthesized hydrophobic/apolar tail
      LLLLL

<400> SEQUENCE: 15

Leu Leu Leu Leu Leu
1               5

<210> SEQ ID NO 16
<211> LENGTH: 5
<212> TYPE: PRT
<213> ORGANISM: Artificial Sequence
<220> FEATURE:
<223> OTHER INFORMATION: Chemically synthesized hydrophobic/apolar tail
      LLFFL

<400> SEQUENCE: 16

Leu Leu Phe Phe Leu
1               5

<210> SEQ ID NO 17
<211> LENGTH: 5
<212> TYPE: PRT
<213> ORGANISM: Artificial Sequence
<220> FEATURE:
<223> OTHER INFORMATION: Chemically synthesized hydrophobic/apolar tail
      LFLWL

<400> SEQUENCE: 17

Leu Phe Leu Trp Leu
1               5

<210> SEQ ID NO 18
```

```
<211> LENGTH: 5
<212> TYPE: PRT
<213> ORGANISM: Artificial Sequence
<220> FEATURE:
<223> OTHER INFORMATION: Chemically synthesized hydrophobic/apolar tail
      FLWLL

<400> SEQUENCE: 18

Phe Leu Trp Leu Leu
1               5

<210> SEQ ID NO 19
<211> LENGTH: 5
<212> TYPE: PRT
<213> ORGANISM: Artificial Sequence
<220> FEATURE:
<223> OTHER INFORMATION: Chemically synthesized hydrophobic/apolar tail
      LALGL

<400> SEQUENCE: 19

Leu Ala Leu Gly Leu
1               5

<210> SEQ ID NO 20
<211> LENGTH: 6
<212> TYPE: PRT
<213> ORGANISM: Artificial Sequence
<220> FEATURE:
<223> OTHER INFORMATION: Chemically synthesized hydrophobic/apolar tail
      LLLLLL

<400> SEQUENCE: 20

Leu Leu Leu Leu Leu Leu
1               5

<210> SEQ ID NO 21
<211> LENGTH: 7
<212> TYPE: PRT
<213> ORGANISM: Artificial Sequence
<220> FEATURE:
<223> OTHER INFORMATION: Chemically synthesized hydrophobic/apolar tail
      RLLLLLR

<400> SEQUENCE: 21

Arg Leu Leu Leu Leu Leu Arg
1               5

<210> SEQ ID NO 22
<211> LENGTH: 7
<212> TYPE: PRT
<213> ORGANISM: Artificial Sequence
<220> FEATURE:
<223> OTHER INFORMATION: Chemically synthesized hydrophobic/apolar tail
      KLLLLLR

<400> SEQUENCE: 22

Lys Leu Leu Leu Leu Leu Arg
1               5

<210> SEQ ID NO 23
<211> LENGTH: 7
<212> TYPE: PRT
<213> ORGANISM: Artificial Sequence
<220> FEATURE:
<223> OTHER INFORMATION: Chemically synthesized hydrophobic/apolar tail
      KLLLLLK

<400> SEQUENCE: 23

Lys Leu Leu Leu Leu Leu Lys
```

-continued

<210> SEQ ID NO 24
<211> LENGTH: 14
<212> TYPE: PRT
<213> ORGANISM: Artificial Sequence
<220> FEATURE:
<223> OTHER INFORMATION: Chemically synthesized spacer GSPGISGGGGGILE

<400> SEQUENCE: 24

Gly Ser Pro Gly Ile Ser Gly Gly Gly Gly Ile Leu Glu
1               5                   10

<210> SEQ ID NO 25
<211> LENGTH: 11
<212> TYPE: PRT
<213> ORGANISM: Artificial Sequence
<220> FEATURE:
<223> OTHER INFORMATION: Chemically synthesized spacer SGGGGKSSAPI

<400> SEQUENCE: 25

Ser Gly Gly Gly Gly Lys Ser Ser Ala Pro Ile
1               5                   10

<210> SEQ ID NO 26
<211> LENGTH: 21
<212> TYPE: PRT
<213> ORGANISM: Artificial Sequence
<220> FEATURE:
<223> OTHER INFORMATION: Chemically synthesized spacer-tail peptide
      GSPGISGGGGGILEKLLLLLK

<400> SEQUENCE: 26

Gly Ser Pro Gly Ile Ser Gly Gly Gly Gly Ile Leu Glu Lys Leu
1               5                   10                  15

Leu Leu Leu Leu Lys
            20

<210> SEQ ID NO 27
<211> LENGTH: 22
<212> TYPE: PRT
<213> ORGANISM: Artificial Sequence
<220> FEATURE:
<223> OTHER INFORMATION: Chemically synthesized spacer-tail peptide
      GSPGISGGGGGILEKLALWLLR

<400> SEQUENCE: 27

Gly Ser Pro Gly Ile Ser Gly Gly Gly Gly Ile Leu Glu Lys Leu
1               5                   10                  15

Ala Leu Trp Leu Leu Arg
            20

<210> SEQ ID NO 28
<211> LENGTH: 20
<212> TYPE: PRT
<213> ORGANISM: Artificial Sequence
<220> FEATURE:
<223> OTHER INFORMATION: Chemically synthesized spacer-tail peptide
      GSPGISGGGGGILERLLLLR

<400> SEQUENCE: 28

Gly Ser Pro Gly Ile Ser Gly Gly Gly Gly Ile Leu Glu Arg Leu
1               5                   10                  15

Leu Leu Leu Arg
            20

```
<210> SEQ ID NO 29
<211> LENGTH: 21
<212> TYPE: PRT
<213> ORGANISM: Artificial Sequence
<220> FEATURE:
<223> OTHER INFORMATION: Chemically synthesized spacer-tail peptide
      GSPGISGGGGGILERLLWLLR

<400> SEQUENCE: 29

Gly Ser Pro Gly Ile Ser Gly Gly Gly Gly Ile Leu Glu Arg Leu
1               5                   10                  15

Leu Trp Leu Leu Arg
            20
```

SILK FIBROIN HYDROGELS AND USES THEREOF

CROSS REFERENCE

This patent application claims priority pursuant to 35 U.S.C. §119(e) to U.S. Provisional Patent Application Ser. No. 61/170,895 filed Apr. 20, 2009, which is hereby incorporated by reference in its entirety.

FIELD OF THE INVENTION

The present specification discloses purified silk fibroin and method for purifying silk fibroins, hydrogels comprising silk fibroin with or without an amphiphilic peptide and methods for making hydrogels comprising silk fibroin and the use of silk fibroin hydrogels in a variety of medical uses, including, without limitation fillers for tissue space, templates for tissue reconstruction or regeneration, scaffolds for cells in tissue engineering applications and for disease models, a surface coating to improve medical device function, or as a platform for drug delivery.

BACKGROUND

Silk refers to a filamentous product secreted by an organism such as a spider or silkworm. Fibroin is the primary structural component of silk. It is composed of monomeric units comprising an about 350 kDa heavy chain and an about 25 kDa light chain, and interspersed within the fibroin monomers is another about 25 kDa protein derived from the P25 gene. The ratio of heavy chain:light chain:P25 protein is about 6:6:1. Fibroin is secreted by the silk glands of the organism as a pair of complementary fibrils called "brins". As fibroin brins leave the glands, they are coated with sericin, a glue-like substance which binds the brins together. Sericin is often antigenic and may be associated with an adverse tissue reaction when sericin-containing silk is implanted in vivo.

Silkworm silk fibers traditionally available in the commercial market are often termed "degummed", which refers to the loosening and removal of a portion of the sericin coat surrounding the two fibroin brins through washing or extraction in hot soapy water. This degummed silk often contains or is recoated with sericin and other impurities in order to bind the plied multifilament together into a single fiber. Therefore, degummed silk, unless explicitly stated to the contrary, typically contains twenty percent to twenty-eight percent (by weight) sericin and can not be assumed to be sericin-free.

Silk fibers have historically been valued in surgery for their mechanical properties, particularly in the form of braided filaments used as a suture material. Residual sericin that may be contained in these materials stands as a potential obstacle to its use as a biomaterial as it does present the possibility for a heightened immune response. This sericin contamination may be substantially removed though, resulting in a virtually sericin-free fibroin which may be used either as fibers or dissolved and reconstituted in a number of forms. For example, natural silk from the silkworm Bombyx mori may be subjected to sericin extraction, spun into yarns then used to create a matrix with high tensile strength suitable for applications such as bioengineered ligaments and tendons. Use of regenerated silk materials has also been proposed for a number of medical purposes including wound protection, cell culture substrate, enzyme immobilization, soft contact lenses, and drug-release agents.

Silk fibroin devices whether native, dissolved, or reconstituted, do not typically contain cell-binding domains such as those found in collagen, fibronectin, and many other extra-cellular matrix (ECM) molecules. Fibroin is also strongly hydrophobic due to the β-sheet-rich crystalline network of the core fibroin protein. These two factors couple to severely limit the capacity of native host cells to bind to and interact with implanted silk devices, as neither inflammatory cells like macrophages or reparative cells like fibroblasts are able to attach strongly, infiltrate and bioresorb the silk fibroin devices. In the case of virgin silk and black braided (wax or silicone coated) silk sutures, this is typically manifested in a harsh foreign-body response featuring peripheral encapsulation. Substantially sericin-free silk experiences a similar, though substantially less vigorous response when implanted. In essence, the host cells identify silk as a foreign body and opt to wall it off rather than interact with it. This severely limits the subsequent long-term potential of the device particularly relating to tissue in-growth and remodeling and potentially, the overall utility of the device. If it is possible to provide a more effective biomaterial formulation for mediating host-device interactions whereby cells are provided with a recognizable, acceptable and hence biocompatible surface, the biological, medicinal and surgical utility of silk is dramatically improved.

One possible means of introducing this improved cell-material interaction is to alter the silk fibroin material format into a more biocompatible matrix. Manipulating the silk fibroin to make it into a silk hydrogel formulation is one particularly intriguing option because it consists of a silk protein network which is fully saturated with water, coupling the molecular resiliency of silk with the biocompatibility of a "wet" material. Generation of a silk hydrogel may be accomplished in short by breaking apart native silk fibroin polymers into its individual monomeric components using a solvent species, replacing the solvent with water, then inducing a combination of inter- and intra-molecular aggregation. It has been shown that the sol-gel transition can be selectively initiated by changing the concentration of the protein, temperature, pH and additive (e.g., ions and hygroscopic polymers such as poly(ethylene oxide) (PEO), poloxamer, and glycerol). Increasing the silk concentration and temperature may alter the time taken for silk gelation by increasing the frequency of molecular interactions, increasing the chances of polymer nucleation. Another means of accelerating silk gelation is through use of calcium ions which may interact with the hydrophilic blocks at the ends of silk molecules in solution prior to gelation. Decreasing pH and the addition of a hydrophilic polymer have been shown to enhance gelation, possibly by decreasing repulsion between individual silk molecules in solution and subsequently competing with silk fibroin molecules in solution for bound water, causing fibroin precipitation and aggregation.

Other silk fibroin gels have been produced by, for example, mixing an aqueous silk fibroin solution with protein derived biomaterials such as gelatin or chitosan. Recombinant proteins materials based on silk fibroin's structure have also been used to create self-assembling hydrogel structures. Another silk gel, a silk fibroin-poly-(vinyl alcohol) gel was created by freeze- or air-drying an aqueous solution, then reconstituting in water and allowing to self-assemble. Silk hydrogels have also been generated by either exposing the silk solution to temperature condition of 4° C. (Thermgel) or by adding thirty percent (v/v) glycerol (Glygel). Silk hydrogels created via a freeze-thaw process have not only been generated but also used in vitro as a cell culture scaffold.

The use of silk hydrogels as biomaterial matrices has also been explored in a number of ways. General research on hydrogels as platforms for drug delivery, specifically the release behavior of benfotiamine (a synthetic variant of vitamin $B_1$) coupled to silk hydrogel was investigated. The study revealed both silk concentration and addition of other compounds may factor in to the eventual release profile of the material. Similarly, the release of FITC-labeled dextran from a silk hydrogel could be manipulated by altering the silk concentrations within the gel.

Further studies of silk hydrogels have been performed in vivo as well. For example, the material has been used in vivo to provide scaffolding for repair of broken bones in rabbits and showed an accelerated healing rate relative to control animals. Of particular interest, the in situ study also illustrated that the particular formulation of silk hydrogel did not elicit an extensive immune response from the host.

Despite early promise with silk hydrogel formulations in vivo, sericin contamination remains a concern in their generation and use just as with native fibroin for reasons of biocompatibility as well as the potential for sericin to alter gelation kinetics. The existence of sericin molecules in the silk solution intermediate prior to gelation may also compromise final gel structural quality, i.e., the distribution of β-sheet structure. For these reasons the removal of sericin from silk fibroin material prior to hydrogel manufacture remains a concern. The potential for disruption of gelation kinetics and structure by contaminants also presents the need for development of a process which consistently ensures structural uniformity and biocompatibility.

SUMMARY OF THE INVENTION

The embodiments described herein provide for silk hydrogel formulations that may be useful for a variety of medical uses. More specifically, example embodiments of the present invention provide for gels including silk fibroin and peptides. Other example embodiments provide for the use of organic enhancers which improve device utility and functional peptide enhancers that may improve utility and biocompatibility of silk formulations. Silk hydrogel embodiments may be used as tissue space fillers, templates for tissue reconstruction or regeneration, cell culture scaffolds for tissue engineering and for disease models, surface coating to improve medical device function, or drug delivery devices.

One embodiment provides for an injectable silk gel comprising a gel phase and a carrier phase (which may provide additional lubricity) in which the gel phase comprises water, substantially sericin-depleted silk fibroin and an amphiphilic peptide. In another embodiment, the gel phase is about 1% to 99%, for example the gel phase is about 50% to about 99% of the total formulation volume with the carrier phase providing the remainder. For example, the gel phase is about 75% of the total formulation volume and the carrier phase is the remaining 25%. The gel phase may comprise about 0.5% to about 20% silk fibroin protein by mass, for example about 1% to about 10%, or about 4% to about 6%. In one embodiment, the silk fibroin comprises about 0.5% to about 9.9% of the total formulation mass.

In a particular embodiment, the peptide is an amphiphilic peptide consisting of a tail region, followed by a spacer region and finally the sequence arginine-glycine-aspartic acid, known as the RGD motif. For example, the total peptide is 23 amino acids in length (hereinafter, referred to as "23RGD"). The gel phase may comprise, for example, a molar ratio of about 1:100 moles to about 100:1 moles of this peptide per mole of silk fibroin.

Another example embodiment provides for an injectable gel formulation comprising silk fibroin and an amphiphilic peptide, wherein the formulation comprises from about 1% to about 20%, for example about 4% to about 6% silk fibroin, and the amphiphilic peptide is 23RGD.

Yet another embodiment provides for an injectable gel formulation comprising silk fibroin and 23RGD, wherein the formulation comprises from about 4% to about 6% silk fibroin, and 23RGD concentration is 3:1 moles 23RGD/mole silk.

Another particular embodiment provides for an implantable gel formulation comprising silk fibroin and the 23RGD wherein the gel formulation comprises from about 4% to about 8% silk fibroin and the 23RGD concentration is about 1:10 to 10:1 moles of 23RGD per mole of silk fibroin.

In another embodiment, the gel phase comprises a protein structure consisting predominantly of the β-sheet conformation with components of α-helix, random coil, and unordered structures.

Another example embodiment of invention relates to a kit including a sterile silk gel formulation packaged in a 1 mL syringe with a 26 g needle and blended with a material commonly referred to as a "local anesthetic". This anesthetic might be more specifically lidocane. Dependent upon application, the kit includes syringes sizes from 0.5 mL to 60 mL, where applications requiring larger volumes (e.g., bone fillers, disc fillers) are supplied in a larger size syringe. Additionally, needle gage is adjusted according to injection site with an acceptable range of 10 g to 30 g needles. For example, 26 g to 30 g needles are used for intradermal injections. Furthermore, the local anesthetic is not blended into the formulation for applications where the anesthetic is preferably applied separately or applications for which an anesthetic is not needed.

In another embodiment, the silk gel formulation is processed in a batch system by obtaining an 8% silk solution, adding ethanol/23RGD to generate a firm 4%-6% gel, allowing this to stand for at least 24 hours. The gel is then rinsed in water to remove residual free gelation agents (both 23RGD and ethanol), adding saline solution to the gel as a carrier phase and developing a homogeneous suspension. Suspension viscosity/injectability is then tailored by manipulating gel concentration, particle size, and saline content, milling the gel to a desired particle size that makes the gel injectable through a needle (for example a 30 g needle), loading the gel into a syringe, and sterilizing the gel with gamma irradiation.

In another aspect, the injectable formulation includes a gel comprising substantially sericin-depleted silk fibroin and an amphiphilic peptide and a carrier phase, wherein the formulation, upon injection, remains substantially at the injection site for about two weeks to about sixty months depending upon a desired application. For example, one formulation, for soft tissue filling may employ a 1%-6% silk gel with 20%-50% saline carrier at an average particle size of 20 µm-30 µm, and be deliverable through a 26 g-30 g needle with ~5N of force while remaining substantially for one month to nine months at the injection site. One example formulation for hard tissue filling may employ a 6%-10% silk gel with 0%-25% saline carrier at a 50 µm-1000 µm particle size, and be deliverable through a 10 g-18 g needle at ~5N of force while remaining substantially for nine to fifteen months at the injection site.

In one embodiment, the present invention provides a five-amino acid peptide "tail" capable of linking or conjugating a molecule X to a silk molecule or fibroin when the molecule X is attached to the tail. In one embodiment, the tail peptide comprises of hydrophobic and/or apolar amino acid residues. In another embodiment, the tail peptide comprises of amino acid residues capable of hydrogen bonding and/or covalent bonding. In other embodiments, the tail peptide comprises any of the twenty conventional standard amino acid residues.

In one embodiment, the five-amino acid peptide "tail" comprises amino acid residues that are part hydrophobic (i.e. the part of the side-chain nearest to the protein main-chain), for e.g. arginine and lysine.

In one embodiment, the five-amino acid peptide "tail" is separated from a molecule X by a spacer peptide. The length of the space peptide can be of variable length.

In one embodiment, the molecule X is any biological molecule or fragment thereof. In other embodiments, the molecule X is any recombinant, synthetic, or non-native polymeric compounds. Basically, a molecule X is any entity, natural or synthetic, that can be useful and can be use in the context of silk hydrogels.

In one embodiment, the present invention provides a synthetic molecule having the formula: (molecule X)n-(spacer peptide)$_{0-300}$-(tail)-NH$_2$ for linking with silk molecule or fibroin, wherein "n" is a whole integer ranging from 1-30, and wherein the amino acid residues of the spacer ranges from 0-300.

In one embodiment, the invention provides a method of conjugating a molecule X to a silk molecule or fibroin comprising mixing a synthetic molecule having the formula: (molecule X)n-(spacer peptide)$_{0-300}$-(tail)-NH$_2$ with a silk molecule or fibroin or silk solution, wherein "n" is a whole integer ranging from 1-30, and wherein the amino acid residues of the spacer ranges from 0-300.

DETAILED DESCRIPTION OF INVENTION

Figure 1A:
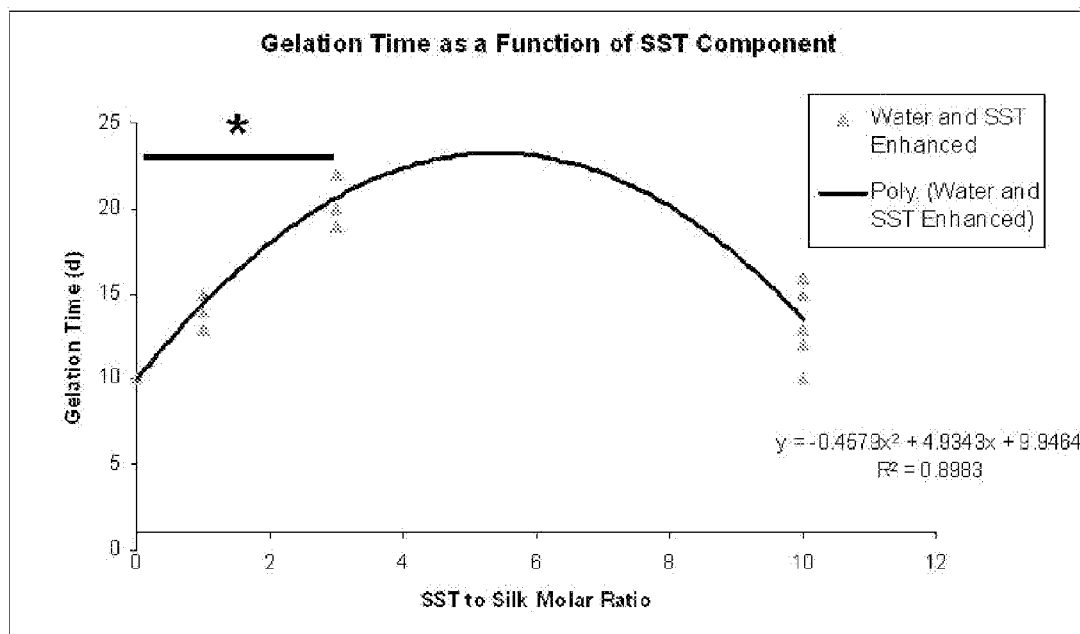
FIG. 1 illustrates the impact of 23RGD on the gelation times of silk hydrogels manufactured under various circumstances for example without enhancers or with a water/23RGD enhancer (FIG. 1A), or with an ethanol enhancer or combined ethanol-23RGD enhancers (FIG. 1B). Depending upon the ratio of 23RGD to silk used and the specific enhancer solvents, the peptide may function as either an accelerant or decelerant of the process.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

As used herein and in the claims, the singular forms "a," "an," and "the" include the plural reference unless the context clearly indicates otherwise. Thus, for example, the reference to a peptide is a reference to one or more such peptides, including equivalents thereof known to those skilled in the art. Other than in the operating examples, or where otherwise indicated, all numbers expressing quantities of ingredients or reaction conditions used herein should be understood as modified in all instances by the term "about."

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Unless defined otherwise, all technical and scientific terms used herein have the same meaning as those commonly understood to one of ordinary skill in the art to which this invention pertains. Although any known methods, devices, and materials may be used in the practice or testing of the invention, the methods, devices, and materials in this regard are described here.

As used herein, the term "about" means that the item, parameter or term so qualified encompasses a range of plus or minus ten percent above and below the value of the stated item, parameter or term.

Aspects of the present specification provide, in part, a depolymerized silk fibroin. As used herein, the term "depolymerized silk fibroin" is synonymous with "dissolved silk" and "dissolved silk fibroin" and refers to silk fibroin existing primarily as monomers or other lower oligomeric units. Treatment of naturally-occurring fibrous silk with a dissolution agent, such as, e.g., a chaotropic agent results in depolymerized silk fibroin. The depolymerized silk fibroin used for preparing silk fibroin hydrogel is an intermediate in the silk hydrogel production process and a direct precursor to the hydrogel material. The depolymerized silk fibroin can be made from raw cocoons, previously degummed silk or any other partially cleaned silk. This may also include material commonly termed as "waste" from the reeling process, i.e. short fragments of raw or degummed silk, the sole precaution being that the silk must be substantially cleaned of sericin prior to making fibroin solution and inducing gel formation. A particular source of raw silk is from common domesticated silkworm *B. mori*, though several other sources of silk may be appropriate. This includes other strains of Bombycidae including *Antheraea pernyi, Antheraea yamamai, Antheraea mylitta, Antheraea assama*, and *Philosamia cynthia ricini*, as well as silk producing members of the families Saturnidae, Thaumetopoeidae, and silk-producing members of the order Araneae. The material may also be obtained from other spider, caterpillar, or recombinant sources.

Aspects of the present specification provide, in part, a polymerized silk fibroin. As used herein, the term "polymerized silk fibroin" is synonymous with "silk fibroin" and refers to silk fibroin existing primarily as a polymer. A polymerized silk fibroin or silk fibroin is made by, e.g., a gelation process disclosed in the present specification.

The hydrogels and formulations disclosed in the present specification provide for a depolymerized silk fibroin and/or silk fibroin that is substantially free of sericin. Methods for performing sericin extraction have been described in pending U.S. patent application Ser. No. 10/008,924, Publication No. 20030100108, *Matrix for the production of tissue engineered ligaments, tendons and other tissue*, published May 29, 2003. That application refers to cleaned fibroin fibers spun into yarns, used to create a porous, elastic matrix suitable as a substrate for applications requiring very high tensile strength, such as bioengineered ligaments and tendons.

Extractants such as urea solution, hot water, enzyme solutions including papain among others which are known in the art to remove sericin from fibroin would also be acceptable for generation of the silk. Mechanical methods may also be used for the removal of sericin from silk fibroin. This includes but is not limited to ultrasound, abrasive scrubbing and fluid flow. The rinse post-extraction is conducted preferably with vigorous agitation to remove substantially any ionic contaminants, soluble, and in soluble debris present on the silk as monitored through microscopy and solution electrochemical measurements. A criterion is that the extractant predictably and repeatably remove the sericin coat of the source silk without significantly compromising the molecular structure of the fibroin. For example, an extraction may be evaluated for sericin removal via mass loss, amino acid content analysis, and scanning electron microscopy. Fibroin degradation may in turn be monitored by FTIR analysis, standard protein gel electrophoresis and scanning electron microscopy.

In certain cases, the silk utilized for generation of a silk hydrogel has been substantially depleted of its native sericin content (i.e., ≦4% (w/w) residual sericin in the final extracted silk). Alternatively, higher concentrations of residual sericin may be left on the silk following extraction or the extraction step may be omitted. In aspects of this embodiment, the sericin-depleted silk fibroin has, e.g., about 1% (w/w) residual sericin, about 2% (w/w) residual sericin, about 3% (w/w) residual sericin, or about 4% (w/w) residual sericin. In other aspects of this embodiment, the sericin-depleted silk fibroin has, e.g., at most 1% (w/w) residual sericin, at most 2% (w/w) residual sericin, at most 3% (w/w) residual sericin, or at most 4% (w/w) residual sericin. In yet other aspects of this embodiment, the sericin-depleted silk fibroin has, e.g., about 1% (w/w) to about 2% (w/w) residual sericin, about 1% (w/w) to about 3% (w/w) residual sericin, or about 1% (w/w) to about 4% (w/w) residual sericin.

In certain cases, the silk utilized for generation of a silk hydrogel is entirely free of its native sericin content. As used herein, the term "entirely free (i.e. "consisting of" terminology) means that within the detection range of the instrument or process being used, the substance cannot be detected or its presence cannot be confirmed.

In certain cases, the silk utilized for generation of a silk hydrogel is essentially free of its native sericin content. As used herein, the term "essentially free" (or "consisting essentially of") means that only trace amounts of the substance can be detected.

Additionally, the possibility exists for deliberately modifying hydrogel properties through controlled partial removal of silk sericin or deliberate enrichment of source silk with sericin. This may function to improve hydrogel hydrophilicity and eventual host acceptance in particular biological settings despite sericin antigenicity.

After initial degumming or sericin removal from fibrous silk used for generation of a hydrogel, the silk is rinsed free of gross particulate debris. It is of concern to remove such particles as either solvent (i.e., specific solvent of interest for device generation) soluble or insoluble compounds may profoundly affect the outcome of the hydrogel generated from the intermediate solution. Insoluble compounds may serve as nucleation points, accelerating the gelation phenomenon and potentially altering subsequent hydrogel protein structure. Soluble compounds may also serve to interface with the protein network of the hydrogel, altering the organizational state of the device. Either type of compound could also compromise biocompatibility of the device.

Prior to dissolution, the prepared silk may be subjected to association of various molecules. The binding between these compounds and the silk molecules may be unaffected by the dissolving agent used for preparation of silk solution intermediate. The method for coupling the modifying compound to the prepared silk may vary dependent upon the specific nature of the bond desired between silk sequence and the modifier. Methods are not limited to but may include hydrogen bonding through affinity adsorption, covalent crosslinking of compounds or sequential binding of inactive and active compounds. These molecules may include, but would not be limited to, inorganic compounds, peptides, proteins, glycoproteins, proteoglycans, ionic compounds, natural, and synthetic polymers. Such peptides, proteins, glycoproteins and proteoglycans may include classes of molecules generally referred to as "growth factors", "cytokines", "chemokines", and "extracellular matrix compounds". These compounds might include such things as surface receptor binding motifs like arginine-glycine-aspartic acid (RGD), growth factors like basic fibroblast growth factor (bFGF), platelet derived growth factor (PDGF), transforming growth factor (TGF), cytokines like tumor necrosis factor (TNF), interferon (IFN), interleukins (IL), and structural sequences including collagen, elastin, hyaluronic acid and others. Additionally recombinant, synthetic, or non-native polymeric compounds might be used as decoration including chitin, poly-lactic acid (PLA), and poly-glycolic acid (PGA). Other compounds linked to the material may include classes of molecules generally referred to as tracers, contrasting agents, aptamers, avimers, peptide nuclei acids and modified polysaccharide coatings.

For example, the initially dissolved silk may be generated by a 4 hour digestion at 60° C. of pure silk fibroin at a concentration of 200 g/L in a 9.3 M aqueous solution of lithium bromide to a silk concentration of 20% (w/v). This process may be conducted by other means provided that they deliver a similar degree of dissociation to that provided by a 4 hour digestion at 60° C. of pure silk fibroin at a concentration of 200 g/L in a 9.3 M aqueous solution of lithium bromide. The primary goal of this is to create uniformly and repeatably dissociated silk fibroin molecules to ensure similar fibroin solution properties and, subsequently, device properties. Less substantially dissociated silk solution may have altered gelation kinetics resulting in differing final gel properties. The degree of dissociation may be indicated by Fourier-transform Infrared Spectroscopy (FTIR) or x-ray diffraction (XRD) and other modalities that quantitatively and qualitatively measure protein structure. Additionally, one may confirm that heavy and light chain domains of the silk fibroin dimer have remained intact following silk processing and dissolution. This may be achieved by methods such as standard protein sodium-dodecyl-sulfate polyacrylamide gel electrophoresis (SDS-PAGE) which assess molecular weight of the independent silk fibroin domains.

System parameters which may be modified in the initial dissolution of silk include but are not limited to solvent type, silk concentration, temperature, pressure, and addition of mechanical disruptive forces. Solvent types other than aqueous lithium bromide may include but are not limited to aqueous solutions, alcohol solutions, 1,1,1,3,3,3-hexafluoro-2-propanol, and hexafluoroacetone, 1-butyl-3-methylimidazolium. These solvents may be further enhanced by addition of urea or ionic species including lithium bromide, calcium chloride, lithium thiocyanate, zinc chloride, magnesium salts, sodium thiocyanate, and other lithium and calcium halides would be useful for such an application. These solvents may also be modified through adjustment of pH either by addition of acidic of basic compounds.

Further tailoring of the solvent system may be achieved through modification of the temperature and pressure of the solution, as ideal dissolution conditions will vary by solvent selected and enhancers added. Mechanical mixing methods employed may also vary by solvent type and may vary from general agitation and mixing to ultrasonic disruption of the protein aggregates. Additionally, the resultant dissolved silk concentration may be tailored to range from about 1% (w/v) to about 30% (w/v). It may be possible to expand this range to include higher fractions of dissolved silk depending upon the specific solvent system utilized. In one example, following initial dissolution of the processed silk, the silk protein may be left in a pure aqueous solution at 8% (w/v) silk. This is accomplished by removal of the residual solvent system while simultaneously ensuring that the aqueous component of the silk solution is never fully removed nor compromised. In a situation which involves an initial solution of 200 g/L silk in a 9.3 M aqueous solution of lithium bromide, this end is accomplished by a dialysis step.

In aspects of this embodiment, the depolymerized silk fibroin (dissolved silk fibroin) has a concentration of, e.g., about 1% (w/v), about 2% (w/v), about 3% (w/v), about 4% (w/v), about 5% (w/v), about 6% (w/v), about 7% (w/v), about 8% (w/v), about 9% (w/v), about 10% (w/v), about 12% (w/v), about 15% (w/v), about 18% (w/v), about 20% (w/v), about 25% (w/v), or about 30% (w/v). In other aspects of this embodiment, the depolymerized silk fibroin (dissolved silk fibroin) has a concentration of, e.g., at least 1% (w/v), at least 2% (w/v), at least 3% (w/v), at least 4% (w/v), at least 5% (w/v), at least 6% (w/v), at least 7% (w/v), at least 8% (w/v), at least 9% (w/v), at least 10% (w/v), at least 12% (w/v), at least 15% (w/v), at least 18% (w/v), at least 20% (w/v), at least 25% (w/v), or at least 30% (w/v). In yet other aspects of this embodiment, the depolymerized silk fibroin (dissolved silk fibroin) has a concentration of, e.g., about 1% (w/v) to about 5% (w/v), about 1% (w/v) to about 10% (w/v), about 1% (w/v) to about 15% (w/v), about 1% (w/v) to about 20% (w/v), about 1% (w/v) to about 25% (w/v), about 1% (w/v) to about 30% (w/v), about 5% (w/v) to about 10% (w/v), about 5% (w/v) to about 15% (w/v), about 5% (w/v) to about 20% (w/v), about 5% (w/v) to about 25% (w/v), about 5% (w/v) to about 30% (w/v), about 10% (w/v) to about 15% (w/v), about 10% (w/v) to about 20% (w/v), about 10% (w/v) to about 25% (w/v), or about 10% (w/v) to about 30% (w/v).

Example dialysis conditions include a 3 mL-12 mL sample volume dialysis cassettes with 3.5 kD molecular weight cut-off cellulose membranes dialyzed for three days against ultra-pure water with a series of six changes at regular intervals while stirring constantly. Each cassette, 5 mL-12 mL cartridge size, may be loaded (for example via 20-mL syringe) with 12 mL of a 20% solution of silk dissolved in 9.3 M lithium bromide via an 18 gauge needle. The resultant silk solution may be 8%±0.5% (w/v). The silk solution may be stored at a range of −80° C. to 37° C., such as 4° C. prior to use. One method is to dialyze the solution against water using a 3.5 kD molecular weight cutoff cellulose membrane, for example, at one 12 mL cartridge per 1 L water in a 4 L beaker with stirring for 48 hours or 72 hours. Water may be changed several times during the dialysis, for example at 1 hour, 4 hours, 12 hours, 24 hours, and 36 hours (total of six rinses). In other embodiments, this membrane may take the shape of a cassette, tubing or any other semi-permeable membrane in a batch, semi-continuous or continuous system. If desired, the concentration of silk in solution may be raised following the original dialysis step by inclusion of a second dialysis against a hygroscopic polymer such as PEG, a poly(ethylene oxide) or amylase.

The parameters applied to the dialysis step may be altered according to the specific needs or requirements of the particular solution system involved. Although it may be undesirable to change membrane composition or pore size in the interests of maintaining efficiency of the process, it would be possible to change the structuring of the dialysis barrier, as a dialysis tube or any large semi-permeable membrane of similar construction should suffice. Additionally it should be considered that any alteration in the nature of the physical dialysis interface between solution and buffer might alter rates of ion flux and thereby create membrane-localized boundary conditions which could affect solution dialysis and gelation rate kinetics. The duration and volume ratios associated with this dialysis process must be tailored to any new system as well, and removal of the solvent phase should be ensured after purification before proceeding.

It is also possible to change the buffer phase in the dialysis system, altering water purity or adding hygroscopic polymers to simultaneously remove ions and water from the initial silk solution. For example, if necessary, the silk solution can be concentrated by dialysis against a hygroscopic polymer, for example, PEG, a polyethylene oxide or amylase. The apparatus used for dialysis can be cassettes, tubing, or any other semi-permeable membrane.

Insoluble debris may be removed from the dialyzed silk solution by centrifugation or filtration. For example, the dialyzed silk may be removed from the cassette with a needle and syringe (e.g., an 18 g needle at 20 mL syringe), and placed into a clean centrifuge tube with sufficient volume (e.g., 40 mL). The centrifuge may be run at 30,000 g relative centrifugal force (RCF) for 30 minutes at 4° C. The resulting supernatant may be collected and centrifuged again under identical conditions, and the remaining supernatant collected (e.g., in a 50 mL test tube) and stored at 4° C. The silk solution may also be evaluated via X-ray photoelectron spectroscopy (to check for lithium bromide residue) and dry mass (to check solution for dry protein mass, concentration w/v).

Additionally, dependent upon the initial silk solvent, it might be desirable to remove portions of either the silk phase or solvent phase from the solution via an affinity column separation. This could be useful in either selectively binding specific solvent molecules or specific solute molecules to be eluted later in a new solvent.

The possibility also exists for a lyophilization of the depolymerized silk fibroin (dissolved silk) followed by a reconstitution step. This would be most useful in a case where removing a solvent, is unlikely to leave residue behind.

In the case of a lyophilized solution, either used as a purification step or as a procedure subsequent to purification, the type of solvent used for reconstitution might be tailored for the process at hand. Desirable solvents might include but are not limited to aqueous alcohol solutions, aqueous solutions with altered pH, and various organic solutions. These solvents may be selected based upon a number of parameters which may include but are not limited to an enhanced gelation rate, altered gel crystalline structure, altered solution intermediate shelf-life, altered silk solubility, and ability to interact with environmental milieu such as temperature and humidity.

In certain embodiments, a silk hydrogel is prepared from dissolved silk fibroin solution that uses an agent to enhance gelation and an agent to improve the gel's biocompatibility. In some instances, the same agent both enhances gelation and improves biocompatibility. An example agent that both improves gel biocompatibility and serves as a gelation enhancer is an amphiphilic peptide which binds to silk molecules through hydrophobic interactions, such as, e.g., a RGD motif containing peptide like 23RGD. In other instances, different agents serve these purposes. An example of an agent that serves as a gelation enhancer is an alcohol, such as, e.g., ethanol, methanol, and isopropanol; glycerol; and acetone.

Regarding gelation enhancers, to accelerate the phenomenon of silk gelation, a depolymerized silk fibroin solution (dissolved silk solution) may be mixed with pure alcohol or aqueous alcohol solution at varied volume ratios accompanied by mixing, either through stirring, shaking or any other form of agitation. This alcohol solution enhancer may then have a quantity of an amphiphilic peptide added as a further enhancer of the final gel outcome. The extent of acceleration may be heightened or lessened by adding a larger or smaller enhancer component to the system.

In addition to organics, the gelation rate may be enhanced by increasing the concentration of the depolymerized silk fibroin (dissolved silk). This is done by methods including but not limited to dialysis of intermediate silk solution against a buffer incorporating a hygroscopic species such as polyethylene glycol, a lyophilization step, and an evaporation step. Increased temperature may also be used as an enhancer of the gelation process. In addition to this, manipulation of intermediate silk solution pH by methods including but not limited to direct titration and gas exchange may be used to enhance the gelation process. Introduction of select ionic species including calcium and potassium in particular may also be used to accelerate gelation rate.

Nucleating agents including organic and inorganic species, both soluble and insoluble in an aqueous silk solution intermediate may be used to enhance the gelation process. These may include but are not limited to peptide sequences which bind silk molecules, previously gelled silk, and poorly soluble β-sheet rich structures. A further means of accelerating the gelation process is through the introduction of mechanical excitation. This might be imparted through a shearing device, ultrasound device, or mechanical mixer. It should be borne in mind that any of these factors might conceivably be used in concert with any other or group of others and that the regime would need to be tailored to the desired outcome.

Figure 1B:
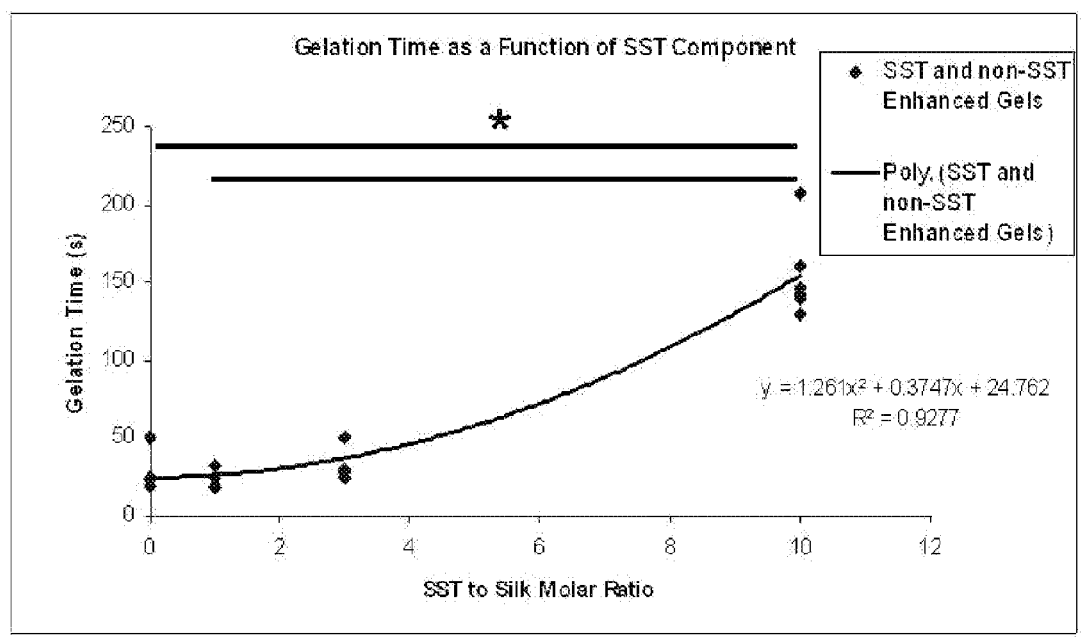

The time necessary for complete silk solution gelation may vary from seconds to hours or days, depending on the values of the above mentioned parameters as well as the initial state of aggregation and organization found in the silk solution (FIG. 1). The volume fraction of added enhancer may vary from about 0% to about 99% of the total system volume (i.e., either component may be added to a large excess of the other or in any relative concentration within the interval). The concentration of silk solution used can range from about 1% (w/v) to about 20% (w/v). The enhancer can be added to silk solution or the silk solution can be added to enhancer. The formed silk hydrogel may be further chemically or physically cross-linked to gain altered mechanical properties.

In aspects of this embodiment, an enhancer solution is added to a depolymerized silk fibroin (dissolved silk fibroin) solution, the depolymerized silk fibroin solution having a concentration of depolymerized silk fibroin of, e.g., about 1% (w/v), about 2% (w/v), about 3% (w/v), about 4% (w/v), about 5% (w/v), about 6% (w/v), about 7% (w/v), about 8% (w/v), about 9% (w/v), about 10% (w/v), about 12% (w/v), about 15% (w/v), about 18% (w/v), about 20% (w/v), about 25% (w/v), or about 30% (w/v). In other aspects of this embodiment, an enhancer solution is added to a depolymerized silk fibroin (dissolved silk fibroin) solution, the depolymerized silk fibroin solution having a concentration of depolymerized silk fibroin of, e.g., at least 1% (w/v), at least 2% (w/v), at least 3% (w/v), at least 4% (w/v), at least 5% (w/v), at least 6% (w/v), at least 7% (w/v), at least 8% (w/v), at least 9% (w/v), at least 10% (w/v), at least 12% (w/v), at least 15% (w/v), at least 18% (w/v), at least 20% (w/v), at least 25% (w/v), or at least 30% (w/v). In yet other aspects of this embodiment, an enhancer solution is added to a depolymerized silk fibroin (dissolved silk fibroin) solution, the depolymerized silk fibroin solution having a concentration of depolymerized silk fibroin of, e.g., about 1% (w/v) to about 5% (w/v), about 1% (w/v) to about 10% (w/v), about 1% (w/v) to about 15% (w/v), about 1% (w/v) to about 20% (w/v), about 1% (w/v) to about 25% (w/v), about 1% (w/v) to about 30% (w/v), about 5% (w/v) to about 10% (w/v), about 5% (w/v) to about 15% (w/v), about 5% (w/v) to about 20% (w/v), about 5% (w/v) to about 25% (w/v), about 5% (w/v) to about 30% (w/v), about 10% (w/v) to about 15% (w/v), about 10% (w/v) to about 20% (w/v), about 10% (w/v) to about 25% (w/v), or about 10% (w/v) to about 30% (w/v).

A further aspect of some embodiments relates to the inclusion of a peptide in the silk fibroin solution. Examples of such peptides include amphiphilic peptides. Amphiphilic molecules possess both hydrophilic and hydrophobic properties. Many other amphiphilic molecules interact strongly with biological membranes by insertion of the hydrophobic part into the lipid membrane, while exposing the hydrophilic part to the aqueous environment. Particular embodiments of hydrogels include silk fibroin, silk fibroin with 23RGD, silk fibroin with alcohol and 23RGD, and silk fibroin with alcohol, 23RGD, and saline/PBS. The amount, relative ratio and sequence of adding the components will change according to the specific requirement for the device.

Additionally, an amphiphilic peptide may accelerate the phenomenon of silk gelation under certain circumstances. Such gel may be produced through combination of dissolved silk fibroin solution and an enhancer solution of amphiphilic peptide in alcohol across the silk concentration ranges from about 1% (w/v) to about 20% (w/v), amphiphilic peptide concentration ranges from about 1:100 to 100:1 moles 23RGD:moles silk, and alcohol concentration ranges from about 1% (v/v) to about 99% (v/v) before removal. Thus, for example, a particular silk gel is produced through direct contact between an aqueous solution of depolymerized silk fibroin and an enhancer solution comprising 23RGD in ethanol. For example, the dissolved silk solution may be mixed with a 23RGD suspended in pure ethanol or aqueous ethanol solution at varied volume ratios accompanied by mixing, either through stirring, shaking or any other form of agitation.

More specifically, as a non-limiting example, to infuse the silk fibroin hydrogel with 23RGD, the 23RGD is first dissolved in a solution of ethanol and water (e.g., 90% ethanol in purified water) in an amount to generate the planned silk and 23RGD concentrations of the final gel, and mixed (e.g., vortexed until there is no visible 23RGD particulate). This solution is then mixed with dissolved silk solution (e.g., by pipetting rapidly for 1-2 seconds). The gelling mixture may be allowed to stand covered under ambient conditions for a suitable period, for example 24 hours (or 24 hours after the gel has solidified depending on enhancer conditions).

The amount of time required for dissolved silk solutions to gel may vary from seconds to hours or days, depending on the ratio of silk solution volume and enhancer solution volume, dissolved silk fibroin concentration, enhancer solution concentration, enhancer type and amphiphilic peptide concentration. The amphiphilic peptide may be mixed into the dissolved silk solution in a variety of ways, for example water-dissolved amphiphilic peptide can be added to a dissolved silk solution to form a gel; an amphiphilic peptide can be added to water, blended with an alcohol, then added to a dissolved silk solution; or an amphiphilic peptide can be added to a silk fibroin hydrogel. The molar ratio of amphiphilic peptide:silk fibroin can range from 100 to 0.01, the dissolved silk solution concentration can be from about 1% to about 20%.

An example of an amphiphilic peptide is a 23RGD peptide having the amino acid sequence: HOOC-Gly-Arg-Gly-Asp-Ile-Pro-Ala-Ser-Ser-Lys-Gly-Gly-Gly-Gly-Ser-Arg-Leu-Leu-Leu-Leu-Leu-Leu-Arg-NH$_2$ (abbreviated HOOC-GRGDIPASSKG$_4$SRL$_6$R—NH$_2$) (SEQ ID NO: 1). Optionally, each of the arginine residues may be of the D-form, which may stabilize the RG bond to serine proteases. Additionally, the COO-terminus may be acylated to block proteolysis. This example 23RGD has the amino acid sequence Ac—GdRGDIPASSKG$_4$SdRL$_{6d}$R—NH$_2$ (SEQ ID NO: 2). It may be advantageous to include a spacer domain in the RGD peptide, for example, a peptide such as SG$_4$KSSAP (SEQ ID NO: 3) may present the RGD on the surface of the silk biomaterial by optimally separating the cell attachment domain from the bonding sequence at the end of the peptide. The optional leucine tails of this example may interact in a fashion analogous to a leucine zipper, and be driven by entropy from an aqueous solution to form an approximation of a Langmuir-Blodgett (LB), monomolecular film on the surface of materials exposed to such solutions, thus presenting a 'carpet' of RGD attachment sites on those surfaces.

Other proteins or peptides may be used instead of 23RGD if such proteins or peptides have the desired characteristics. Example characteristics include hydrophilic domains that can interfere/enhance/affect silk gelation, and/or cell binding domains that enhance cell adhesion, spreading, and migration, such as RGD, KQAGDV (SEQ ID NO: 4), PHSRN (SEQ ID NO: 5), YIGSR (SEQ ID NO: 6), CDPGYIGSR (SEQ ID NO: 7), IKVAV (SEQ ID NO: 8), RNIAEIIKDI (SEQ ID NO: 9), YFQRYLI (SEQ ID NO: 10), PDSGR (SEQ ID NO: 11), FHRRIKA (SEQ ID NO: 12), PRRARV (SEQ ID NO: 13), and WQPPRARI (SEQ ID NO: 14). See Hersel et al., 24 Biomaterials 4285-415 (2003).

In aspects of this embodiment, a hydrogel comprises a molar ratio of amphiphilic peptide to silk fibroin of, e.g., about 100:1, about 90:1, about 80:1, about 70:1, about 60:1, about 50:1, about 40:1, about 30:1, about 20:1, about 10:1, about 7:1, about 5:1, about 3:1, about 1:1, about 1:3, about 1:5, about 1:7, about 1:10, about 1:20, about 1:30, about 1:40, about 1:50, about 1:60, about 1:70, about 1:80, or about 1:90, or about 1:100. In other aspects of this embodiment, a hydrogel comprises a molar ratio of amphiphilic peptide to silk fibroin of, e.g., at least 100:1, at least 90:1, at least 80:1, at least 70:1, at least 60:1, at least 50:1, at least 40:1, at least 30:1, at least 20:1, at least 10:1, at least 7:1, at least 5:1, at least 3:1, at least 1:1, at least 1:3, at least 1:5, at least 1:7, at least 1:10, at least 1:20, at least 1:30, at least 1:40, at least 1:50, at least 1:60, at least 1:70, at least 1:80, or at least 1:90, or at least 1:100. In yet other aspects of this embodiment, a hydrogel comprises a molar ratio of amphiphilic peptide to silk fibroin of, e.g., at most 100:1, at most 90:1, at most 80:1, at most 70:1, at most 60:1, at most 50:1, at most 40:1, at most 30:1, at most 20:1, at most 10:1, at most 7:1, at most 5:1, at most 3:1, at most 1:1, at most 1:3, at most 1:5, at most 1:7, at most 1:10, at most 1:20, at most 1:30, at most 1:40, at most 1:50, at most 1:60, at most 1:70, at most 1:80, or at most 1:90, or at most 1:100. In still other aspects of this embodiment, a hydrogel comprises a molar ratio of amphiphilic peptide to silk fibroin of, e.g., about 100:1 to about 1:100; about 90:1 to about 1:90; about 80:1 to about 1:80; about 70:1 to about 1:70; about 60:1 to about 1:60; about 50:1 to about 1:50; about 40:1 to about 1:40; about 30:1 to about 1:30; about 20:1 to about 1:20; about 10:1 to about 1:10; about 7:1 to about 1:7; about 5:1 to about 1:5; or about 3:1 to about 1:3.

The use of an amphiphilic peptide not only alters the protein structure characteristics of silk fibroin protein, but in so doing alters its resistance to proteolytic bioresorption in vitro. These alterations in proteolytic bioresorption resistance stem from aspects of the protein structure alteration as α-helix and random coil are typically thought to be less stable and therefore more susceptible to proteolytic bioresorption than β-sheet regions of silk. β-turn and β-strand regions of the hydrogel disclosed in the present specification are most resistant to proteolytic bioresorption as opposed to regions of α-helices and random coils. Through deliberate manipulation of this protein structure by means of controlled solution concentration and addition of enhancer factors (type, concentration, and driving gradient), gelation kinetics and resultant gel properties might be controlled to deliver optimal outcomes in terms of degradative and resultant biological behaviors. The impact of amphiphilic peptide addition to silk hydrogel in a silk hydrogel is evident upon examination of data obtained through implantation studies conducted in vivo, both subcutaneously in rats and intradermally in the dermis of guinea pigs. See Example 10.

In an embodiment, a hydrogel comprises a silk fibroin protein wherein the protein structure is resist bioresorption. In aspects of this embodiment, a hydrogel comprising a silk fibroin has a protein structure that makes the hydrogel resist to bioresorption for, e.g., about 10 days, about 20 days, about 30 days, about 40 days, about 50 days, about 60 days, about 70 days, about 80 days, or about 90 days. In other aspects of this embodiment, a hydrogel comprising a silk fibroin has a protein structure that makes the hydrogel resist to bioresorption for, e.g., at least 10 days, at least 20 days, at least 30 days, at least 40 days, at least 50 days, at least 60 days, at least 70 days, at least 80 days, or at least 90 days. In yet other aspects of this embodiment, a hydrogel comprising a silk fibroin has a protein structure that makes the hydrogel resist to bioresorption for, e.g., about 10 days to about 30 days, about 20 days to about 50 days, about 40 days to about 60 days, about 50 days to about 80 days, or about 60 days to about 90 days.

In another embodiment, a hydrogel comprising a silk fibroin and an amphiphilic peptide has a protein structure that makes the hydrogel resist to bioresorption. In aspects of this embodiment, a hydrogel comprising a silk fibroin and an amphiphilic peptide has a protein structure that makes the hydrogel resist to bioresorption for, e.g., about 10 days, about 20 days, about 30 days, about 40 days, about 50 days, about 60 days, about 70 days, about 80 days, or about 90 days. In other aspects of this embodiment, a hydrogel comprising a silk fibroin and an amphiphilic peptide has a protein structure that makes the hydrogel resist to bioresorption for, e.g., at least 10 days, at least 20 days, at least 30 days, at least 40 days, at least 50 days, at least 60 days, at least 70 days, at least 80 days, or at least 90 days. In yet other aspects of this embodiment, a hydrogel comprising a silk fibroin and an amphiphilic peptide has a protein structure that makes the hydrogel resist to bioresorption for, e.g., about 10 days to about 30 days, about 20 days to about 50 days, about 40 days to about 60 days, about 50 days to about 80 days, or about 60 days to about 90 days.

In yet another embodiment, a hydrogel comprising a silk fibroin has a protein structure that substantially includes β-turn and β-strand regions. In aspects of this embodiment, a hydrogel comprising a silk fibroin and an amphiphilic peptide has a protein structure including, e.g., about 10% β-turn and β-strand regions, about 20% β-turn and β-strand regions, about 30% β-turn and β-strand regions, about 40% β-turn and β-strand regions, about 50% β-turn and β-strand regions, about 60% β-turn and β-strand regions, about 70% β-turn and β-strand regions, about 80% β-turn and β-strand regions, about 90% β-turn and β-strand regions, or about 100% β-turn and β-strand regions. In other aspects of this embodiment, a hydrogel comprising a silk fibroin has a protein structure including, e.g., at least 10% β-turn and β-strand regions, at least 20% β-turn and β-strand regions, at least 30% β-turn and β-strand regions, at least 40% β-turn and β-strand regions, at least 50% β-turn and β-strand regions, at least 60% β-turn and β-strand regions, at least 70% β-turn and β-strand regions, at least 80% β-turn and β-strand regions, at least 90% β-turn and β-strand regions, or at least 95% β-turn and β-strand regions. In yet other aspects of this embodiment, a hydrogel comprising a silk fibroin has a protein structure including, e.g., about 10% to about 30% β-turn and β-strand regions, about 20% to about 40% β-turn and β-strand regions, about 30% to about 50% β-turn and β-strand regions, about 40% to about 60% β-turn and β-strand regions, about 50% to about 70% β-turn and β-strand regions, about 60% to about 80% β-turn and β-strand regions, about 70% to about 90% β-turn and β-strand regions, about 80% to about 100% β-turn and β-strand regions, about 10% to about 40% β-turn and β-strand regions, about 30% to about 60% β-turn and β-strand regions, about 50% to about 80% β-turn and β-strand regions, about 70% to about 100% β-turn and β-strand regions, about 40% to about 80% β-turn and β-strand regions, about 50% to about 90% β-turn and β-strand regions, about 60% to about 100% β-turn and β-strand regions, or about 50% to about 100% β-turn and β-strand regions.

In yet another embodiment, a hydrogel comprising a silk fibroin and an amphiphilic peptide has a protein structure that is substantially-free of α-helix and random coil regions. In aspects of this embodiment, a hydrogel comprising a silk fibroin has a protein structure including, e.g., about 5% α-helix and random coil regions, about 10% α-helix and random coil regions, about 15% α-helix and random coil regions, about 20% α-helix and random coil regions, about 25% α-helix and random coil regions, about 30% α-helix and random coil regions, about 35% α-helix and random coil regions, about 40% α-helix and random coil regions, about 45% α-helix and random coil regions, or about 50% α-helix and random coil regions. In other aspects of this embodiment, a hydrogel comprising a silk fibroin has a protein structure including, e.g., at most 5% α-helix and random coil regions, at most 10% α-helix and random coil regions, at most 15% α-helix and random coil regions, at most 20% α-helix and random coil regions, at most 25% α-helix and random coil regions, at most 30% α-helix and random coil regions, at most 35% α-helix and random coil regions, at most 40% α-helix and random coil regions, at most 45% α-helix and random coil regions, or at most 50% α-helix and random coil regions. In yet other aspects of this embodiment, a hydrogel comprising a silk fibroin has a protein structure including, e.g., about 5% to about 10% α-helix and random coil regions, about 5% to about 15% α-helix and random coil regions, about 5% to about 20% α-helix and random coil regions, about 5% to about 25% α-helix and random coil regions, about 5% to about 30% α-helix and random coil regions, about 5% to about 40% α-helix and random coil regions, about 5% to about 50% α-helix and random coil regions, about 10% to about 20% α-helix and random coil regions, about 10% to about 30% α-helix and random coil regions, about 15% to about 25% α-helix and random coil regions, about 15% to about 30% α-helix and random coil regions, or about 15% to about 35% α-helix and random coil regions.

In still another embodiment, a hydrogel comprising a silk fibroin and an amphiphilic peptide has a protein structure that substantially includes β-turn and β-strand regions. In aspects of this embodiment, a hydrogel comprising a silk fibroin and an amphiphilic peptide has a protein structure including, e.g., about 10% β-turn and β-strand regions, about 20% β-turn and β-strand regions, about 30% β-turn and β-strand regions, about 40% β-turn and β-strand regions, about 50% β-turn and β-strand regions, about 60% β-turn and β-strand regions, about 70% β-turn and β-strand regions, about 80% β-turn and β-strand regions, about 90% β-turn and β-strand regions, or about 100% β-turn and β-strand regions. In other aspects of this embodiment, a hydrogel comprising a silk fibroin and an amphiphilic peptide has a protein structure including, e.g., at least 10% β-turn and β-strand regions, at least 20% β-turn and β-strand regions, at least 30% β-turn and β-strand regions, at least 40% β-turn and β-strand regions, at least 50% β-turn and β-strand regions, at least 60% β-turn and β-strand regions, at least 70% β-turn and β-strand regions, at least 80% β-turn and β-strand regions, at least 90% β-turn and β-strand regions, or at least 95% β-turn and β-strand regions. In yet other aspects of this embodiment, a hydrogel comprising a silk fibroin and an amphiphilic peptide has a protein structure including, e.g., about 10% to about 30% β-turn and β-strand regions, about 20% to about 40% β-turn and β-strand regions, about 30% to about 50% β-turn and β-strand regions, about 40% to about 60% β-turn and β-strand regions, about 50% to about 70% β-turn and β-strand regions, about 60% to about 80% β-turn and β-strand regions, about 70% to about 90% β-turn and β-strand regions, about 80% to about 100% β-turn and β-strand regions, about 10% to about 40% β-turn and β-strand regions, about 30% to about 60% β-turn and β-strand regions, about 50% to about 80% β-turn and β-strand regions, about 70% to about 100% β-turn and β-strand regions, about 40% to about 80% β-turn and β-strand regions, about 50% to about 90% β-turn and β-strand regions, about 60% to about 100% β-turn and β-strand regions, or about 50% to about 100% β-turn and β-strand regions.

In still another embodiment, a hydrogel comprising a silk fibroin and an amphiphilic peptide has a protein structure that is substantially-free of α-helix and random coil regions. In aspects of this embodiment, a hydrogel comprising a silk fibroin and an amphiphilic peptide has a protein structure including, e.g., about 5% α-helix and random coil regions, about 10% α-helix and random coil regions, about 15% α-helix and random coil regions, about 20% α-helix and random coil regions, about 25% α-helix and random coil regions, about 30% α-helix and random coil regions, about 35% α-helix and random coil regions, about 40% α-helix and random coil regions, about 45% α-helix and random coil regions, or about 50% α-helix and random coil regions. In other aspects of this embodiment, a hydrogel comprising a silk fibroin and an amphiphilic peptide has a protein structure including, e.g., at most 5% α-helix and random coil regions, at most 10% α-helix and random coil regions, at most 15% α-helix and random coil regions, at most 20% α-helix and random coil regions, at most 25% α-helix and random coil regions, at most 30% α-helix and random coil regions, at most 35% α-helix and random coil regions, at most 40% α-helix and random coil regions, at most 45% α-helix and random coil regions, or at most 50% α-helix and random coil regions. In yet other aspects of this embodiment, a hydrogel comprising a silk fibroin and an amphiphilic peptide has a protein structure including, e.g., about 5% to about 10% α-helix and random coil regions, about 5% to about 15% α-helix and random coil regions, about 5% to about 20% α-helix and random coil regions, about 5% to about 25% α-helix and random coil regions, about 5% to about 30% α-helix and random coil regions, about 5% to about 40% α-helix and random coil regions, about 5% to about 50% α-helix and random coil regions, about 10% to about 20% α-helix and random coil regions, about 10% to about 30% α-helix and random coil regions, about 15% to about 25% α-helix and random coil regions, about 15% to about 30% α-helix and random coil regions, or about 15% to about 35% α-helix and random coil regions.

Aspects of the present specification provide, in part, a silk fibroin hydrogel having a hardness. Hardness refers to various properties of an object in the solid phase that gives it high resistance to various kinds of shape change when force is applied. Hardness is measured using a durometer and is a unitless value that ranges from zero to 100. The ability or inability of a hydrogel to be easily compressed will affect its suitability for application in different tissue replacement roles, i.e., mechanical compliance as bone, fat, connective tissue. Hardness will also affect the ability of a hydrogel to be effectively comminuted, the reason being that a hard material may be more easily and consistently comminuted. Hardness will also affect extrudability, as a soft material may be more readily able to be slightly compressed during injection to pack with other particles or change shape to pass through a syringe barrel or needle.

In an embodiment, a silk fibroin hydrogel exhibits low hardness. In aspects of this embodiment, a silk fibroin hydrogel exhibits a hardness of, e.g., about 5, about 10, about 15, about 20, about 25, about 30, or about 35. In other aspects of this embodiment, a silk fibroin hydrogel exhibits a hardness of, e.g., at most 5, at most 10, at most 15, at most 20, at most 25, at most 30, or at most 35. In yet other aspects of this embodiment, a silk fibroin hydrogel exhibits a hardness of, e.g., about 5 to about 35, about 10 to about 35, about 15 to about 35, about 20 to about 35, or about 25 to about 35, about 5 to about 40, about 10 to about 40, about 15 to about 40, about 20 to about 40, about 25 to about 40, or about 30 to about 40

In an embodiment, a silk fibroin hydrogel exhibits medium hardness. In aspects of this embodiment, a silk fibroin hydrogel exhibits a hardness of, e.g., about 40, about 45, about 50, about 55, or about 60. In other aspects of this embodiment, a silk fibroin hydrogel exhibits a hardness of, e.g., at least 40, at least 45, at least 50, at least 55, or at least 60. In yet other aspects of this embodiment, a silk fibroin hydrogel exhibits a hardness of, e.g., at most 40, at most 45, at most 50, at most 55, or at most 60. In still other aspects of this embodiment, a silk fibroin hydrogel exhibits a hardness of, e.g., about 35 to about 60, about 35 to about 55, about 35 to about 50, about 35 to about 45, about 40 to about 60, about 45 to about 60, about 50 to about 60, about 55 to about 60, about 40 to about 65, about 45 to about 65, about 50 to about 65, about 55 to about 65.

In another embodiment, a silk fibroin hydrogel exhibits high hardness. In aspects of this embodiment, a silk fibroin hydrogel exhibits a hardness of, e.g., about 65, about 70, about 75, about 80, about 85, about 90, about 95, or about 100. In other aspects of this embodiment, a silk fibroin hydrogel exhibits a hardness of, e.g., at least 65, at least 70, at least 75, at least 80, at least 85, at least 90, at least 95, or at least 100. In yet other aspects of this embodiment, a silk fibroin hydrogel exhibits a hardness of, e.g., about 65 to about 100, about 70 to about 100, about 75 to about 100, about 80 to about 100, about 85 to about 100, about 90 to about 100, about 65 to about 75, about 65 to about 80, about 65 to about 85, about 65 to about 90, about 65 to about 95, about 60 to about 75, about 60 to about 80, about 60 to about 85, about 60 to about 90, or about 60 to about 95.

In an embodiment, a silk fibroin hydrogel exhibits high resistant to deformation. In aspects of this embodiment, a silk fibroin hydrogel exhibits resistant to deformation of, e.g., about 100%, about 99%, about 98%, about 97%, about 96%, about 95%, about 94%, about 93%, about 92%, about 91%, about 90%, about 89%, about 88%, about 87%, about 86%, or about 85%. In other aspects of this embodiment, a silk fibroin hydrogel exhibits resistant to deformation of, e.g., at least 99%, at least 98%, at least 97%, at least 96%, at least 95%, at least 94%, at least 93%, at least 92%, at least 91%, at least 90%, at least 89%, at least 88%, at least 87%, at least 86%, or at least 85%. In yet other aspects of this embodiment, a silk fibroin hydrogel exhibits resistant to deformation of, e.g., at most 99%, at most 98%, at most 97%, at most 96%, at most 95%, at most 94%, at most 93%, at most 92%, at most 91%, at most 90%, at most 89%, at most 88%, at most 87%, at most 86%, or at most 85%. In still aspects of this embodiment, a silk fibroin hydrogel exhibits resistant to deformation of, e.g., about 85% to about 100%, about 87% to about 100%, about 90% to about 100%, about 93% to about 100%, about 95% to about 100%, or about 97% to about 100%.

A silk fibroin hydrogel exhibits an elastic modulus. Elastic modulus, or modulus of elasticity, refers to the ability of a hydrogel material to resists deformation, or, conversely, an object's tendency to be non-permanently deformed when a force is applied to it. The elastic modulus of an object is defined as the slope of its stress-strain curve in the elastic deformation region: $\lambda$=stress/strain, where $\lambda$ is the elastic modulus in Pascal's; stress is the force causing the deformation divided by the area to which the force is applied; and strain is the ratio of the change caused by the stress to the original state of the object. Specifying how stresses are to be measured, including directions, allows for many types of elastic moduli to be defined. The three primary elastic moduli are tensile modulus, shear modulus, and bulk modulus.

Tensile modulus (E) or Young's modulus is an objects response to linear strain, or the tendency of an object to deform along an axis when opposing forces are applied along that axis. It is defined as the ratio of tensile stress to tensile strain. It is often referred to simply as the elastic modulus. The shear modulus or modulus of rigidity refers to an object's tendency to shear (the deformation of shape at constant volume) when acted upon by opposing forces. It is defined as shear stress over shear strain. The shear modulus is part of the derivation of viscosity. The shear modulus is concerned with the deformation of a solid when it experiences a force parallel to one of its surfaces while its opposite face experiences an opposing force (such as friction). The bulk modulus (K) describes volumetric elasticity or an object's resistance to uniform compression, and is the tendency of an object to deform in all directions when uniformly loaded in all directions. It is defined as volumetric stress over volumetric strain, and is the inverse of compressibility. The bulk modulus is an extension of Young's modulus to three dimensions.

In another embodiment, a silk fibroin hydrogel exhibits a tensile modulus. In aspects of this embodiment, a silk fibroin hydrogel exhibits a tensile modulus of, e.g., about 1 MPa, about 10 MPa, about 20 MPa, about 30 MPa, about 40 MPa, about 50 MPa, about 60 MPa, about 70 MPa, about 80 MPa, about 90 MPa, about 100 MPa, about 200 MPa, about 300 MPa, about 400 MPa, about 500 MPa, about 750 MPa, about 1 GPa, about 5 GPa, about 10 GPa, about 15 GPa, about 20 GPa, about 25 GPa, or about 30 GPa. In other aspects of this embodiment, a silk fibroin hydrogel exhibits a tensile modulus of, e.g., at least 1 MPa, at least 10 MPa, at least 20 MPa, at least 30 MPa, at least 40 MPa, at least 50 MPa, at least 60 MPa, at least 70 MPa, at least 80 MPa, at least 90 MPa, at least 100 MPa, at least 200 MPa, at least 300 MPa, at least 400 MPa, at least 500 MPa, at least 750 MPa, at least 1 GPa, at least 5 GPa, at least 10 GPa, at least 15 GPa, at least 20 GPa, at least 25 GPa, or at least 30 GPa In yet other aspects of this embodiment, a silk fibroin hydrogel exhibits a tensile modulus of, e.g., about 1 MPa to about 30 MPa, about 10 MPa to about 50 MPa, about 25 MPa to about 75 MPa, about 50 MPa to about 100 MPa, about 100 MPa to about 300 MPa, about 200 MPa to about 400 MPa, about 300 MPa to about 500 MPa, about 100 MPa to about 500 MPa, about 250 MPa to about 750 MPa, about 500 MPa to about 1 GPa, about 1 GPa to about 30 GPa, about 10 GPa to about 30 GPa.

In another embodiment, a silk fibroin hydrogel exhibits shear modulus. In aspects of this embodiment, a silk fibroin hydrogel exhibits a shear modulus of, e.g., about 1 MPa, about 10 MPa, about 20 MPa, about 30 MPa, about 40 MPa, about 50 MPa, about 60 MPa, about 70 MPa, about 80 MPa, about 90 MPa, about 100 MPa, about 200 MPa, about 300 MPa, about 400 MPa, about 500 MPa, about 750 MPa, about 1 GPa, about 5 GPa, about 10 GPa, about 15 GPa, about 20 GPa, about 25 GPa, or about 30 GPa. In other aspects of this embodiment, a silk fibroin hydrogel exhibits a shear modulus of, e.g., at least 1 MPa, at least 10 MPa, at least 20 MPa, at least 30 MPa, at least 40 MPa, at least 50 MPa, at least 60 MPa, at least 70 MPa, at least 80 MPa, at least 90 MPa, at least 100 MPa, at least 200 MPa, at least 300 MPa, at least 400 MPa, at least 500 MPa, at least 750 MPa, at least 1 GPa, at least 5 GPa, at least 10 GPa, at least 15 GPa, at least 20 GPa, at least 25 GPa, or at least 30 GPa In yet other aspects of this embodiment, a silk fibroin hydrogel exhibits a shear modulus of, e.g., about 1 MPa to about 30 MPa, about 10 MPa to about 50 MPa, about 25 MPa to about 75 MPa, about 50 MPa to about 100 MPa, about 100 MPa to about 300 MPa, about 200 MPa to about 400 MPa, about 300 MPa to about 500 MPa, about 100 MPa to about 500 MPa, about 250 MPa to about 750 MPa, about 500 MPa to about 1 GPa, about 1 GPa to about 30 GPa, about 10 GPa to about 30 GPa.

In another embodiment, a silk fibroin hydrogel exhibits a bulk modulus. In aspects of this embodiment, a silk fibroin hydrogel exhibits exhibits a bulk modulus of, e.g., about 5 GPa, about 6 GPa, about 7 GPa, about 8 GPa, about 9 GPa, about 10 GPa, about 15 GPa, about 20 GPa, about 25 GPa, about 30 GPa, about 35 GPa, about 40 GPa, about 45 GPa, about 50 GPa, about 60 GPa, about 70 GPa, about 80 GPa, about 90 GPa, about 100 GPa. In other aspects of this embodiment, a silk fibroin hydrogel exhibits exhibits a bulk modulus of, e.g., at least 5 GPa, at least 6 GPa, at least 7 GPa, at least 8 GPa, at least 9 GPa, at least 10 GPa, at least 15 GPa, at least 20 GPa, at least 25 GPa, at least 30 GPa, at least 35 GPa, at least 40 GPa, at least 45 GPa, at least 50 GPa, at least 60 GPa, at least 70 GPa, at least 80 GPa, at least 90 GPa, at least 100 GPa. In yet other aspects of this embodiment, a silk fibroin hydrogel exhibits exhibits a bulk modulus of, e.g., about 5 GPa to about 50 GPa, about 5 GPa to about 100 GPa, about 10 GPa to about 50 GPa, about 10 GPa to about 100 GPa, or about 50 GPa to about 100 GPa.

A silk fibroin hydrogel exhibits high tensile strength. Tensile strength has three different definitional points of stress maxima. Yield strength refers to the stress at which material strain changes from elastic deformation to plastic deformation, causing it to deform permanently. Ultimate strength refers to the maximum stress a material can withstand when subjected to tension, compression or shearing. It is the maximum stress on the stress-strain curve. Breaking strength refers to the stress coordinate on the stress-strain curve at the point of rupture, or when the material pulls apart.

In another embodiment, a silk fibroin hydrogel exhibits high yield strength relative to other polymer classes. In aspects of this embodiment, an elastomer matrix defining an array of interconnected pores exhibits a yield strength of, e.g., about 0.1 MPa, about 0.5 MPa, about 1 MPa, about 5 MPa, about 10 MPa, about 20 MPa, about 30 MPa, about 40 MPa, about 50 MPa, about 60 MPa, about 70 MPa, about 80 MPa, about 90 MPa, about 100 MPa, about 200 MPa, about 300 MPa, about 400 MPa, about 500 MPa. In other aspects of this embodiment, a silk fibroin hydrogel exhibits a yield strength of, e.g., at least 0.1 MPa, at least 0.5 MPa, at least 1 MPa, at least 5 MPa, at least 10 MPa, at least 20 MPa, at least 30 MPa, at least 40 MPa, at least 50 MPa, at least 60 MPa, at least 70 MPa, at least 80 MPa, at least 90 MPa, at least 100 MPa, at least 200 MPa, at least 300 MPa, at least 400 MPa, at least 500 MPa. In yet other aspects of this embodiment, a silk fibroin hydrogel exhibits a yield strength of, e.g., at most 1 MPa, at most 5 MPa, at most 10 MPa, at most 20 MPa, at most 30 MPa, at most 40 MPa, at most 50 MPa, at most 60 MPa, at most 70 MPa, at most 80 MPa, at most 90 MPa, at most 100 MPa, at most 200 MPa, at most 300 MPa, at most 400 MPa, at most 500 MPa, at most 600 MPa, at most 700 MPa, at most 800 MPa, at most 900 MPa, at most 1000 MPa, at most 1500 MPa, or at most 2000 MPa. In still other aspects of this embodiment, a silk fibroin hydrogel exhibits a yield strength of, e.g., about 1 MPa to about 50 MPa, about 1 MPa to about 60 MPa, about 1 MPa to about 70 MPa, about 1 MPa to about 80 MPa, about 1 MPa to about 90 MPa, about 1 MPa to about 100 MPa, about 10 MPa to about 50 MPa, about 10 MPa to about 60 MPa, about 10 MPa to about 70 MPa, about 10 MPa to about 80 MPa, about 10 MPa to about 90 MPa, about 10 MPa to about 100 MPa, about 10 MPa to about 200 MPa, about 10 MPa to about 300 MPa, or about 100 MPa to about 300 MPa.

In another embodiment, a silk fibroin hydrogel exhibits high ultimate strength. In aspects of this embodiment, a silk fibroin hydrogel exhibits an ultimate strength of, e.g., about 0.1 MPa, about 0.5 MPa, about 1 MPa, about 5 MPa, about 10 MPa, about 20 MPa, about 30 MPa, about 40 MPa, about 50 MPa, about 60 MPa, about 70 MPa, about 80 MPa, about 90 MPa, about 100 MPa, about 200 MPa, about 300 MPa, about 400 MPa, about 500 MPa. In other aspects of this embodiment, a silk fibroin hydrogel exhibits an ultimate strength of, e.g., at least 0.1 MPa, at least 0.5 MPa, at least 1 MPa, at least 5 MPa, at least 10 MPa, at least 20 MPa, at least 30 MPa, at least 40 MPa, at least 50 MPa, at least 60 MPa, at least 70 MPa, at least 80 MPa, at least 90 MPa, at least 100 MPa, at least 200 MPa, at least 300 MPa, at least 400 MPa, at least 500 MPa. In yet other aspects of this embodiment, a silk fibroin hydrogel exhibits an ultimate strength of, e.g., at most 1 MPa, at most 5 MPa, at most 10 MPa, at most 20 MPa, at most 30 MPa, at most 40 MPa, at most 50 MPa, at most 60 MPa, at most 70 MPa, at most 80 MPa, at most 90 MPa, at most 100 MPa, at most 200 MPa, at most 300 MPa, at most 400 MPa, at most 500 MPa, at most 600 MPa, at most 700 MPa, at most 800 MPa, at most 900 MPa, at most 1000 MPa, at most 1500 MPa, or at most 2000 MPa. In still other aspects of this embodiment, a silk fibroin hydrogel exhibits an ultimate strength of, e.g., about 1 MPa to about 50 MPa, about 1 MPa to about 60 MPa, about 1 MPa to about 70 MPa, about 1 MPa to about 80 MPa, about 1 MPa to about 90 MPa, about 1 MPa to about 100 MPa, about 10 MPa to about 50 MPa, about 10 MPa to about 60 MPa, about 10 MPa to about 70 MPa, about 10 MPa to about 80 MPa, about 10 MPa to about 90 MPa, about 10 MPa to about 100 MPa, about 10 MPa to about 200 MPa, about 10 MPa to about 300 MPa, or about 100 MPa to about 300 MPa.

In another embodiment, a silk fibroin hydrogel exhibits high breaking strength. In aspects of this embodiment, a silk fibroin hydrogel exhibits a breaking strength of, e.g., about 0.1 MPa, about 0.5 MPa, about 1 MPa, about 5 MPa, about 10 MPa, about 20 MPa, about 30 MPa, about 40 MPa, about 50 MPa, about 60 MPa, about 70 MPa, about 80 MPa, about 90 MPa, about 100 MPa, about 200 MPa, about 300 MPa, about 400 MPa, about 500 MPa. In other aspects of this embodiment, a silk fibroin hydrogel exhibits a breaking strength of, e.g., at least 0.1 MPa, at least 0.5 MPa, at least 1 MPa, at least 5 MPa, at least 10 MPa, at least 20 MPa, at least 30 MPa, at least 40 MPa, at least 50 MPa, at least 60 MPa, at least 70 MPa, at least 80 MPa, at least 90 MPa, at least 100 MPa, at least 200 MPa, at least 300 MPa, at least 400 MPa, at least 500 MPa. In yet other aspects of this embodiment, a silk fibroin hydrogel exhibits a breaking strength of, e.g., at most 1 MPa, at most 5 MPa, at most 10 MPa, at most 20 MPa, at most 30 MPa, at most 40 MPa, at most 50 MPa, at most 60 MPa, at most 70 MPa, at most 80 MPa, at most 90 MPa, at most 100 MPa, at most 200 MPa, at most 300 MPa, at most 400 MPa, at most 500 MPa, at most 600 MPa, at most 700 MPa, at most 800 MPa, at most 900 MPa, at most 1000 MPa, at most 1500

MPa, or at most 2000 MPa. In still other aspects of this embodiment, a silk fibroin hydrogel exhibits a breaking strength of, e.g., about 1 MPa to about 50 MPa, about 1 MPa to about 60 MPa, about 1 MPa to about 70 MPa, about 1 MPa to about 80 MPa, about 1 MPa to about 90 MPa, about 1 MPa to about 100 MPa, about 10 MPa to about 50 MPa, about 10 MPa to about 60 MPa, about 10 MPa to about 70 MPa, about 10 MPa to about 80 MPa, about 10 MPa to about 90 MPa, about 10 MPa to about 100 MPa, about 10 MPa to about 200 MPa, about 10 MPa to about 300 MPa, or about 100 MPa to about 300 MPa.

Aspects of the present specification provide, in part, a silk fibroin hydrogel having a transparency and/or translucency. Transparency (also called pellucidity or diaphaneity) is the physical property of allowing light to pass through a material, whereas translucency (also called translucence or translucidity) only allows light to pass through diffusely. The opposite property is opacity. Transparent materials are clear, while translucent ones cannot be seen through clearly. The silk fibroin hydrogels disclosed in the present specification may, or may not, exhibit optical properties such as transparency and translucency. In certain cases, e.g., superficial line filling, it would be an advantage to have an opaque hydrogel. In other cases such as development of a lens or a "humor" for filling the eye, it would be an advantage to have a translucent hydrogel. These properties could be modified by affecting the structural distribution of the hydrogel material. Factors used to control a hydrogels optical properties include, without limitation, silk fibroin concentration, gel crystallinity, and hydrogel homogeneity.

When light encounters a material, it can interact with it in several different ways. These interactions depend on the nature of the light (its wavelength, frequency, energy, etc.) and the nature of the material. Light waves interact with an object by some combination of reflection, and transmittance with refraction. As such, an optically transparent material allows much of the light that falls on it to be transmitted, with little light being reflected. Materials which do not allow the transmission of light are called optically opaque or simply opaque.

In an embodiment, a silk fibroin hydrogel is optically transparent. In aspects of this embodiment, a silk fibroin hydrogel transmits, e.g., about 75% of the light, about 80% of the light, about 85% of the light, about 90% of the light, about 95% of the light, or about 100% of the light. In other aspects of this embodiment, a silk fibroin hydrogel transmits, e.g., at least 75% of the light, at least 80% of the light, at least 85% of the light, at least 90% of the light, or at least 95% of the light. In yet other aspects of this embodiment, a silk fibroin hydrogel transmits, e.g., about 75% to about 100% of the light, about 80% to about 100% of the light, about 85% to about 100% of the light, about 90% to about 100% of the light, or about 95% to about 100% of the light.

In another embodiment, a silk fibroin hydrogel is optically opaque. In aspects of this embodiment, a silk fibroin hydrogel transmits, e.g., about 5% of the light, about 10% of the light, about 15% of the light, about 20% of the light, about 25% of the light, about 30% of the light, about 35% of the light, about 40% of the light, about 45% of the light, about 50% of the light, about 55% of the light, about 60% of the light, about 65% of the light, or about 70% of the light. In other aspects of this embodiment, a silk fibroin hydrogel transmits, e.g., at most 5% of the light, at most 10% of the light, at most 15% of the light, at most 20% of the light, at most 25% of the light, at most 30% of the light, at most 35% of the light, at most 40% of the light, at most 45% of the light, at most 50% of the light, at most 55% of the light, at most 60% of the light, at most 65% of the light, at most 70% of the light, or at most 75% of the light. In other aspects of this embodiment, a silk fibroin hydrogel transmits, e.g., about 5% to about 15%, about 5% to about 20%, about 5% to about 25%, about 5% to about 30%, about 5% to about 35%, about 5% to about 40%, about 5% to about 45%, about 5% to about 50%, about 5% to about 55%, about 5% to about 60%, about 5% to about 65%, about 5% to about 70%, about 5% to about 75%, about 15% to about 20%, about 15% to about 25%, about 15% to about 30%, about 15% to about 35%, about 15% to about 40%, about 15% to about 45%, about 15% to about 50%, about 15% to about 55%, about 15% to about 60%, about 15% to about 65%, about 15% to about 70%, about 15% to about 75%, about 25% to about 35%, about 25% to about 40%, about 25% to about 45%, about 25% to about 50%, about 25% to about 55%, about 25% to about 60%, about 25% to about 65%, about 25% to about 70%, or about 25% to about 75%.

In an embodiment, a silk fibroin hydrogel is optically translucent. In aspects of this embodiment, a silk fibroin hydrogel diffusely transmits, e.g., about 75% of the light, about 80% of the light, about 85% of the light, about 90% of the light, about 95% of the light, or about 100% of the light. In other aspects of this embodiment, a silk fibroin hydrogel diffusely transmits, e.g., at least 75% of the light, at least 80% of the light, at least 85% of the light, at least 90% of the light, or at least 95% of the light. In yet other aspects of this embodiment, a silk fibroin hydrogel diffusely transmits, e.g., about 75% to about 100% of the light, about 80% to about 100% of the light, about 85% to about 100% of the light, about 90% to about 100% of the light, or about 95% to about 100% of the light.

To remove enhancer species from the formed gel and become a more complete hydrogel, the formed gel may be leeched against water, for example under ambient temperature and pressure conditions for three days with five changes of water. The gel may be leeched against ultra-pure water of a volume at least 100-times that of the gel. More specifically, for example, the gels may be placed in a bulk of purified water and the rinse changed at hours 12, 24 and 48 with 15 mL gel per 1.5 L water. The number of rinses and volume ratios involved may be altered so long as the resultant hydrogel is substantially free of residual gelation enhancer.

The hydrogel may then be further processed for cleaning, loading, and sterilizing for use. For example, the hydrogel may be pulverized and mixed with saline solution. In a particular example, the gel may be milled to a particle size from about 10 μm to about 1000 μm in diameter, such as 15 μm to 30 μm. Saline is then added to the hydrogel as a carrier phase by first determining the volume of a bulk of hydrogel, then vigorously pulverizing the hydrogel while incorporating an appropriate volume of saline to the hydrogel to achieve a desired carrier to hydrogel ratio. For example, hydrogel milling may be accomplished in one example by means of a forced sieving of bulk hydrogel material through a series of stainless steel cloth sieves of decreasing pore sizes. In another example, hydrogel may be loaded into a syringe and pulverized with a spatula to a fine paste with saline. The present hydrogel formulations are preferably sterile.

In an aspect of this embodiment, a hydrogel formulation comprises a gel phase including hydrogel particles having a particle size from about 5 μm$^2$ to about 1000 μm$^2$ in cross-sectional area. In aspects of this embodiment, a hydrogel formulation comprises a gel phase including hydrogel particles having a mean particle size of, e.g., about 5 μm$^2$, about 10 μm$^2$, about 15 μm$^2$, about 20 μm$^2$, about 25 μm$^2$, about 30 μm$^2$, about 35 μm$^2$, about 40 μm$^2$, about 45 μm$^2$, about 50 μm$^2$, about 60 μm$^2$, about 70 μm$^2$, about 80 μm$^2$, about 90 μm$^2$, about 100 μm$^2$, about 200 μm$^2$, about 300 μm$^2$, about 400 μm², about 500 μm², about 600 μm², about 700 μm², about 800 μm², about 900 μm², or about 1000 μm² in cross-sectional area. In other aspects of the embodiment, a hydrogel formulation comprises a gel phase including hydrogel particles having a mean particle size of, e.g., at least 5 μm², at least 10 μm², at least 15 μm², at least 20 μm², at least 25 μm², at least 30 μm², at least 35 μm², at least 40 μm², at least 45 μm², at least 50 μm², at least 60 μm², at least 70 μm², at least 80 μm², at least 90 μm², at least 100 μm², at least 200 μm², at least 300 μm², at least 400 μm², at least 500 μm², at least 600 μm², at least 700 μm², at least 800 μm², at least 900 μm², or at least 1000 μm² in cross-sectional area. In yet other aspects of this embodiment, a hydrogel formulation comprises a gel phase including hydrogel particles having a mean particle size of, e.g., at most 5 μm², at most 10 μm², at most 15 μm², at most 20 μm², at most 25 μm², at most 30 μm², at most 35 μm², at most 40 μm², at most 45 μm², at most 50 μm², at most 60 μm², at most 70 μm², at most 80 μm², at most 90 μm², at most 100 μm², at most 200 μm², at most 300 μm², at most 400 μm², at most 500 μm², at most 600 μm², at most 700 μm², at most 800 μm², at most 900 μm², or at most 1000 μm² in cross-sectional area. In still other aspects of the embodiment, a hydrogel formulation comprises a gel phase including hydrogel particles having a mean particle size of, e.g., about 5 μm² to about 50 μm², about 25 μm² to about 75 μm², about 50 μm² to about 100 μm², about 100 μm² to about 300 μm², about 200 μm² to about 400 μm², about 300 μm² to about 500 μm², about 400 μm² to about 600 μm², about 500 μm² to about 700 μm², about 600 μm² to about 800 μm², about 700 μm² to about 900 μm², about 800 μm² to about 1000 μm², about 100 μm² to about 400 μm², about 300 μm² to about 600 μm², about 500 μm² to about 800 μm², or about 700 μm² to about 1000 μm², in cross-sectional area.

In aspects of this embodiment, a hydrogel formulation comprises a gel phase including hydrogel particles having a particle size of, e.g., at least 5 μm², at least 10 μm², at least 15 μm², at least 20 μm², at least 25 μm², at least 30 μm², at least 35 μm², at least 40 μm², at least 45 μm², at least 50 μm², at least 60 μm², at least 70 μm², at least 80 μm², at least 90 μm², at least 100 μm², at least 200 μm², at least 300 μm², at least 400 μm², at least 500 μm², at least 600 μm², at least 700 μm², at least 800 μm², at least 900 μm², or at least 1000 μm² in cross-sectional area. In other aspects of this embodiment, a hydrogel formulation comprises a gel phase including hydrogel particles having a particle size of, e.g., at most 5 μm², at most 10 μm², at most 15 μm², at most 20 μm², at most 25 μm², at most 30 μm², at most 35 μm², at most 40 μm², at most 45 μm², at most 50 μm², at most 60 μm², at most 70 μm², at most 80 μm², at most 90 μm², at most 100 μm², at most 200 μm², at most 300 μm², at most 400 μm², at most 500 μm², at most 600 μm², at most 700 μm², at most 800 μm², at most 900 μm², or at most 1000 μm² in cross-sectional area. In yet other aspects of the embodiment, a hydrogel formulation comprises a gel phase including hydrogel particles having a particle size of, e.g., about 5 μm² to about 50 μm², about 25 μm² to about 75 μm², about 50 μm² to about 100 μm², about 100 μm² to about 300 μm², about 200 μm² to about 400 μm², about 300 μm² to about 500 μm², about 400 μm² to about 600 μm², about 500 μm² to about 700 μm², about 600 μm² to about 800 μm², about 700 μm² to about 900 μm², about 800 μm² to about 1000 μm², about 100 μm² to about 400 μm², about 300 μm² to about 600 μm², about 500 μm² to about 800 μm², or about 700 μm² to about 1000 μm², in cross-sectional area.

Aspects of the present hydrogel formulations provide, in part, a carrier phase. A carrier phase is advantageously a physiologically-acceptable carrier phase and may include one or more conventional excipients useful in pharmaceutical compositions. As used herein, the term "a physiologically-acceptable carrier phase" refers to a carrier phase in accord with, or characteristic of, the normal functioning of a living organism. As such, administration of a hydrogel formulation disclosed in the present composition comprises a carrier phase that has substantially no long term or permanent detrimental effect when administered to mammal. The present compositions preferably include a carrier phase where a major of the volume is water or saline. However, other useful carrier phases include any physiologically tolerable buffer, serum or other protein solutions.

The volume of carrier phase per volume of gel phase may be increased or decreased in a range between 0% to 100% depending upon the desired physical properties of the resultant formulation including dose delivery, viscosity, injectability, and desired in vivo behavioral characteristics. This formulation is then mixed until achieving a "uniform" hydrogel formulation consistency which may be termed an emulsion or suspension. More specifically, for example, a hydrogel may be passed through an 18 g needle several times to decrease particle size, injecting back and forth between a pair of syringes, then this procedure repeated with 22 g needles affixed to 1 mL syringes. Advantages derived from adding a carrier phase to the gel phase include decreased viscosity in the extracellular in vivo microenvironment; release of local mechanical stress loading after hydrogel formulation administration; and improved ionic composition resulting in improved biocompatibility.

The silk hydrogel disclosed in the present specification may be formulated using material processing constraints such as silk concentration and saline concentration to tailor material longevity in vivo. In one example, a silk gel might be tailored for a persistence of five weeks to six weeks in vivo by using a 1%-3% (w/v) silk gel with 25%-50% (v/v) saline carrier. In another example, a silk gel might be tailored for a persistence of two months to three months in vivo by using a 3%-5% (w/v) silk gel with 20%-40% (v/v) saline. In another example, a silk gel might be tailored for a persistence of 5-6 months by using 4-6% (w/v) silk gel with 20-40% (v/v) saline. In another example, a silk gel might be tailored for a persistence of 7-10 months by using a 6-8% (w/v) silk gel with 20-30% (v/v) saline. The persistence of these materials might also be increased or decreased by increasing or decreasing particle size respectively.

Gel emulsion saline content and gel silk concentration could be used to modify the mechanical profile of the silk gel materials for particular applications. For example, a gel emulsion of about 1% (w/v) to about 5% (w/v) silk gel concentration with 5%-95% lubricant (e.g., 5%-95% (w/v) saline/PBS) may be useful as a dermal filler, bulking agent, camouflage agent, intramuscular or sub-Q filler, or pharmaceutical delivery vector. A gel emulsion of, for example, about 5% (w/v) to about 8% (w/v) silk gel concentration with 0% to about 30% lubricant fluid may be useful in bone defects or cartilage defects.

Aspects of the present specification provide, in part, a hydrogel formulation disclosed in the present specification exhibiting a dynamic viscosity. Viscosity is resistance of a fluid to shear or flow caused by either shear stress or tensile stress. Viscosity describes a fluid's internal resistance to flow caused by intermolecular friction exerted when layers of fluids attempt to slide by one another and may be thought of as a measure of fluid friction. The less viscous the fluid, the greater its ease of movement (fluidity).

Viscosity can be defined in two ways; dynamic viscosity ($\mu$, although $\eta$ is sometimes used) or kinematic viscosity ($v$). Dynamic viscosity, also known as absolute or complex viscosity, is the tangential force per unit area required to move one horizontal plane with respect to the other at unit velocity when maintained a unit distance apart by the fluid. The SI physical unit of dynamic viscosity is the Pascal-second (Pa·s), which is identical to N·m−2·s. Dynamic viscosity can be expressed as $\tau=\mu dvx/dz$, where $\tau$=shearing stress, $\mu$=dynamic viscosity, and dvx/dz is the velocity gradient over time. For example, if a fluid with a viscosity of one Pa·s is placed between two plates, and one plate is pushed sideways with a shear stress of one Pascal, it moves a distance equal to the thickness of the layer between the plates in one second. Dynamic viscosity symbolize by is also used, is measured with various types of rheometers, devices used to measure the way in which a liquid, suspension or slurry flows in response to applied forces.

Kinematic viscosity (v) is the ratio of dynamic viscosity to density, a quantity in which no force is involved and is defined as follows: $v=\mu/\rho$, where $\mu$ is the dynamic viscosity $\rho$ is density with the SI unit of $kg/m^3$. Kinematic viscosity is usually measured by a glass capillary viscometer as has an SI unit of $m^2/s$.

The viscosity of a fluid is highly temperature dependent and for either dynamic or kinematic viscosity to be meaningful, the reference temperature must be quoted. For the viscosity values disclosed in the present specification, a dynamic viscosity is measured at 1 Pa with a cone/plane geometry 2°/40 cm and a temperature of 20° C. Examples of the dynamic viscosity of various fluids at 20° C. is as follows: water is about $1.0\times10^{-3}$ Pa·s, blood is about $3-4\times10^{-3}$ Pa·s, vegetable oil is about $60-85\times10^{-3}$ Pa·s, motor oil SE 30 is about 0.2 Pa·s, glycerin is about 1.4 Pa·s, maple syrup is about 2-3 Pa·s, honey is about 10 Pa·s, chocolate syrup is about 10-25 Pa·s, peanut butter is about 150-250 Pa·s, lard is about 1,000 Pa·s, vegetable shortening is about 1,200 Pa·s, and tar is about 30,000 Pa·s.

Thus, in an embodiment, a hydrogel formulation comprising a gel phase, the gel phase including hydrogel particles comprising a substantially sericin-depleted silk fibroin and a carrier phase exhibits a dynamic viscosity. In aspects of this embodiment, a hydrogel composition comprising a gel phase, the gel phase including hydrogel particles comprising a substantially sericin-depleted silk fibroin and a carrier phase exhibits a dynamic viscosity of, e.g., about 10 Pa·s, about 20 Pa·s, about 30 Pa·s, about 40 Pa·s, about 50 Pa·s, about 60 Pa·s, about 70 Pa·s, about 80 Pa·s, about 90 Pa·s, about 100 Pa·s, about 125 Pa·s, about 150 Pa·s, about 175 Pa·s, about 200 Pa·s, about 225 Pa·s, about 250 Pa·s, about 275 Pa·s, about 300 Pa·s, about 400 Pa·s, about 500 Pa·s, about 600 Pa·s, about 700 Pa·s, about 750 Pa·s, about 800 Pa·s, about 900 Pa·s, about 1,000 Pa·s, about 1,100 Pa·s, or about 1,200 Pa·s. In other aspects of this embodiment, a hydrogel formulation comprising a gel phase, the gel phase including hydrogel particles comprising a substantially sericin-depleted silk fibroin and a carrier phase exhibits a dynamic viscosity of, e.g., at most 10 Pa·s, at most 20 Pa·s, at most 30 Pa·s, at most 40 Pa·s, at most 50 Pa·s, at most 60 Pa·s, at most 70 Pa·s, at most 80 Pa·s, at most 90 Pa·s, at most 100 Pa·s, at most 125 Pa·s, at most 150 Pa·s, at most 175 Pa·s, at most 200 Pa·s, at most 225 Pa·s, at most 250 Pa·s, at most 275 Pa·s, at most 300 Pa·s, at most 400 Pa·s, at most 500 Pa·s, at most 600 Pa·s, at most 700 Pa·s, at most 750 Pa·s, at most 800 Pa·s, at most 900 Pa·s, or at most 1000 Pa·s. In yet other aspects of this embodiment, a hydrogel formulation comprising a gel phase, the gel phase including hydrogel particles comprising a substantially sericin-depleted silk fibroin and a carrier phase exhibits a dynamic viscosity of, e.g., about 10 Pa·s to about 100 Pa·s, about 10 Pa·s to about 150 Pa·s, about 10 Pa·s to about 250 Pa·s, about 50 Pa·s to about 100 Pa·s, about 50 Pa·s to about 150 Pa·s, about 50 Pa·s to about 250 Pa·s, about 100 Pa·s to about 500 Pa·s, about 100 Pa·s to about 750 Pa·s, about 100 Pa·s to about 1,000 Pa·s, about 100 Pa·s to about 1,200 Pa·s, about 300 Pa·s to about 500 Pa·s, about 300 Pa·s to about 750 Pa·s, about 300 Pa·s to about 1,000 Pa·s, or about 300 Pa·s to about 1,200 Pa·s.

Aspects of the present specification provide, in part, a hydrogel formulation disclosed in the present specification that is injectable. As used herein, the term "injectable" refers to a hydrogel formulation disclosed in the present specification having the properties necessary to administer the composition into a dermal region of an individual using an injection device with a fine needle. As used herein, the term "fine needle" refers to a needle that is 27 gauge or smaller. Injectability of a hydrogel formulation disclosed in the present specification can be accomplished by sizing the hydrogel particles as discussed above.

Thus, in an embodiment, a hydrogel formulation comprises a gel phase, the gel phase including hydrogel particles comprising a substantially sericin-depleted silk fibroin and a carrier phase, wherein the formulation is injectable. In aspect of this embodiment, a hydrogel formulation comprising a gel phase, the gel phase including hydrogel particles comprising a substantially sericin-depleted silk fibroin and a carrier phase is injectable through a fine needle. In other aspects of this embodiment, a hydrogel formulation comprising a gel phase, the gel phase including hydrogel particles comprising a substantially sericin-depleted silk fibroin and a carrier phase is injectable through a needle of, e.g., about 27 gauge, about 30 gauge, or about 32 gauge. In yet other aspects of this embodiment, a hydrogel formulation comprising a gel phase, the gel phase including hydrogel particles comprising a substantially sericin-depleted silk fibroin and a carrier phase is injectable through a needle of, e.g., 27 gauge or smaller, 30 gauge or smaller, or 32 gauge or smaller. In still other aspects of this embodiment, a hydrogel formulation comprising a gel phase, the gel phase including hydrogel particles comprising a substantially sericin-depleted silk fibroin and a carrier phase is injectable through a needle of, e.g., about 27 gauge to about 32 gauge.

In aspects of this embodiment, a hydrogel formulation comprises a gel phase, the gel phase including hydrogel particles comprising a substantially sericin-depleted silk fibroin and a carrier phase can be injected with an extrusion force of about 60 N, about 55 N, about 50 N, about 45 N, about 40 N, about 35 N, or about 30 N. In other aspects of this embodiment, a hydrogel formulation comprising a gel phase, the gel phase including hydrogel particles comprising a substantially sericin-depleted silk fibroin and a carrier phase can be injected with an extrusion force of about 60 N or less, about 55 N or less, about 50 N or less, about 45 N or less, about 40 N or less, about 35 N or less, about 30 N or less, about 25 N or less, about 20 N or less, about 15 N or less, about 10 N or less, or about 5 N or less.

Aspects of the present specification provide, in part, a silk fibroin hydrogel exhibits cohesiveness. Cohesion or cohesive attraction, cohesive force, or compression force is a physical property of a material, caused by the intermolecular attraction between like-molecules within the material that acts to unite the molecules. A silk fibroin hydrogel should be sufficiently cohesive as to remain localized to a site of administration. Additionally, in certain applications, a sufficient cohesiveness is important for a hydrogel to retain its shape, and thus functionality, in the event of mechanical load cycling. As such, in one embodiment, a silk fibroin hydrogel exhibits strong cohesive attraction, on par with water. In another embodiment, a silk fibroin hydrogel exhibits low cohesive attraction. In yet another embodiment, a silk fibroin hydrogel exhibits sufficient cohesive attraction to remain localized to a site of administration. In still another embodiment, a silk fibroin hydrogel exhibits sufficient cohesive attraction to retain its shape. In a further embodiment, a silk fibroin hydrogel exhibits sufficient cohesive attraction to retain its shape and functionality.

In aspects of this embodiment, a silk fibroin hydrogel has a compression force of about 10 grams-force, about 20 grams-force, about 30 grams-force, about 40 grams-force, about 50 grams-force, about 60 grams-force, about 70 grams-force, about 80 grams-force, about 90 grams-force, about 100 grams-force, about 200 grams-force, about 300 grams-force, about 400 grams-force, about 500 grams-force, about 600 grams-force, about 700 grams-force, or about 800 grams-force. In other aspects of this embodiment, a silk fibroin hydrogel has a compression force of at least 500 grams-force, at least 600 grams-force, at least 700 grams-force, at least 800 grams-force, at least 900 grams-force, at least 1000 grams-force, at least 1250 grams-force, at least 1500 grams-force, at least 1750 grams-force, at least 2000 grams-force, at least 2250 grams-force, at least 2500 grams-force, at least 2750 grams-force, or at least 3000 grams-force. In other aspects of this embodiment, a silk fibroin hydrogel has a compression force of at most 10 grams-force, at most 20 grams-force, at most 30 grams-force, at most 40 grams-force, at most 50 grams-force, at most 60 grams-force, at most 70 grams-force, at most 80 grams-force, at most 90 grams-force, at most 100 grams-force, at most 200 grams-force, at most 300 grams-force, at most 400 grams-force, at most 500 grams-force, at most 600 grams-force, at most 700 grams-force, or at most 800 grams-force.

In yet other aspects of this embodiment, a silk fibroin hydrogel has a compression force of about 10 grams-force to about 50 grams-force, about 25 grams-force to about 75 grams-force, about 50 grams-force to about 150 grams-force, about 100 grams-force to about 200 grams-force, about 100 grams-force to about 300 grams-force, about 100 grams-force to about 400 grams-force, about 100 grams-force to about 500 grams-force, about 200 grams-force to about 300 grams-force, about 200 grams-force to about 400 grams-force, about 200 grams-force to about 500 grams-force, about 200 grams-force to about 600 grams-force, about 200 grams-force to about 700 grams-force, about 300 grams-force to about 400 grams-force, about 300 grams-force to about 500 grams-force, about 300 grams-force to about 600 grams-force, about 300 grams-force to about 700 grams-force, about 300 grams-force to about 800 grams-force, about 400 grams-force to about 500, about 400 grams-force to about 600, about 400 grams-force to about 700, about 400 grams-force to about 800, about 500 grams-force to about 600 grams-force, about 500 grams-force to about 700 grams-force, about 500 grams-force to about 800 grams-force, about 600 grams-force to about 700 grams-force, about 600 grams-force to about 800 grams-force, about 700 grams-force to about 800 grams-force, about 1000 grams-force to about 2000 grams-force, about 1000 grams-force to about 3000 grams-force, or about 2000 grams-force to about 3000 grams-force.

Aspects of the present hydrogel formulations provide, in part, a surfactant. As used herein, the term "surfactant" refers to a natural or synthetic amphiphilic compound. A surfactant can be non-ionic, zwitterionic, or ionic. It is envisioned that any surfactant is useful in making a hydrogel formulation disclosed in the present specification, with the proviso that a therapeutically effective amount of the hydrogel formulation is recovered using this surfactant amount. Non-limiting examples of surfactants include polysorbates like polysorbate 20 (TWEEN® 20), polysorbate 40 (TWEEN® 40), polysorbate 60 (TWEEN® 60), polysorbate 61 (TWEEN® 61), polysorbate 65 (TWEEN®65), polysorbate 80 (TWEEN® 80), and polysorbate 81 (TWEEN® 81); poloxamers (polyethylene-polypropylene copolymers), like Poloxamer 124 (PLURONIC® L44), Poloxamer 181 (PLURONIC® L61), Poloxamer 182 (PLURONIC®L62), Poloxamer 184 (PLURONIC® L64), Poloxamer 188 (PLURONIC® F68), Poloxamer 237 (PLURONIC® F87), Poloxamer 338 (PLURONIC® L108), Poloxamer 407 (PLURONIC® F127), polyoxyethyleneglycol dodecyl ethers, like BRIJ® 30, and BRIJ® 35; 2-dodecoxyethanol (LUBROL®-PX); polyoxyethylene octyl phenyl ether (TRITON® X-100); sodium dodecyl sulfate (SDS); 3-[(3-Cholamidopropyhdimethylammonio]-1-propanesulfonate (CHAPS); 3-[(3-Cholamidopropyl)dimethylammonio]-2-hydroxy-1-propanesulfonate (CHAPSO); sucrose monolaurate; and sodium cholate. Other non-limiting examples of surfactant excipients can be found in, e.g., Pharmaceutical Dosage Forms and Drug Delivery Systems (Howard C. Ansel et al., eds., Lippincott Williams & Wilkins Publishers, $7^{th}$ ed. 1999); Remington: The Science and Practice of Pharmacy (Alfonso R. Gennaro ed., Lippincott, Williams & Wilkins, $20^{th}$ ed. 2000); Goodman & Gilman's The Pharmacological Basis of Therapeutics (Joel G. Hardman et al., eds., McGraw-Hill Professional, $10^{th}$ ed. 2001); and Handbook of Pharmaceutical Excipients (Raymond C. Rowe et al., APhA Publications, $4^{th}$ edition 2003), each of which is hereby incorporated by reference in its entirety.

Thus in an embodiment, a hydrogel formulation comprises a surfactant. In aspects of this embodiment, a hydrogel formulation comprises a polysorbate, a poloxamer, a polyoxyethyleneglycol dodecyl ether, 2-dodecoxyethanol, polyoxyethylene octyl phenyl ether, sodium dodecyl sulfate, 3-[(3-Cholamidopropyhdimethylammonio]-1-propanesulfonate, 3-[(3-Cholamidopropyl)dimethylammonio]-2-hydroxy-1-propanesulfonate, sucrose monolaurate; or sodium cholate.

The hydrogel formulations disclosed in the present specification may, or may not, comprise a viscosity inducing component. A viscosity inducing component is present in an effective amount in increasing the viscosity of the hydrogel formulation. A relatively high viscosity may enhance the ability of the present hydrogel formulations maintain the hydrogel particles in substantially uniform suspension in the compositions for prolonged periods of time, for example, for as long as 1 to 2 years, without requiring resuspension processing. The relatively high viscosity of the present compositions may also have an additional benefit of at least assisting the compositions to have the ability to have an increased amount or concentration of the hydrogel particles, while maintaining such hydrogel particles in substantially uniform suspension for prolonged periods of time.

The presently useful viscosity inducing components preferably are shear thinning components in that as the present hydrogel formulations containing such a shear thinning viscosity inducing component is passed or injected through a narrow space, such as 27 gauge needle, under high shear conditions the viscosity of the composition is substantially reduced during such passage. After such passage, the composition regains substantially its pre-injection viscosity so as to maintain the corticosteroid component particles in suspension in the eye.

Any suitable viscosity inducing component, for example, may be employed in accordance with the hydrogel formulations disclosed in the present specification. The viscosity inducing component is present in an amount effective in providing the desired viscosity to the hydrogel formulation. Advantageously, the viscosity inducing component is present in an amount in a range of about 0.5% or about 1.0% to about 5% or about 10% or about 20% (w/v) of the hydrogel formulation. The specific amount of the viscosity inducing component employed depends upon a number of factors including, without limitation, the specific viscosity inducing component being employed, the molecular weight of the viscosity inducing component being employed, the viscosity desired for the present hydrogel formulation being produced and/or used and the like factors, such as shear thinning. The viscosity inducing component is chosen to provide at least one advantage, and preferably multiple advantages, to the present hydrogel formulation, for example, in terms of each of injectability, viscosity, sustainability of the hydrogel particles in suspension, for example, in substantially uniform suspension, for a prolonged period of time without resuspension processing, compatibility with the tissues into which the composition is to be placed and the like advantages. More preferably, the selected viscosity inducing component is effective to provide two or more of the above-noted benefits, and still more preferably to provide all of the above-noted benefits.

The viscosity inducing component preferably comprises a polymeric component and/or at least one viscoelastic agent. Examples of useful viscosity inducing components include, but are not limited to, hyaluronic acid (such as a polymeric hyaluronic acid), carbomers, polyacrylic acid, cellulosic derivatives, polycarbophil, polyvinylpyrrolidone, gelatin, dextrin, polysaccharides, polyacrylamide, polyvinyl alcohol, polyvinyl acetate, derivatives thereof and mixtures and copolymers thereof.

The molecular weight of the presently useful viscosity inducing components may be in a range of about 10,000 Da or less to about 2,000,000 Da or more. In one particularly useful embodiment, the molecular weight of the viscosity inducing component is in a range of about 100,000 Da or about 200,000 Da to about 1,000,000 Da or about 1,500,000 Da. Again, the molecular weight of the viscosity inducing component useful in accordance with the present specification, may vary over a substantial range based on the type of viscosity inducing component employed, and the desired final viscosity of the present composition in question, as well as, possibly one or more other factors.

In one embodiment, a viscosity inducing component is a polymeric hyaluronate component, for example, a metal hyaluronate component, preferably selected from alkali metal hyaluronates, alkaline earth metal hyaluronates and mixtures thereof, and still more preferably selected from sodium hyaluronates, and mixtures thereof. The molecular weight of such hyaluronate component (i.e. a polymeric hyaluronic acid) preferably is in a range of about 50,000 Da or about 100,000 Da to about 1,300,000 Da or about 2,000,000 Da. In one embodiment, the present compositions include a polymeric hyaluronate component in an amount in a range about 0.05% to about 0.5% (w/v). In a further useful embodiment, the hyaluronate component is present in an amount in a range of about 1% to about 4% (w/v) of the composition. In this latter case, the very high polymer viscosity forms a gel that slows particle sedimentation rate to the extent that often no resuspension processing is necessary over the estimated shelf life, for example, at least about 2 years, of the composition. Such a formulation may be marketed in pre-filled syringes since the gel cannot be easily removed by a needle and syringe from a bulk container. Pre-filled syringes have the advantages of convenience for the injector and the safety which results from less handling.

Aspects of the present specification provide, in part, a hydrogel formulation disclosed in the present specification that is a pharmaceutical hydrogel formulation. As used herein, the term "pharmaceutical hydrogel formulation" is synonymous with "pharmaceutically-acceptable hydrogel formulation" and refers to a therapeutically effective concentration of hydrogel formulation, such as, e.g., any of the hydrogel particles or pharmaceutically-acceptable drugs disclosed in the present specification. A pharmaceutical hydrogel formulation is useful for medical and veterinary applications. A pharmaceutical hydrogel formulation may be administered to a individual alone, or in combination with other supplementary active ingredients, agents, drugs or hormones.

Aspects of the present specification provide, in part, a hydrogel formulation disclosed in the present specification that is a pharmaceutical hydrogel formulation comprising a pharmacologically acceptable excipient. As used herein, the term "pharmacologically acceptable excipient" is synonymous with "pharmacological excipient" or "excipient" and refers to any excipient that has substantially no long term or permanent detrimental effect when administered to mammal and encompasses compounds such as, e.g., stabilizing agent, a bulking agent, a cryo-protectant, a lyo-protectant, an additive, a vehicle, a carrier, a diluent, or an auxiliary. An excipient generally is mixed with an active ingredient, or permitted to dilute or enclose the active ingredient and can be a solid, semi-solid, or liquid agent. It is also envisioned that a pharmaceutical hydrogel formulation can include one or more pharmaceutically acceptable excipients that facilitate processing of a hydrogel formulation into pharmaceutically acceptable hydrogel formulation. Insofar as any pharmacologically acceptable excipient is not incompatible with a hydrogel formulation, its use in pharmaceutically acceptable compositions is contemplated. Non-limiting examples of pharmacologically acceptable excipients can be found in, e.g., Pharmaceutical Dosage Forms and Drug Delivery Systems (Howard C. Ansel et al., eds., Lippincott Williams & Wilkins Publishers, $7^{th}$ ed. 1999); Remington: The Science and Practice of Pharmacy (Alfonso R. Gennaro ed., Lippincott, Williams & Wilkins, $20^{th}$ ed. 2000); Goodman & Gilman's The Pharmacological Basis of Therapeutics (Joel G. Hardman et al., eds., McGraw-Hill Professional, $10^{th}$ ed. 2001); and Handbook of Pharmaceutical Excipients (Raymond C. Rowe et al., APhA Publications, $4^{th}$ edition 2003), each of which is hereby incorporated by reference in its entirety.

It is further envisioned that a pharmaceutical hydrogel formulation disclosed in the present specification may optionally include or not include, without limitation, other pharmaceutically acceptable components (or pharmaceutical components), including, without limitation, buffers, preservatives, tonicity adjusters, salts, antioxidants, osmolality adjusting agents, emulsifying agents, wetting agents, sweetening or flavoring agents, and the like.

Pharmaceutically acceptable buffer is any buffer that can be used to prepare a pharmaceutical hydrogel formulation disclosed in the present specification, provided that the resulting preparation is pharmaceutically acceptable. Non-limiting examples of pharmaceutically acceptable buffers include acetate buffers, borate buffers, citrate buffers, neutral buffered salines, phosphate buffers, and phosphate buffered salines. Any concentration of a pharmaceutically acceptable buffer can be useful in formulating a pharmaceutical composition disclosed in the present specification, with the proviso that a therapeutically effective amount of the matrix polymer active ingredient is recovered using this effective concentration of buffer. Non-limiting examples of concentrations of physiologically-acceptable buffers occur within the range of about 0.1 mM to about 900 mM. The pH of pharmaceutically acceptable buffers may be adjusted, provided that the resulting preparation is pharmaceutically acceptable. It is understood that acids or bases can be used to adjust the pH of a pharmaceutical composition as needed. Any buffered pH level can be useful in formulating a pharmaceutical hydrogel formulation, with the proviso that a therapeutically effective amount of the hydrogel formulation is recovered using this effective pH level. Non-limiting examples of physiologically-acceptable pH occur within the range of about pH 5.5 to about pH 8.5.

Pharmaceutically acceptable antioxidants include, without limitation, sodium metabisulfite, sodium thiosulfate, acetylcysteine, butylated hydroxyanisole and butylated hydroxytoluene. Pharmaceutically acceptable preservatives include, without limitation, benzalkonium chloride, chlorobutanol, thimerosal, phenylmercuric acetate, phenylmercuric nitrate, a stabilized oxy chloro composition, such as, e.g., PURITE® and chelants, such as, e.g., DTPA or DTPA-bisamide, calcium DTPA, and CaNaDTPA-bisamide.

Tonicity adjustors useful in a pharmaceutical hydrogel formulation include, without limitation, salts such as, e.g., sodium chloride and potassium chloride; and glycerin. The pharmaceutical hydrogel formulation may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. It is understood that these and other substances known in the art of pharmacology can be included in a pharmaceutical hydrogel formulation disclosed in the present specifciation. Other non-limiting examples of pharmacologically acceptable components can be found in, e.g., Ansel, supra, (1999); Gennaro, supra, (2000); Hardman, supra, (2001); and Rowe, supra, (2003), each of which is hereby incorporated by reference in its entirety.

A hydrogel formulation disclosed in the present specification generally is administered as a pharmaceutical acceptable hydrogel formulation. As used herein, the term "pharmaceutically acceptable" means any molecular entity or composition that does not produce an adverse, allergic or other untoward or unwanted reaction when administered to an individual.

The silk hydrogels as provided for herein may be filled into syringes and sterilized. For example, the pulverized gel saline formulation may be loaded into 1 mL syringes and capped with 26 g needles. These may be stored, e.g., at 4° C., and sterilized, for example, in pouches by exposure to gamma radiation for a dose of 25 kGy. After sterilization, the syringes may be stored until later use under a temperature range from 4° C. to 37° C. until use.

Thus, for example, a formulation may be processed by obtaining an 8% (w/v) silk solution, adding ethanol/23RGD to generate a firm 4%-6% (w/v) silk fibroin hydrogel, allowing this to stand for at least 24 hours, rinsing the gel in water to remove residual free enhancer (both 23RGD and ethanol), adding saline to the gel and homogenizing the suspension, tailoring the suspension viscosity with gel concentration, particle size, and saline content, milling the gel to a desired particle size that makes the gel injectable through a 30 g needle, loading the gel into a syringe, and sterilizing the gel with gamma irradiation.

The silk fibroin hydrogels disclosed in the present specification can be used in a variety of medical uses, including, without limitation fillers for tissue space, templates for tissue reconstruction or regeneration, scaffolds for cells in tissue engineering applications and for disease models, a surface coating to improve medical device function, or as a platform for drug delivery.

In any of the uses described below, silk fibroin gels could be combined with cells for purposes of a biologically enhanced repair. Cells could be collected from a multitude of hosts including but not limited to human autograft tissues, transgenic mammals, or bacterial cultures (possibly for use as a probiotic treatment). More specifically, human cells used could consist of stem cells, osteocytes, fibroblasts, neuronal cells, lipocytes, and assorted immunocytes. These cells would be best added after rinsing of the silk gel material itself. They could be seeded upon the surface of a solid implant material or in the case of comminuted gel injectables, blended into the silk gel particles, carrier solution, or mixture of silk gel particles and carrier solution prior to injection or implantation.

In addition, therapeutic agents, pharmaceuticals, or specific growth factors added to the gel for purposes of improved outcome could be introduced at any or a combination of several points throughout the silk gel production process. These factors could be added to silk solution or the accelerant phase prior to gelation induction, they could be soaked into the gel during the accelerant rinsing process, or they could be coated onto the bulk gel following rinsing. Gels which are milled and make use of a carrier fluid could also have an agent soaked into the gel following milling, coated onto the gel following milling, or introduced into the carrier fluid before or after blending with the gel material.

The silk fibroin hydrogels disclosed in the present specification can be used as tissue space fillers fillers, such as, e.g., a dermal filler. One embodiment the invention provides a dermal filler to provide dermal bulking to improve skin appearance or condition, including, without limitation, rehydrating the skin, providing increased elasticity to the skin, reducing skin roughness, making the skin tauter, reducing or eliminating stretch lines or marks, giving the skin better tone, shine, brightness and/or radiance to reduce paleness, reducing or eliminating wrinkles in the skin, providing wrinkle resistance to the skin, and the like. A dermal filler comprising a silk fibroin hydrogel can be modulation for gel hardness and opacity through alteration of silk concentration and formulatory method. Most likely formulatory strategy would entail casting of a bulk silk gel, about 2% (w/v) to about 6% (w/v) in silk fibroin concentration containing a RGD component in the range of about 0.1 to about 10 moles of RGD per mole of silk in the gel material. This gel would in turn be milled in such a manner as to be injectable through a 26-30 g needle. This milled gel should then be blended with a carrier fluid, saline for example, in order to allow for an appropriate extrusion force of less than 40 N (nominal deliverable injection force for a human hand). Likely carrier content in the case of saline should be on the order of 5% to 50% (v/v). For example, higher amount (>25%) of saline addition may be required for applications to in superficial dermal regions, such as, e.g., reconstructive or cosmetic applications to the facial region of an individual. Additional benefit would be derived from infusion of this carrier fluid or gel with an analgesic or other therapeutic compound. In addition, the silk fibroin gel could be combined with cells for purposes of a biologically enhanced repair.

Aspects of the present specification provide, in part, a method of improving a condition of skin in an individual in need thereof, the method comprising the steps of administering a silk fibroin hydrogel formulation disclosed in the present specification into a dermal region of the individual, wherein the formulation comprises a gel phase, the gel phase including hydrogel particles comprising a substantially sericin-depleted silk fibroin and an amphiphilic peptide; and a carrier phase; and wherein the administration improves the condition.

Aspects of the present specification provide, in part, a method of improving an appearance of skin in an individual in need thereof, the method comprising the steps of administering a silk fibroin hydrogel formulation disclosed in the present specification into a dermal region of the individual, wherein the formulation comprises a gel phase, the gel phase including hydrogel particles comprising a substantially sericin-depleted silk fibroin and an amphiphilic peptide; and a carrier phase; and wherein the administration improves the appearance of the skin.

Aspects of the present invention provide, in part, an appearance of skin. Non-limiting examples of a skin appearance include skin wrinkles, lack of skin tautness, skin stretch line and/or marks, and the like.

Aspects of the present invention provide, in part, improving a skin appearance. Non-limiting examples of improving a skin appearance include reducing or eliminating wrinkles in the skin, making the skin tauter, reducing or eliminating stretch lines or marks, giving the skin better tone, shine, brightness and/or radiance to reduce paleness, and the like.

Aspects of the present invention provide, in part, a condition of skin. Non-limiting examples of a skin condition include dehydration, lack of skin elasticity, roughness, lack of skin tautness, skin stretch line and/or marks, skin paleness, skin wrinkles, and the like.

Aspects of the present invention provide, in part, improving a skin condition. Non-limiting examples of improving a skin condition include rehydrating the skin, providing increased elasticity to the skin, reducing skin roughness, making the skin tauter, reducing or eliminating stretch lines or marks, giving the skin better tone, shine, brightness and/or radiance to reduce paleness, reducing or eliminating wrinkles in the skin, providing wrinkle resistance to the skin, and the like.

Thus, in an embodiment, a method of treating a skin condition comprises the step of administering to an individual suffering from a skin condition a silk fibroin hydrogel formulation wherein the formulation comprises a gel phase, the gel phase including hydrogel particles comprising a substantially sericin-depleted silk fibroin and an amphiphilic peptide; and a carrier phase, and wherein the administration of the composition improves the skin condition, thereby treating the skin condition. In an aspect of this embodiment, a method of treating skin dehydration comprises the step of administering to an individual suffering from skin dehydration a silk fibroin hydrogel formulation wherein the formulation comprises a gel phase, the gel phase including hydrogel particles comprising a substantially sericin-depleted silk fibroin and an amphiphilic peptide; and a carrier phase, and wherein the administration of the composition rehydrates the skin, thereby treating skin dehydration. In another aspect of this embodiment, a method of treating a lack of skin elasticity comprises the step of administering to an individual suffering from a lack of skin elasticity a silk fibroin hydrogel formulation wherein the formulation comprises a gel phase, the gel phase including hydrogel particles comprising a substantially sericin-depleted silk fibroin and an amphiphilic peptide; and a carrier phase, and wherein the administration of the composition increases the elasticity of the skin, thereby treating a lack of skin elasticity. In yet another aspect of this embodiment, a method of treating skin roughness comprises the step of administering to an individual suffering from skin roughness a silk fibroin hydrogel formulation wherein the formulation comprises a gel phase, the gel phase including hydrogel particles comprising a substantially sericin-depleted silk fibroin and an amphiphilic peptide; and a carrier phase, and wherein the administration of the composition decreases skin roughness, thereby treating skin roughness. In still another aspect of this embodiment, a method of treating a lack of skin tautness comprises the step of administering to an individual suffering from a lack of skin tautness a silk fibroin hydrogel formulation wherein the formulation comprises a gel phase, the gel phase including hydrogel particles comprising a substantially sericin-depleted silk fibroin and an amphiphilic peptide; and a carrier phase, and wherein the administration of the composition makes the skin tauter, thereby treating a lack of skin tautness.

In a further aspect of this embodiment, a method of treating a skin stretch line or mark comprises the step of administering to an individual suffering from a skin stretch line or mark a silk fibroin hydrogel formulation wherein the formulation comprises a gel phase, the gel phase including hydrogel particles comprising a substantially sericin-depleted silk fibroin and an amphiphilic peptide; and a carrier phase, and wherein the administration of the composition reduces or eliminates the skin stretch line or mark, thereby treating a skin stretch line or mark. In another aspect of this embodiment, a method of treating skin paleness comprises the step of administering to an individual suffering from skin paleness a silk fibroin hydrogel formulation wherein the formulation comprises a gel phase, the gel phase including hydrogel particles comprising a substantially sericin-depleted silk fibroin and an amphiphilic peptide; and a carrier phase, and wherein the administration of the composition increases skin tone or radiance, thereby treating skin paleness. In another aspect of this embodiment, a method of treating skin wrinkles comprises the step of administering to an individual suffering from skin wrinkles a silk fibroin hydrogel formulation wherein the formulation comprises a gel phase, the gel phase including hydrogel particles comprising a substantially sericin-depleted silk fibroin and an amphiphilic peptide; and a carrier phase, and wherein the administration of the composition reduces or eliminates skin wrinkles, thereby treating skin wrinkles. In yet another aspect of this embodiment, a method of treating skin wrinkles comprises the step of administering to an individual a silk fibroin hydrogel formulation wherein the formulation comprises a gel phase, the gel phase including hydrogel particles comprising a substantially sericin-depleted silk fibroin and an amphiphilic peptide; and a carrier phase, and wherein the administration of the composition makes the skin resistant to skin wrinkles, thereby treating skin wrinkles.

Aspects of the present invention provide, in part, a dermal region. As used herein, the term "dermal region" refers to the region of skin comprising the epidermal-dermal junction and the dermis including the superficial dermis (papillary region) and the deep dermis (reticular region). The skin is composed of three primary layers: the epidermis, which provides waterproofing and serves as a barrier to infection; the dermis, which serves as a location for the appendages of skin; and the hypodermis (subcutaneous adipose layer). The epidermis contains no blood vessels, and is nourished by diffusion from the dermis. The main type of cells which make up the epidermis are keratinocytes, melanocytes, Langerhans cells and Merkels cells.

The dermis is the layer of skin beneath the epidermis that consists of connective tissue and cushions the body from stress and strain. The dermis is tightly connected to the epidermis by a basement membrane. It also harbors many Mechanoreceptor/nerve endings that provide the sense of touch and heat. It contains the hair follicles, sweat glands, sebaceous glands, apocrine glands, lymphatic vessels and blood vessels. The blood vessels in the dermis provide nourishment and waste removal from its own cells as well as from the Stratum basale of the epidermis. The dermis is structurally divided into two areas: a superficial area adjacent to the epidermis, called the papillary region, and a deep thicker area known as the reticular region.

The papillary region is composed of loose areolar connective tissue. It is named for its fingerlike projections called papillae that extend toward the epidermis. The papillae provide the dermis with a "bumpy" surface that interdigitates with the epidermis, strengthening the connection between the two layers of skin. The reticular region lies deep in the papillary region and is usually much thicker. It is composed of dense irregular connective tissue, and receives its name from the dense concentration of collagenous, elastic, and reticular fibers that weave throughout it. These protein fibers give the dermis its properties of strength, extensibility, and elasticity. Also located within the reticular region are the roots of the hair, sebaceous glands, sweat glands, receptors, nails, and blood vessels. Tattoo ink is held in the dermis. Stretch marks from pregnancy are also located in the dermis.

The hypodermis is not part of the skin, and lies below the dermis. Its purpose is to attach the skin to underlying bone and muscle as well as supplying it with blood vessels and nerves. It consists of loose connective tissue and elastin. The main cell types are fibroblasts, macrophages and adipocytes (the hypodermis contains 50% of body fat). Fat serves as padding and insulation for the body.

Aspects of the present invention provide, in part, an individual. As used herein, the term "individual" refers to any mammal including a human being.

Aspects of the present invention provide, in part, administering a silk fibroin hydrogel formulation disclosed in the present specification. As used herein, the term "administering" means any delivery mechanism that provides a silk fibroin hydrogel formulation wherein the formulation comprises a gel phase, the gel phase including hydrogel particles comprising a substantially sericin-depleted silk fibroin and an amphiphilic peptide; and a carrier phase, to an individual that potentially results in a clinically, therapeutically, or experimentally beneficial result. The actual delivery mechanism used to administer a silk fibroin hydrogel formulation disclosed in the present specification to an individual can be determined by a person of ordinary skill in the art by taking into account factors, including, without limitation, the type of skin condition, the location of the skin condition, the cause of the skin condition, the severity of the skin condition, the degree of relief desired, the duration of relief desired, the particular silk fibroin hydrogel formulation used, the rate of excretion of the particular silk fibroin hydrogel formulation used, the pharmacodynamics of the particular silk fibroin hydrogel formulation used, the nature of the other compounds included in the particular silk fibroin hydrogel formulation used, the particular route of administration, the particular characteristics, history and risk factors of the individual, such as, e.g., age, weight, general health and the like, or any combination thereof.

Thus, in an embodiment, a silk fibroin hydrogel formulation wherein the formulation comprises a gel phase, the gel phase including hydrogel particles comprising a substantially sericin-depleted silk fibroin and an amphiphilic peptide; and a carrier phase, is administered to a skin region of an individual. In an aspect of this embodiment, a silk fibroin hydrogel formulation wherein the formulation comprises a gel phase, the gel phase including hydrogel particles comprising a substantially sericin-depleted silk fibroin and an amphiphilic peptide; and a carrier phase, is administered to a skin region of an individual by injection. In another aspect of this embodiment, a silk fibroin hydrogel formulation wherein the formulation comprises a gel phase, the gel phase including hydrogel particles comprising a substantially sericin-depleted silk fibroin and an amphiphilic peptide; and a carrier phase, is administered to a skin region of an individual by injection into a dermal region. In aspects of this embodiment, a silk fibroin hydrogel formulation wherein the formulation comprises a gel phase, the gel phase including hydrogel particles comprising a substantially sericin-depleted silk fibroin and an amphiphilic peptide; and a carrier phase, is administered to a skin region of an individual by injection into, e.g., an epidermal-dermal junction region, a papillary region, a reticular region, or any combination thereof.

In another embodiment, the invention provides a dermal filler to provide dermal bulking to reconstruct or augment a soft tissue body part, such as, e.g., a lip, a breast, a breast part like the nipple, a muscle, or any other soft body part where adipose and/or connective tissue is used to provide shape, insulation, or other biological function. In fillers used for these applications, the silk fibroin concentration and the amount of saline addition to silk fibroin hydrogel may be adjusted to fit the relevant constraints of a given biological environment. For example, a gel for breast augmentation would call for modulation of gel hardness and longevity through alteration of silk concentration and formulatory method. Most likely formulatory strategy would entail casting of a bulk silk gel, about 4% (w/v) to about 8% (w/v) in silk fibroin concentration containing a RGD component in the range of about 0.1 to about 10 moles of RGD per mole of silk in the gel material. Likely carrier content in the case of saline should be on the order of 0% to 25% (v/v). Such formulatory strategies should also consider other factors such as, e.g., defect type, defect size and needs for a specific depth of administration of the filler. The particles size and uniformity of the hydrogels can be controlled so that the tissue implantation can be accomplished through injection. For example, for dermal injection and lip augmentation, a syringe needle sized 26 g-30 g would be used. In applications involving large quantities of filler, e.g., breast reconstruction or augmentation, a larger particle size and a larger bore needle like 23 g-27 g may be used to administer the filer. This milled gel should then be blended with a carrier fluid, saline for example, in order to allow for an appropriate extrusion force of less than 40 N (nominal deliverable injection force for a human hand). Additional benefit would be derived from infusion of this carrier fluid or gel with an analgesic or other therapeutic compound. In addition, a silk fibroin hydrogel formulation disclosed in the present specification can be used to fill an expandable implantable medical device, such as, e.g., an expandable breast implant shell.

Aspects of the present specification provide, in part, a method of soft tissue reconstruction or augmentation, the method comprising the step of administering a silk fibroin hydrogel formulation to a soft tissue region of an individual in need of soft tissue reconstruction or augmentation; wherein the formulation comprises a gel phase, the gel phase including hydrogel particles comprising a substantially sericin-depleted silk fibroin and an amphiphilic peptide; and a carrier phase.

Aspects of the present specification provide, in part, a method of soft tissue reconstruction or augmentation, the method comprising the step of placing an implantable medical device into a soft tissue region of an individual at the desired location; and expanding the device by putting a silk fibroin hydrogel formulation into the device, wherein the formulation comprises a gel phase, the gel phase including hydrogel particles comprising a substantially sericin-depleted silk fibroin and an amphiphilic peptide; and a carrier phase, wherein filling the medical device reconstructs or augments the soft tissue.

Aspects of the present specification provide, in part, a soft tissue. Non-limiting examples of of tissue include a lip, a breast, a breast part like the nipple, a muscle, or any other soft body part where adipose and/or connective tissue is used to provide shape, insulation, or other biological function.

Soft tissue reconstruction is the rebuilding of a soft tissue structure that was severely damaged or lost, e.g., by a dramatic accident or surgical removal. For example, breast reconstruction is the rebuilding of a breast, usually in women. It involves using autologous tissue or prosthetic material to construct a natural-looking breast. Often this includes the reformation of a natural-looking areola and nipple. This procedure involves the use of implants or relocated flaps of the patient's own tissue.

Soft tissue augmentation is the altering of a soft tissue structure usually to improve the cosmetic or aesthetic appearance of the soft tissue. For example, breast augmentation (also known as breast augmentation, breast enlargement, mammoplasty enlargement, augmentation mammoplasty) alters the size and shape of a woman's breasts to improve the cosmetic or aesthetic appearance of the woman.

The silk fibroin hydrogels disclosed in the present specification can be used in conjunction with interventional radiology embolization procedures for blocking abnormal blood (artery) vessels (e.g., for the purpose of stopping bleeding) or organs (to stop the extra function e.g. embolization of the spleen for hypersplenism) including uterine artery embolization for percutaneous treatment of uterine fibroids. Modulation of gel hardness and longevity would be done through alteration of silk concentration and formulatory method. Most likely formulatory strategy would entail casting of a bulk silk gel, about 1% (w/v) to about 4% (w/v) in silk concentration containing a RGD component in the range of about 0.01 to about 3 moles of RGD per mole of silk fibroin in the gel material. This gel would in turn be milled in such a manner as to be injectable through a 26-30 g needle. This milled gel might then be blended with a carrier fluid, saline for example, in order to allow for an appropriate extrusion force of less than 40 N (nominal deliverable injection force for a human hand). Carrier content in the case of saline should be on the order of 0% to about 25% (v/v). Additional benefit would be derived from infusion of this carrier fluid or gel with a therapeutic compound such as a clotting agent. In addition, the silk fibroin gel could be combined with cells for purposes of a biologically enhanced repair.

The silk fibroin hydrogels disclosed in the present specification can be used to repair void space created by spine disk nucleus removal surgery to help maintain the normal distance between the adjacent vertebral bodies. As a further alternative, silk hydrogels with a higher concentration of silk protein (e.g., 20% (w/v)) can be generated in a custom designed mold. The resulting device can be implanted without carrier fluid or milling as a replacement of diseased vertebral disk removed by surgical procedure. For this application, the silk hydrogel can be further chemically or physically cross-linked to gain stronger mechanical properties. In addition, the silk fibroin gel could be combined with cells for purposes of a biologically enhanced repair.

In an aspect of this embodiment it would be desirable to employ a vertebral disc filler comprising a silk concentration of about 4% to about 6% (w/v) silk gel. This material would be either milled to an injectable after casting and blended with 0% to about 20% (v/v) carrier fluid and injected into a ruptured disc during gelation. Appropriate RGD content for this material would be on the order of about 0.0001 to about 0.01 moles of RGD per mole of silk in the gel material or on the order of about 5 to about 100 moles of RGD per mole of silk in the gel. A small RGD component or very large RGD component could both be very useful in discouraging cell proliferation either through denial of binding motifs or through provision of so many as to anchor cells and deny the ability to move and proliferate.

In another aspect of this embodiment it would be desirable to cast a silk gel in an appropriately shaped annular mold for replacement of the disk entirely. This gel would employ a silk concentration of about 6% (w/v) to about 10% (w/v) within the gel material itself. An appropriate RGD content would be on the order of about 0.1 to about 3 moles of RGD per mole of silk to encourage host tissue ingrowth into the material. This device could then be implanted in situ.

In another aspect of this embodiment, it would be desirable to employ a silk gel which is injected into the defective disc and gels in place. This gel would employ a silk concentration of about 4% (w/v) to about 10% (w/v) within the gel material. Accelerant could be mixed with silk solution before, during, or after injection into the site of interest. A low concentration of accelerant would be desirable for this application. Appropriate RGD content for this material would be on the order of about 0.0001 to about 0.01 moles of RGD per mole of silk in the gel material or on the order of about 5 to about 100 moles of RGD per mole of silk in the gel. A small RGD component or very large RGD component could both be very useful in discouraging cell proliferation either through denial of binding motifs or through provision of so many as to anchor cells and deny the ability to move and proliferate The silk fibroin hydrogels disclosed in the present specification can be used to fill up the vitreous cavity to support the eyeball structure and maintain the retina's position. For this application, the implant would comprise low silk fibroin concentration, be highly transparency, and could be modified to be more bio-inert, i.e., inhibit cell ingrowth and proliferation, through further treatment, for example, through high 23RGD dosing. For example, silk fibroin gel used as a filler for the vitreous cavity would entail casting of a bulk silk gel of about 0.5% (w/v) to about 2% (w/v) in silk concentration containing a RGD component in the range of 0.0001 to 1 moles of RGD per mole of silk in the gel material or on the order of 5 to 100 moles of RGD per mole of silk in the gel. A small RGD component or very large RGD component could both be very useful in discouraging cell proliferation either through denial of binding motifs or through provision of so many as to anchor cells and deny the ability to move and proliferate. This gel might be milled to become injectable or could be injectable as a bulk depending up on material hardness, though it should be injectable through a 26-30 g needle with an appropriate extrusion force of less than 40 N. Likely carrier content should be on the order of 0% to about 95% (v/v). Carrier composition could be any biologically or anatomically useful liquid and may consist of saline, hyaluronic acid gel, and host or non-host derived biological fluids.

The silk fibroin hydrogels disclosed in the present specification can be used as templates for tissue reconstruction or regeneration. In general, high concentration silk fibroin hydrogels with strong mechanical properties and elasticity may be generated in a custom designed mold chamber to form in to the desired shape required. In a case where silk gel is used as a template for tissue reconstruction or regeneration, ultimate application of the material should be considered in selecting a formulation. The device can cast and molded or cast and reshaped, then implanted for the tissue reconstruction. In addition, the silk fibroin gel could be combined with cells for purposes of a biologically enhanced repair.

In one embodiment the silk hydrogel can be implanted to the location of cartilage (like menisci or meniscal cartilage) or bone defect. The silk hydrogel device would facilitate cartilage/bone cell ingrowth and proliferation and support collagen matrix deposition thus to improve cartilage/bone repair. In another aspect, prior to implantation donor cartilage cells can be seeded or mixed with silk hydrogel and cultured in vitro to expand cell population and to develop cartilage tissue thus to short the healing time period. For this application, specific growth factors such as TGF-β or bone morphogenic proteins (BMPs) which support cartilage or bone tissue formation, respectively, may be added into silk hydrogel. Silk gels used for replacement of bone or cartilage defect should be cast as a silk concentration of about 6% (w/v) to about 10% (w/v) silk fibroin. The RGD component should be in a range from about 0.01 to about 3 moles of RGD per mole of silk in the gel material. These materials could be cast in a mold and thereby shaped to an appropriate application or could be cast in a generic shape and further refined by the end-user of the material prior to implantation.

In another embodiment, the silk fibroin hydrogels can be used for facial plastic surgery, such as, e.g., nose reconstruction. The formulatory strategy discussed above for repairing a cartilage/bone defect would also be applicable for this application.

The silk fibroin hydrogels disclosed in the present specification can be used as scaffolds to support cell growth for tissue engineering or disease model research applications.

In one aspect, the hydrogel scaffolds comprising cells can be use in methods of promoting wound healing or wound closure, for example, at an incision site. The methods generally comprise implanting a hydrogel, for example a bioerodible or bioresorbable hydrogel as disclosed in the present specification, at the wound or incision site and allowing the wound or incision to heal while the implant is eroded or absorbed in the body and is replaced with the individual's own viable tissue. The methods may further comprise the step of seeding the hydrogel with viable cellular material, either from the individual or from a donor, prior to or during implantation.

In another aspect, the hydrogel scaffolds comprising cells can be use in methods of augmenting or reconstructing the breast of a human being. For example, a method for enhancing support of a conventional breast implant, such as, by enhancing support of the lower pole position of a breast implant. As another example, the method generally comprises the steps of implanting a hydrogel scaffold near or in proximity to a breast implant, for example, a conventional breast implant, and seeding the hydrogel with viable cellular material prior to or during implantation. As yet another example, a hydrogel scaffold is used to partially or completely cover a breast implant to provide a beneficial interface with host tissue and to reduce the potential for malpositioning or capsular contracture.

In yet another aspect, the hydrogel scaffolds comprising cells can be use in methods of providing a beneficial interface between host tissue and a prostheses, for example, a breast implant. In some embodiments, the matrices are structured to be effective to reduce the potential for malpositioning or capsular contracture of breast implants. For example, methods are provided for augmenting or reconstructing a human breast, the methods generally comprising: providing a partial or complete covering of breast implants wherein the partial or complete covering comprises a hydrogel scaffold comprising cells. In some embodiments, the hydrogel is a wrap-like configuration on a conventional silicone or saline filled conventional breast implant. The methods may further comprise the step of seeding the hydrogel with viable cellular material prior to or during implantation.

In still another aspect, the silk fibroin hydrogel scaffolds disclosed in the present specification can be used as the scaffold for cells useful for peripheral nerve repair. Silk hydrogels can be implanted to the location of the nerve defect with or without additional device to aid the connection to the nerve ends. For this approach, specific growth factors such as nerve growth factor (NGF), which supports nerve regeneration may be added. Alternatively, nerve cells may be mixed into silk hydrogel and culture expanded in vitro before implantation. There are two possible formulatory strategies in a case where silk fibroin gel is used as a template for peripheral nerve repair. The first involves use of a softer silk gel of about 0.5 (w/v) to about 3% (w/v) silk either shaped cast as a length of nerve scaffold or else milled to be extrudable as a length of nerve scaffold. This material would be infused with appropriate therapeutic factors according to the methods described above. The second likely formulation of this template would be use of the above described soft gel encased in a sheath or conduit of higher strength silk fibroin gel of about 3 to about 8% silk. This might be generated through a co-casting technique or by filling a cast conduit with an injectable core gel material. In the case of all gels an RGD content of about 0.01 to about 3 moles of RGD per mole of silk would be appropriate. If a carrier fluid were employed, a concentration between 0% and about 25% (v/v) would be most appropriate.

The cells can be seeded upon the surface of a solid implant material comprising a hydrogel disclosed in the present specification using a variety of methods. For example, a hydrogel scaffold can be submersed in an appropriate growth medium for the cells of interest, and then directly exposed to the cells. The cells are allowed to proliferate on the surface and interstices of the hydrogel. The hydrogel is then removed from the growth medium, washed if necessary, and implanted. Alternatively, the cells can be placed in a suitable buffer or liquid growth medium and drawn through a hydrogel scaffold by using vacuum filtration. Cells can also be admixed with a precursor of a hydrogel scaffold, and the hydrogel scaffold can then be constructed around the cells, capturing at least some of the cells within the hydrogel scaffold network. In another embodiment, the cells of interest are dissolved into an appropriate solution (e.g., a growth medium or buffer) and then sprayed onto a hydrogel scaffold while the hydrogel scaffold is being formed by electrospinning. This method is particularly suitable when a highly cellularized matrix is desired. Cells can also be electrosprayed onto a hydrogel scaffold during electrospinning. As presently described, electrospraying involves subjecting a cell-containing solution with an appropriate viscosity and concentration to an electric field sufficient to produce a spray of small charged droplets of solution that contain cells.

In certain cases, a solid hydrogel scaffold can be made as a porous material comprising a hydrogel defined by an interconnected array of pores. The size of the pores comprising an interconnected array of pores should be of a size sufficient to facilitate tissue ingrowth. Such porous hydrogel matrix can be made using standard procedures such as, porogens or other leachable materials. Such materials include, without limitation, salts like sodium chloride, potassium chloride, calcium chloride, sodium tartrate, sodium citrate, and the like; biocompatible mono and disaccharides like glucose, fructose, dextrose, maltose, lactose and sucrose); polysaccharides like starch, alginate, chitosan; and water soluble proteins like gelatin and agarose. Porogens and other leachable materials can be removed by immersing the hydrogel with the leachable material in a solvent in which the particle is soluble for a sufficient amount of time to allow leaching of substantially all of the particles, but which does not dissolve or detrimentally alter the hydrogel. In one embodiment, the hydrogel can be dried after the leaching process is complete at a low temperature and/or vacuum to minimize hydrolysis of the matrix unless accelerated degradation of the matrix is desired. Methods useful for making porogens or other leachable materials as well as methods of making a porous biomaterial that can be modified for use based on the disclosure contained in the present specification are described in, e.g., Ma, Reverse Fabrication of Porous Materials, U.S. Pat. No. 6,673,285; Ma, Reverse Fabrication of Porous Materials, U.S. Patent Publication 2002/0005600; Ratner and Marshall, Novel Porous Materials, U.S. Patent Publication 2008/0075752; Ma, Modified Porous Materials and Method of Forming the Same, U.S. Patent Publication 2008/0213564; Ma, et al., Porous Objects Having Immobilized Encapsulated Biomolecules, U.S. Patent Publication 2008/0317816; Hunter, et al., Soft Tissue Implants and Anti-Scarring Agents, U.S. Patent Publication 2009/0214652; Liu, et al., Porous Materials, Methods of Making and Uses, Ser. No. 61/333,613; and Liu, et al., Porous Materials, Methods of Making and Uses, Ser. No. 61/333, 120; each of which is incorporated by reference in its entirety.

In one embodiment, a solid hydrogel scaffold can be made as a porous material comprising a hydrogel defined by an interconnected array of pores. In aspects of this embodiment, pores comprising the interconnected array of pores have a mean pore diameter in the range of, e.g., about 10 µm to about 1,000 µm, about 200 µm to about 800 µm, about 300 µm to about 700 µm, or about 50 µm to about 200 µm, Alternatively, cells could be blended into a hydrogel formulation comprising silk fibroin hydrogel particles, carrier solution, or mixture of silk fibroin hydrogel particles and carrier solution prior to injection or implantation. Growth factors or other matrix proteins such as collagen, fibronectin can be added into the silk hydrogels to facilitate cell growth, differentiation, tissue formation and functional matrix deposition. Following implantation, the hydrogel or hydrogel particles included in the hydrogel formulations comprising cells can be absorbed into the body over time. This absorption can coincide as infiltrating tissue replaces the hydrogel material. Thus, a hydrogel scaffold can provide a temporary, well-defined substrate for tissue in-growth during wound healing and soft tissue reconstruction or augmentation. The disclosed hydrogel scaffolds comprising cells can also provide immediate strength to an incision site or soft tissue reconstruction or augmentation site.

In an embodiment, a hydrogel scaffold comprising cells is bioerodible or bioresorbable. In aspects of this embodiment, a hydrogel scaffold comprising cells is bioeroded or bioresorbed, e.g., about 10 days, about 20 days, about 30 days, about 40 days, about 50 days, about 60 days, about 70 days, about 80 days, or about 90 days after administration. In other aspects of this embodiment, a hydrogel scaffold comprising cells is bioeroded or bioresorbed, e.g., about 10 days or more, about 20 days or more, about 30 days or more, about 40 days or more, about 50 days or more, about 60 days or more, about 70 days or more, about 80 days or more, or about 90 days or more, after administration. In yet other aspects of this embodiment, a hydrogel scaffold comprising cells is bioeroded or bioresorbed, e.g., about 10 days to about 30 days, about 20 days to about 50 days, about 40 days to about 60 days, about 50 days to about 80 days, or about 60 days to about 90 days after administration.

Aspects of the present specification provide, in part, a cellular component. Cells could be collected from a multitude of hosts including but not limited to human autograft tissues, transgenic mammals, or bacterial cultures (possibly for use as a probiotic treatment). In certain cases, the hydrogel scaffold can comprise human stem cells such as, e.g., mesenchymal stem cells, synovial derived stem cells, embryonic stem cells, adult stem cells, umbilical cord blood cells, umbilical Wharton's jelly cells, osteocytes, fibroblasts, neuronal cells, lipocytes, bone marrow cells, assorted immunocytes, precursor cells derived from adipose tissue, bone marrow derived progenitor cells, peripheral blood progenitor cells, stem cells isolated from adult tissue and genetically transformed cells or combinations of the above cells; or differentiated cells such as, e.g., muscle cells, adipose cells. Cells are best added after rinsing of the silk hydrogel material after gelation. Stem cells can be obtained with minimally invasive procedures from bone marrow, adipose tissue, or other sources in the body, are highly expandable in culture, and can be readily induced to differentiate into adipose tissue-forming cells after exposure to a well-established adipogenic inducing supplement. Alternatively, diseased cells such as cancer cells can be seeded and cultured in silk hydrogels. The seeded silk hydrogel can be used as a model system to study disease mechanism and to evaluate potential solutions to cure the diseases. Cells can be added to a hydrogel and cultured in vitro to grow tissue or added to a hydrogel and implanted into a region of the body. The cells can be seeded on the hydrogel for a short period of time (less than 1 day) just prior to implantation, or cultured for a longer (more than 1 day) period to allow for cell proliferation and extracellular matrix synthesis within the seeded matrix prior to implantation.

When utilized as a source of stem cells, adipose tissue can be obtained by any method known to a person of ordinary skill in the art. For example, adipose tissue can be removed from an individual by suction-assisted lipoplasty, ultrasound-assisted lipoplasty, and excisional lipectomy. In addition, the procedures can include a combination of such procedures. Suction assisted lipoplasty can be desirable to remove the adipose tissue from an individual as it provides a minimally invasive method of collecting tissue with minimal potential for stem cell damage that can be associated with other techniques, such as ultrasound assisted lipoplasty. The adipose tissue should be collected in a manner that preserves the viability of the cellular component and that minimizes the likelihood of contamination of the tissue with potentially infectious organisms, such as bacteria and/or viruses.

For some applications preparation of the active cell population can require depletion of the mature fat-laden adipocyte component of adipose tissue. This is typically achieved by a series of washing and disaggregation steps in which the tissue is first rinsed to reduce the presence of free lipids (released from ruptured adipocytes) and peripheral blood elements (released from blood vessels severed during tissue harvest), and then disaggregated to free intact adipocytes and other cell populations from the connective tissue matrix. Disaggregation can be achieved using any conventional techniques or methods, including mechanical force (mincing or shear forces), enzymatic digestion with single or combinatorial protelolytic enzymes, such as collagenase, trypsin, lipase, liberase H1 and pepsin, or a combination of mechanical and enzymatic methods. For example, the cellular component of the intact tissue fragments can be disaggregated by methods using collagenase-mediated dissociation of adipose tissue, similar to the methods for collecting microvascular endothelial cells in adipose tissue, as known to those of skill in the art. Additional methods using collagenase that can be used are also known to those of skill in the art. Furthermore, methods can employ a combination of enzymes, such as a combination of collagenase and trypsin or a combination of an enzyme, such as trypsin, and mechanical dissociation.

The active cell population (processed lipoaspirate) can then be obtained from the disaggregated tissue fragments by reducing the presence of mature adipocytes. Separation of the cells can be achieved by buoyant density sedimentation, centrifugation, elutriation, differential adherence to and elution from solid phase moieties, antibody-mediated selection, differences in electrical charge; immunomagnetic beads, flourescence activated cell sorting (FACS), or other means.

Following disaggregation the active cell population can be washed/rinsed to remove additives and/or by-products of the disaggregation process (e.g., collagenase and newly-released free lipid). The active cell population could then be concentrated by centrifugation. In one embodiment, the cells are concentrated and the collagenase removed by passing the cell population through a continuous flow spinning membrane system or the like, such as, for example, the system disclosed in U.S. Pat. Nos. 5,034,135; and 5,234,608, which are incorporated by reference herein.

In addition to the foregoing, there are many post-wash methods that can be applied for further purifying the active cell population. These include both positive selection (selecting the target cells), negative selection (selective removal of unwanted cells), or combinations thereof. In another embodiment the cell pellet could be resuspended, layered over (or under) a fluid material formed into a continuous or discontinuous density gradient and placed in a centrifuge for separation of cell populations on the basis of cell density. In a similar embodiment continuous flow approaches such as apheresis and elutriation (with or without counter-current) could be used. Adherence to plastic followed by a short period of cell expansion has also been applied in bone marrow-derived adult stem cell populations. This approach uses culture conditions to preferentially expand one population while other populations are either maintained (and thereby reduced by dilution with the growing selected cells) or lost due to absence of required growth conditions. The active cells that have been concentrated, cultured and/or expanded can be incorporated into disclosed matrices.

In one embodiment, stem cells are harvested, the harvested cells are contacted with an adipogenic medium for a time sufficient to induce differentiation into adipocytes, and the adipocytes are loaded onto a biocompatible matrix which is implanted. In additional embodiments, at least some of the stem cells can be differentiated into adipocytes so that a mixture of both cell types is initially present that changes over time to substantially only adipocytes, with stem cells being present in small to undetectable quantities. Adipose tissue is fabricated in vivo by the stem cells or prepared ex vivo by the stem cells.

The silk fibroin hydrogels disclosed in the present specification can be used for eye lens replacement. As mentioned above in potential application for vitreous cavity liquid, a firm silk hydrogel with high optical transparency would be further modified to become bio-inert, potentially through high RGD dosing. In using silk fibroin gels for a lens replacement, a silk concentration of about 6% (w/v) to about 10% (w/v) would be most appropriate. This material should be cast in a shape appropriate for meeting the requirements of a proper lens. Appropriate RGD content for this formulation would be on the order of about 0.0001 to about 1 moles of RGD per mole of silk fibroin in the gel material or on the order of about 5 to about 100 moles of RGD per mole of silk fibroin in the gel. A small RGD component or very large RGD component could both be very useful in discouraging cell proliferation either through denial of binding motifs or through provision of so many as to anchor cells and deny the ability to move and proliferate.

The silk fibroin hydrogels disclosed in the present specification can be used as a platform for drug delivery. For example, the silk hydrogel can be formed with a pharmaceutical agent either entrained in or bound to the gel and injected, implanted, or delivered orally into the body. For extended or sustained-drug delivery, silk hydrogel can manipulated to be highly resistant to bioresorption and hydrophobic under certain conditions (e.g., very high β-sheet content) which discourages cell/tissue ingrowth. This in turn leads to prolonged gel bioresorption and, by extension, prolonged drug release such as, e.g., sustained drug release or extended drug release. The silk fibroin hydrogel platform can be produced as a gel or as a solid. The pharmaceutically-active drug can be, without limitation, proteins, peptides, steroids, antibiotics, vitamins, simple sugars, genes, transfected or non-transfected cells. To control the drug release profile, the pharmaceutically-active drug can be first mixed with silk solutions then form a hydrogel. This silk hydrogel can then be ground into smaller particles mixed with an additional silk gel phase acting as a carrier either with or without a viscosity inducing component, a surfactant, and/or an included lubricant fluid like saline. The therapeutic-bound silk hydrogel can also be further crosslinked to enhance the stability to extend the release period. In an alternative approach, silk hydrogel can be mixed with other polymers, for examples, hyaluronic acid, to prolong the release of certain growth factors or cytokines and to stabilize the functionality. Furthermore, the silk fibroin hydrogel can serve as the outer coating for coaxial drug delivery systems.

Aspects of a drug delivery platform comprising the silk fibroin hydrogels disclosed in the present specification are sustained release drug delivery platforms. As used herein, the term "sustained release" refers to the release of a pharmaceutically-active drug over a period of about seven days or more. In aspects of this embodiment, a drug delivery platform comprising the silk fibroin hydrogel releases a pharmaceutically-active drug with substantially first order release kinetics over a period of, e.g., about 7 days after administration, about 15 days after administration, about 30 days after administration, about 45 days after administration, about 60 days after administration, about 75 days after administration, or about 90 days after administration. In other aspects of this embodiment, a drug delivery platform comprising the silk fibroin hydrogel releases a pharmaceutically-active drug with substantially first order release kinetics over a period of, e.g., at least 7 days after administration, at least 15 days after administration, at least 30 days after administration, at least 45 days after administration, at least 60 days after administration, at least 75 days after administration, or at least 90 days after administration.

Aspects of a drug delivery platform comprising the silk fibroin hydrogels disclosed in the present specification are extended release drug delivery platforms. As used herein, the term "extended release" refers to the release of a pharmaceutically-active drug over a period of time of less than about seven days. In aspects of this embodiment, a drug delivery platform comprising the silk fibroin hydrogel releases a pharmaceutically-active drug with substantially first order release kinetics over a period of, e.g., about 1 day after administration, about 2 days after administration, about 3 days after administration, about 4 days after administration, about 5 days after administration, or about 6 days after administration. In other aspects of this embodiment, a drug delivery platform comprising the silk fibroin hydrogel releases a pharmaceutically-active drug with substantially first order release kinetics over a period of, e.g., at most 1 day after administration, at most 2 days after administration, at most 3 days after administration, at most 4 days after administration, at most 5 days after administration, or at most 6 days after administration.

Aspects of a drug delivery platform comprising the silk fibroin hydrogels disclosed in the present specification are extended release drug delivery platforms. As used herein, the term "pharmaceutically-active drug" refers to a substance used in the diagnosis, treatment, or prevention of a disease or as a component of a medication.

Aspects of a drug delivery platform comprising the silk fibroin hydrogels disclosed in the present specification may, or may not, further comprise a solubilizing component. The use of such a solubilizing component is advantageous to provide any relatively quick release of the pharmaceutically-active drug into the body for therapeutic effectiveness. Such solubilizing component, of course, should be physiologically-acceptable. In one embodiment of the present drug delivery platform, an effective amount of a solubilizing component is provided to solubilize a minor amount, that is less than 50%, for example in a range of about 1% or about 5% to about 10% or about 20% of the pharmaceutically-active drug. For example, the inclusion of a cyclodextrin component, such as β-cyclodextrin, sulfo-butylether β-cyclodextrin (SBE), other cyclodextrins and the like and mixtures thereof, at about 0.5 to about 5.0% (w/v) solubilizes about 1% to about 10% of the initial dose of a pharmaceutically-active drug. This presolubilized fraction provides a readily bioavailable loading dose, thereby avoiding any delay time in therapeutic effectiveness.

Aspects of a drug delivery platform comprising the silk fibroin hydrogels disclosed in the present specification may, or may not, further comprise a sustained release component. Sustained release components, include, without limitation, polymers (in the form for example of gels and microspheres), such as, e.g., poly(D,L,-lactide) or poly(D,L-lactide co-glycolide), in amounts effective to reduce local diffusion rates and/or corticosteroid particle dissolution rates. The result is a flatter elimination rate profile with a lower $C_{max}$ and a more prolonged therapeutic window, thereby extending the time between required injections for many patients. Any suitable, preferably conditionally acceptable, release component may be employed. The sustained release component is preferably biodegradable or bioabsorbable in the eye so that no residue remains over the long term. The amount of the delayed release component included may very over a relatively wide range depending, for example, on the specific sustained release component is being employed, the specific release profile desired and the like factors. Typical amounts of delayed release components, if any, included in the present compositions are in a range of about 0.05% (w/v) to 0.1% (w/v) to about 0.5% (w/v) or about 1% (w/v) or more (weight of the ingredient in the total volume of the composition) of the composition.

The silk fibroin hydrogels disclosed in the present specification can be used as a surface coating to improve the functionality of medical devices. For example, the silk hydrogel can be formed on the surface of a silk yarn or mesh to improve the biocompatibility of the device. The volume of the silk hydrogel may be gradually replaced by ingrown tissue. This silk hydrogel surface coating may contain pharmaceutical agents such as growth factors to help to realize the desired outcome. For example, PDGF can be added to improve ligament and tendon regeneration, TGF-β can be added to improve cartilage regeneration, and antibiotics can be added to cure or prevent infection at the implantation site. Use of drugs such as local anesthetics, lidocane for example, in conjunction with the silk gel could reduce the pain caused by injections of the material. The device can cast and molded or cast and reshaped, then implanted for the tissue reconstruction. In addition, the silk fibroin gel could be combined with cells for purposes of a biologically enhanced repair.

Silk gel could be employed as a coating in a number of different fashions. Devices could be soaked in silk solution, and then exposed to accelerant in a mold such that the silk gel would be developed in a specific shape according to the mold. In another embodiment, the device could be soaked in silk solution, and then exposed to a bulk of accelerant through a dipping process, yielding a uniform layer of silk gel coating the device. In another embodiment, it would be possible for the device to be soaked in accelerant and then introduced into a bulk of silk solution, again forming a uniform layer of silk gel coating the device. In another embodiment, the device could be dipped into a mixture of gelling silk solution and accelerant. In another embodiment, a gelling mixture of silk solution and accelerant could be added to the device in a mold. In yet another embodiment, the gel components could be cast separately onto the device by, e.g., spraying or knifing, and this application would mix the components, thereby causing gelation. In any of these cases, a therapeutic agent could be added as described previously. Conventional techniques for modifying surface texture could also be applied here such as introduction and dissolution of crystalline salts.

The silk concentration of the coating would be determined based upon the projected need for the device itself. In the case of a hard coating, a silk fibroin concentration of about 6% (w/v) to about 10% (w/v) would be appropriate. In the case of a soft coating, about 2% (w/v) to about 5% (w/v) would be appropriate. The RGD concentration of the coating would be determined based upon the desired biological performance of the device. For general tissue interaction and ingrowth, a concentration of RGD between about 0.1 and about 3 moles of RGD per mole of silk would be appropriate. In cases where a muted host ingrowth profile were desirable, appropriate RGD content would be on the order of about 0.0001 to about 0.01 moles of RGD per mole of silk in the gel material or on the order of about 5 to about 100 moles of RGD per mole of silk in the gel. A small RGD component or very large RGD component could both be very useful in discouraging cell proliferation either through denial of binding motifs or through provision of so many as to anchor cells and deny the ability to move and proliferate.

In one embodiment, the present invention provides a five-amino acid peptide "tail" capable of linking or conjugating a molecule X to a silk molecule or fibroin when the molecule X is attached to the tail. As used herein, the term "linking" or "conjugating" in the context of molecule X refers to an indirect physical attachment of a molecule X to a silk fibroin via a third entity, the five-amino acid peptide "tail" being that entity. In one embodiment, the tail binds to silk fibroin by hydrophobic interaction to the silk fibroin. Alternatively, the "tail" binds the silk molecules by hydrogen bonding and/or covalent bonding. It is envisioned that the "tail" can bind silk fibroins by a combination of hydrophobic interactions, hydrogen bonds, and covalent bonds. By attaching a molecule X to a "tail" described herein, it is possible to indirectly link the molecule X to silk fibroin via the tail, and thus to the silk hydrogels described herein. Accordingly, in one embodiment, the five-amino acid peptide "tail" comprises hydrophobic and/or apolar (non polar) amino acid residues such as valine, leucine, isoleucine, phenylalanine, tryptophan, methionine, cysteine, alanine, tyrosine, serine, proline, histidine, threonine and glycine. Various combinations of hydrophobic and/or apolar amino acid residues are possible, for e.g. LLLLL (SEQ ID NO: 15), LLFFL (SEQ ID NO: 16), LFLWL (SEQ ID NO: 17), FLWLL (SEQ ID NO: 18) and LALGL (SEQ ID NO: 19). In other embodiments, the tail comprises any combination of the twenty standard conventional amino acid residues. In other embodiments, the tail comprises hydrophobic and/or apolar (non polar) and amino acids residues with hydrophobic side chains, e.g. arginine and lysine. As used herein, the term "comprising" or "comprises" means that other elements can also be present in addition to the defined elements presented. The use of "comprising" indicates inclusion rather than limitation.

In one embodiment, the molecule X is attached to a tail at the carboxyl (COOH) end of the five-amino acid peptide. In another embodiment, the molecule X is attached to a tail at the amino ($NH_2$) end of the five-amino acid peptide.

In one embodiment, the five-amino acid peptide "tail" capable of linking or conjugating a molecule X to a silk molecule or fibroin when the molecule X is attached to the tail comprise more than five amino acid residues, e.g. six or seven hydrophobic and/or apolar amino acid residues, such as LLLLLL (SEQ ID NO: 20).

In one embodiment, the five-amino acid peptide "tail" comprises amino acid residues that are part hydrophobic (i.e. the part of the side-chain nearest to the protein main-chain), for e.g. arginine and lysine. In one embodiment, the part hydrophobic amino acid residues flank the five-amino acid peptide "tail" such as in RLLLLLR (SEQ ID NO: 21), KLLLLLR (SEQ ID NO: 22) and KLLLLLK (SEQ ID NO: 23).

In one embodiment, the five-amino acid peptide "tail" is separated from a molecule X by a spacer peptide. Spacer peptides should generally have non-polar amino acid residues, such as, glycine and proline. In one embodiment, the spacer comprises unnatural amino acid residues such as nor amino acids and keto-substituted amino acids. Such unnatural amino acid residues are well known to one skilled in the art.

In one embodiment, the spacer peptide is attached to a tail at the carboxyl (COOH) end of the five-amino acid peptide. In another embodiment, the spacer is attached to a tail at the amino ($NH_2$) end of the five-amino acid peptide.

The length of the space peptide is variable. The spacer serves to link the molecule X and tail together and also to provide steric freedom to the molecule X, allowing for proper orientation of a molecule X (e.g. cell binding domains such as the RGD domain) and the correct interaction of the molecule X with cells in vivo. A spacer which is too short can prevent the molecule X from being properly functional (i.e., holding it too tight to the silk molecules and away from cells), a spacer which is too long can cause undesired effects as well (i.e., non-specific association of peptides or shortened efficacy from peptide due to spacer breakage). In one embodiment, the number of amino acid residues in a spacer can range form 1 to 300. In one embodiment, the spacer comprises a single amino acid residue, such as a G or a P. Examples of spacers with more amino acid residues are GSPGISGGGGGILE (SEQ ID NO: 24) and SGGGGKSSAPI (SEQ ID NO: 25).

In one embodiment, the molecule X is any biological molecule or fragment thereof. Examples biological molecules include but are not limited to growth factors, hormones, cytokines, chemokines, extracellular matrix compounds, osteogenic protein (OP), bone morphogenetic protein (BMP), growth and differentiation factor (GDF), transforming growth factor (TGF), epidermal growth factor (EGF), vascular endothelial growth factor (VEGF), interleukin (IL), platelet derived growth factor (PDGF), fibroblast growth factor (FGF), insulin-like growth factor (IGF), basic fibroblast growth factor (BFGF), fibroblast activation protein (FAP), disintegrin, metalloproteinase (ADAM), matrix metalloproteinase (MMP), connective tissue growth factor (CTGF), stromal derived growth factor (SDGF), keratinocyte growth factor (KGF), tumor necrosis factor (TNF), interferon (IFN), erythropoietin (EPO), hepatocyte growth factor (HGF), thrombopoietin (TPO), granulocyte colony stimulating factor (GCSF), granulocyte macrophage colony stimulating factor (GMCSF), myostatin (GDF-8), collagen, elastin, laminin, hyaluronic acid, decorin, actin, and tubulin. Examples fragments of biological molecules include but are not limited to known cell integrin binding domains including but not limited to RGD, KQAGDV (SEQ ID NO: 4), PHSRN (SEQ ID NO: 5), YIGSR (SEQ ID NO: 6), CDPGYIGSR (SEQ ID NO: 7), IKVAV (SEQ ID NO: 8), RNIAEIIKDI (SEQ ID NO: 9), YFQRYLI (SEQ ID NO: 10), PDSGR (SEQ ID NO: 11), FHRRIKA (SEQ ID NO: 12), PRRARV (SEQ ID NO: 13), and WQPPRAR1 (SEQ ID NO: 14).

In other embodiments, the molecule X is any recombinant, synthetic, or non-native polymeric compounds. Examples include but are not limited to chitin, poly-lactic acid (PLA), poly-glycolic acid (PGA), as tracers (e. g. radioisotopes), contrasting agents (e. g. imaging dyes), aptamers, avimers, peptides, nuclei acids, modified polysaccharide coatings, drugs (chemotherapy drugs), and recombinant antibodies or antibody-based moieties.

In one embodiment, the present invention provides a synthetic molecule having the formula: (molecule X)$_n$-(spacer peptide)$_{0-300}$-(tail)-$NH_2$ for linking with silk molecule or fibroin, wherein "n" is a whole integer ranging from 1-30, and wherein the amino acid residues of the spacer ranges from 0-300. Examples of such synthetic molecule capable for linking to silk molecule or fibroin are GRGDIPASSKG$_4$SRL$_6$R—$NH_2$ (SEQ ID NO: 1), Ac—GdRGDIPASSKG$_4$SdRL$_6$dR-$NH_2$ (SEQ ID NO: 2), (VEGF)-(VEGF)-GSPGISGGGGGILEKLLLLLK-$NH_2$ (SEQ ID NO: 26), (HIV-C-peptide)$_3$-GSPGISGGGGGILE-KLALWLLR-$NH_2$ (SEQ ID NO: 27), (taxol)$_2$-GSPGISGGGGGILERLLLLR-$NH_2$ (SEQ ID NO: 28) and (EPO)$_2$-GSPGISGGGGGILERLLWLLR-$NH_2$ (SEQ ID NO: 29). When used in the context of the silk hydrogel described herein, the synthetic molecule of SEQ ID NO: 1 enable better tissue attachment of the hydrogel construct in vivo, the synthetic molecule of SEQ ID NO: 26 can promote blood vessel generation (neo-angiogenesis) in tissue engineered constructs, the synthetic molecule of SEQ ID NO: 28 can provide a slow release anti-HIV medication in the form of a transdermal delivery patch, the synthetic molecule of SEQ ID. NO: 28 can provide sustained dosage of anti-cancer drug in vivo, and the synthetic molecule of SEQ ID NO: 29 can provide a slow release EPO during cancer chemotherapy treatment.

Encompassed in the invention are injectable silk hydrogel formulations comprising a synthetic molecule having the formula: (molecule X)$_n$-(spacer peptide)$_{0-300}$-(tail)-$NH_2$ or a synthetic molecule having the formula: (molecule X)$_n$-(spacer peptide)$_{0-300}$-(tail)-$NH_2$ and an amphiphilic peptide. The amphiphilic peptide is 23RGD.

Basically, a molecule X is any entity, natural or synthetic, that can be useful and can be use in the context of silk hydrogels.

In one embodiment, the invention provides a method of conjugating a molecule X to a silk molecule or fibroin comprising mixing a synthetic molecule having the formula: (molecule X)$_n$-(spacer peptide)$_{0-300}$-(tail)-NH$_2$ with a silk molecule or fibroin or silk solution.

Methods of peptide synthesis are known to one skilled in the art, for example, the peptides described herein can be synthetically constructed by suitable known peptide polymerization techniques, such as exclusively solid phase techniques, partial solid-phase techniques, fragment condensation or classical solution couplings. For example, the peptides of the invention can be synthesized by the solid phase method using standard methods based on either t-butyloxycarbonyl (BOC) or 9-fluorenylmethoxy-carbonyl (FMOC) protecting groups. This methodology is described by G. B. Fields et al. in Synthetic Peptides: A User's Guide, W. M. Freeman & Company, New York, N.Y., pp. 77-183 (1992) and in the textbook "Solid-Phase Synthesis", Stewart & Young, Freemen & Company, San Francisco, 1969, and are exemplified by the disclosure of U.S. Pat. No. 4,105,603, issued Aug. 8, 1979. Classical solution synthesis is described in detail in "Methoden der Organischen Chemic (Houben-Weyl): Synthese von Peptiden", E. Wunsch (editor) (1974) Georg Thieme Verlag, Stuttgart West Germany. The fragment condensation method of synthesis is exemplified in U.S. Pat. No. 3,972,859. Other available syntheses are exemplified in U.S. Pat. No. 3,842,067, U.S. Pat. No. 3,872,925, issued Jan. 28, 1975, Merrifield B, Protein Science (1996), 5: 1947-1951; The chemical synthesis of proteins; Mutter M, Int J Pept Protein Res 1979 March; 13 (3): 274-7 Studies on the coupling rates in liquid-phase peptide synthesis using competition experiments; and Solid Phase Peptide Synthesis in the series Methods in Enzymology (Fields, G. B. (1997) Solid-Phase Peptide Synthesis. Academic Press, San Diego.#9830). The foregoing disclosures are incorporated herein by reference. Molecular DNA methods can also be used. The coding sequence of the short spacer can be constructed be annealing a complementary pair of primers. One of skill in the art can design and synthesize oligonucleotides that will code for the selected spacer.

Methods of linking peptides are also known in the art. The physical linking of the individual isolated peptides into oligomeric peptides as set forth herein, can be effected by chemical conjugation procedures well known in the art, such as by creating peptide linkages, use of condensation agents, and by employing well known bifunctional cross-linking reagents. The conjugation may be direct, which includes linkages not involving any intervening group, e.g., direct peptide linkages, or indirect, wherein the linkage contains an intervening moiety, such as a protein or peptide, e.g., plasma albumin, or other spacer molecule. For example, the linkage may be via a heterobifunctional or homobifunctional cross-linker, e.g., carbodiimide, glutaraldehyde, N-succinimidyl 3-(2-pyridydithio)propionate (SPDP) and derivatives, bis-maleimide, 4-(N-maleimidomethyl)cyclohexane-1-carboxylate, and the like.

Cross-linking can also be accomplished without exogenous cross-linkers by utilizing reactive groups on the molecules being conjugated. Methods for chemically cross-linking peptide molecules are generally known in the art, and a number of hetero- and homobifunctional agents are described in, e.g., U.S. Pat. Nos. 4,355,023, 4,657,853, 4,676,980, 4,925,921, and 4,970,156, and Immuno Technology Catalogue and Handbook, Pierce Chemical Co. (1989), each of which is incorporated herein by reference. Such conjugation, including cross-linking, should be performed so as not to substantially affect the desired function of the peptide oligomer or entity conjugated thereto, including therapeutic agents, and moieties capable of binding substances of interest.

Conjugation of individual peptide can be effected by a linkage via the N-terminal or the C-terminal of the peptide, resulting in an N-linked peptide oligomer or a C-linked peptide oligomer, respectively.

It will be apparent to one skilled in the art that alternative linkers can be used to link peptides, for example the use of chemical protein crosslinkers. For example homobifunctional crosslinker such as disuccinimidyl-suberimidate-dihydrochloride; dimethyl-adipimidate-dihydrochloride; 1,5,-2,4-dinitrobenzene or heterobifunctional crosslinkers such as N-hydroxysuccinimidyl 2,3-dibromopropionate; 1ethyl-3-[3-dimethylaminopropyl]carbodiimide hydrochloride; and succinimidyl4-[n-maleimidomethyl]-cyclohexane-1-carboxylate.

Several embodiments will now be described further by non-limiting examples.

EXAMPLES

The following examples illustrate representative embodiments now contemplated, but should not be construed to limit the disclosed purified silk fibroin and method for purifying such silk fibroins, hydrogels comprising such silk fibroin with or without an amphiphilic peptide and methods for making hydrogels comprising such silk fibroin and the use of silk fibroin hydrogels in a variety of medical uses, including, without limitation fillers for tissue space, templates for tissue reconstruction or regeneration, scaffolds for cells in tissue engineering applications and for disease models, a surface coating to improve medical device function, or as a platform for drug delivery.

Example 1

Silk Sericin Extraction

Silk fibroin for generation of the hydrogel was obtained in the form of degummed *B. mori* silk at a size of 20 denier-22 denier (38 μm±5.6 μm diameter). This degummed silk was further processed in order to remove the inherently present and potentially antigenic protein glue, sericin that conjoins independent fibroin filaments. This was done as described previously herein. Following removal of sericin, the pure fibroin was dried carefully to ambient humidity levels using a laminar flow hood.

Example 2

Generation of Silk Fibroin Solution

Silk fibroin filaments, cleaned of their sericin and rinsed free of insoluble debris and ionic contaminants were used for the generation of an aqueous silk solution. These silk fibers were added to a solution of 9.3M LiBr and purified water (e.g., MILLI-Q® Ultrapure Water Purification Systems) (Millipore, Billerica, Mass.) to make a solution consisting of 20% pure silk (% w/v). This mixture was then heated to a temperature of 60° C. and digested for a period of four hours. A total of 12 mL of the resultant solution was then loaded into a 3 mL-12 mL Slide-A-Lyzer dialysis cassette (Pierce Biotechnology, Inc., Rockford, Ill.) (molecular weight cutoff of 3.5 kD) and placed into a beaker containing purified water as a dialysis buffer at a volume of 1 L water per 12 mL cassette of silk solution. The beakers were placed on stir plates and stirred continuously for the duration of the dialysis. Changes of dialysis buffer occurred at 1, 4, 12, 24, and 36 hours of processing time.

Following dialysis, the solution was removed from the cassettes by means of a syringe and needle and centrifuged at 30,000 g relative centrifugal force (RCF) at 4° C. for 30 minutes, decanting the supernatant (silk solution) into a clean centrifuge tube, then repeating the centrifugation for a further 30 minutes. This process of centrifugation is beneficial for removal of insoluble particulate debris associated with the silk solution both prior to and following after dialysis. It is believed that such insoluble debris could serve as antigens in vivo or perhaps nucleation points about which gelation of the silk could occur, shortening storage life of the solution and compromising the uniformity of the gelation system. After completion of the second centrifugation, the supernatant was again collected and stored at 4° C. until needed. To confirm uniformity of the dialysis product, known volumes of the solution were collected, massed, and then dried completely through lyophilization. These lyophilized samples were then massed and the dry mass of solution compared to initial solution volume to determine percent silk present per unit volume of solution. Additionally, the solution was assessed via X-ray Photoelectron Spectroscopy (XPS) analysis to ensure that no detectable quantities of $Li^+$ or $Br^-$ ions were present in the solution.

Example 3

Induction of Gelation

A variety of different methods were employed in the course of hydrogel development for the purposes of contrasting and comparing certain relevant properties of various formulae. Regardless of the nature in which the gelation process was carried out, the final determination that a "gel" state had been reached was applied uniformly to all groups. A solution or composite of solutions (i.e., silk solution blended with an enhancer or enhancer solution) was considered a gel after observing formation of a uniform solid phase throughout the entire volume, generally opaque and white in appearance.

Samples to be produced by passive gelation were not exposed to any enhancer additives. These gels were produced by measuring a volume of silk solution into a casting vessel, for the purposes of these experiments, polypropylene tubes sealed against air penetration and water loss, and the sample allowed to stand under ambient room conditions (nominally 20-24° C., 1 atm, 40% relative humidity) until fully gelled. Care was taken to ensure uniformity of casting vessels material of construction across groups so as to avoid potential influence from surface effects. These effects may serve to enhance or inhibit gelation and may be caused by factors including but not limited to siliconization, surface roughness, surface charge, debris contamination, surface hydrophobicity/hydrophilicity, and altered mass transfer dynamics.

Samples produced by means of a 23RGD-induced process were made in one of two ways, the first being direct addition of 23RGD in a pre-determined ratio to the silk solution without any sort of reconstitution. The 23RGD (obtained as a desiccated fine powder form) was blended into a measured volume of 8% silk solution within the casting vessel by pipetting using a 1000 μL pipette. These gels were then cast in polypropylene tubes, sealed against air penetration and water loss, and the sample was allowed to stand under ambient room conditions (nominally 20-24° C., 1 atm, 40% relative humidity) until fully gelled.

The 23RGD-induced gels were also produced by first dissolving the 23RGD powder in purified water. The concentration of this solution was determined based upon the amount of 23RGD to be introduced into a gel and the final concentration of silk desired in the gel. In the case of 4% silk gels enhanced with 23RGD, quantities of water equal to the amount of 8% silk solution to be used in the gel were used for the dissolution of appropriate quantities of 23RGD. In the case of gels induced by addition of 23RGD to be generated at a molar ratio of 3:1 23RGD:silk, a quantity of 23RGD was dissolved in 1 mL of water per 1 mL of 8% silk solution to be gelled. This mixing was performed in the casting vessel as well, being accomplished by means of rapid pipetting with a 1000 μL pipette when appropriate. These gels were then cast in polypropylene tubes, sealed against air penetration and water loss, and the sample was allowed to stand under ambient room conditions (nominally 20-24° C., 1 atm, 40% relative humidity) until fully gelled.

Samples produced by means of ethanol-enhanced gelation (EEG) were generated by means of directly adding ethanol to a measured volume of 8% silk solution in the casting vessel. The ethanol is added in a quantity such that the volume added should yield a volumetric dilution of the 8% silk solution resulting in the final required concentration of silk within the gel, assuming minimal volume loss due to miscibility of the organic added. The mixture of ethanol and silk solution is then mixed by means of pipetting with a 1000 μL pipette when appropriate. These gels were then cast in polypropylene tubes, sealed against air penetration and water loss, and the sample was allowed to stand under ambient room conditions (nominally 20-24° C., 1 atm, 40% relative humidity) until fully gelled.

Samples produced by a combined 23RGD-ethanol effect (RGDEEG) were generated using a solution of 90% ethanol, 10% purified water and appropriate quantities of 23RGD dissolved in this solvent. It was not possible to readily dissolve 23RGD in pure ethanol and it was believed that undissolved 23RGD might cause poor distribution of the peptide throughout the gel phase. As a result, it was determined that since a solution of ethanol and water offering similar gelation acceleration characteristics to a pure ethanol solution and reasonable 23RGD solubility would be an acceptable alternative. A solution of 90% ethanol and 10% water met both of these criteria and as a result was used for generation of these gels. The 23RGD concentration of this ethanol solution was determined based upon the amount of 23RGD to be introduced into a gel and the final concentration of silk desired in the gel. In the case of 4% silk gels enhanced with 23RGD, quantities of 90% ethanol equal to the amount of 8% silk solution to be used in the gel were used for the dissolution of appropriate quantities of 23RGD. In the case of gels induced by addition of 23RGD to be generated at a molar ratio of 3:1 23RGD:silk, a quantity of 23RGD was dissolved in 1 mL of 90& ethanol per 1 mL of 8% silk solution to be gelled. This mixing was performed in the casting vessel as well, being accomplished by means of rapid pipetting with a 1000 μL pipette when appropriate. These gels were then cast in polypropylene tubes, sealed against air penetration and water loss, and the sample was allowed to stand under ambient room conditions (nominally 20-24° C., 1 atm, 40% relative humidity) until fully gelled.

Silk gelation times were determined by casting gels according to the methods above, the exception being that gels were mixed not through pipetting, but through vigorous mechanical shaking. These studies were conducted using 1.5 mL microcentrifuge tubes as casting vessels with sample groups of N=6 used for each gel formulation (FIG. 1). The determination that a "gel" state had been reached was made in the method as described above, based upon observation of a uniform solid phase throughout the entire volume, generally opaque and white in appearance.

Gelation time varied widely depending on specific formulation. The 8P silk samples took 21 days until gelation while the 4P samples required 31±1 day (data not shown). EEG samples gelled significantly faster than PG samples with a 4E sample requiring 27±5.4 seconds for gelation ($p \leq 0.05$). EEG samples gelled more rapidly as the concentration of ethanol added increased with time required gelation times of 1770±600 s, 670.3±101.0 s, 29.8±5.2 s, 9.7±2.0 s, and 4.2±0.8 s for 6.4E, 6E, 4.8E, 4E, and 3.2E respectively. There were significant differences between all times except 4.8E and 4E, 4E and 3.2E, and 4.8E and 3.2E. RGDEEG gels generated a tightly localized white fibrous precipitate instantaneously upon addition of the ethanol solution to the silk and gelled more quickly than PG samples, though they were slower than EEG gels. 4RL, 4RM and 4RH samples took 22.7±2.5 seconds, 38.8±4.5 seconds, and 154.5±5 seconds to gel with 4RH differing significantly from the other RGDEEG formulations.

Gelation timing experiments revealed the time constraints posed by the PG method. Results indicated that, while increased silk concentration decreased gelation time, the total time to gel was decreased only from 31 days for 4P to 21 days for 8P. This may result from the increased frequency of collisions between silk molecules in solution and resultant gel network assembly. Using ethanol directly added to silk solution as an accelerant proved to dramatically decrease the gelation time of the silk by increasing the volume of ethanol added in a fashion well-modeled by a power function. This increasingly rapid gelation is likely caused by greater competition for hydrating water molecules between silk and ethanol coupled with altered electronegativity of the solution, both favoring forced aggregation of the silk molecules. Studies conducted on RGDEEG samples revealed that addition of greater concentrations of RGD led to increasing gelation times modeled by an exponential function. This appears counter-intuitive as it was expected that RGD should function in some capacity to accelerate gelation.

The slowing of gelation in RGDEEG samples may result from difficulties in silk molecular binding to the RGD-coated silk precipitates, perhaps due to stearic interference with hydrophobic regions of silk chains. Upon RGD-ethanol accelerant addition to the silk solution, a large quantity of silk-RGD complexes was precipitated from the solution. It was noted during the gelation of RGDEEG samples that a fibrillar, white, opaque precipitate was consistently formed within the solution mixture immediately upon mixing. This precipitation from solution may be evidence of this rapid assembly of high concentration silk-RGD precipitates. This formation may be caused by association between silk micelles and peptide molecules in solution, disruption of the silk micelles, and rapid assembly of them into a tightly-localized fibrillar structure. This rapid assembly may progress until driving gradients generated by the differing solvent chemistries provided by the ethanol and water reach an equilibrium state. At this point, silk molecules are able to remain stably in solution with further silk network assembly occurring only by slow lengthening of the initially formed precipitates. While this precipitation provided a high number of nucleation points to initiate completion of a gel network, these nucleation points may be of limited utility based upon availability of binding sites. The remaining silk molecules were much slower to assemble as a result. These precipitates also tended to initiate assembly of a peripheral network comprised largely of loose α-helix and random coil motifs, possibly due to interference in silk packing due to the interference of these particles.

The hydrogels produced by the methods described above derive substantial benefit from the ability to more precisely control the time course for its gelation in comparison to that of a conventionally designed and cast gel. It is evident from monitoring the time between casting and gelation of the device and similarly cast, non-enhanced or exclusively ethanol modified gels that 23RGD under certain circumstances may be manipulated to have an additional accelerant effect upon the process of gelation. This observed enhancer effect both mitigates the time constraints and controllability associated with non-modified gels and additionally alters the manner in which the protein aggregate network is formed relative to solely ethanol enhanced gels Example 4

Determination of Residual Ethanol by Colorimetric Analysis

Following gelation of a sample produced with either an ethanol or 23RGD component, the gel was removed from the casting vessel and immersed in a bulk of purified water as a rinse buffer. This bulk comprised a volume such that the volumetric ratio of water to gel was $\geq 100:1$. The gel was permitted to lay static in the rinse buffer for a period of 72 hours, changing the water every 12 hours.

Figure 2:
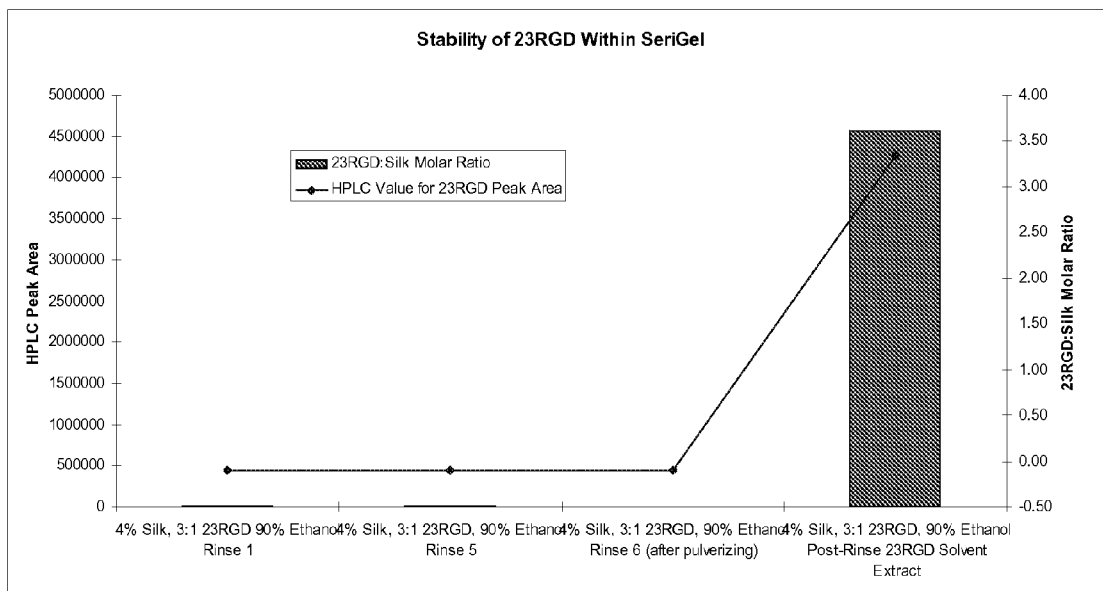
FIG. 2 is a graph of HPLC data illustrating the integration of 23RGD and stability of its binding to 4% silk gel material made with an enhancer solution consisting of a 3:1 molar ratio of 23RGD:silk dissolved in 90% ethanol, 10% water when rinsed multiple times in ultra-purified water over several days. Data are shown for both total peak area and calculated 23RGD:silk molar ratio based on a 23RGD standard curve.

Samples of silk gel were evaluated to determine the total residual content of ethanol in a series of 23RGD-ethanol- and ethanol-enhanced gels. Briefly, samples of gel (N=4 of each type) generated as described above were processed and analyzed using an Ethanol Assay Kit (kit # K620-100 from BioVision Research Prods, Mountain View, Calif.). Samples of gel were cut to a size of approximately 0.3 cm in height by 0.5 cm in diameter (approximately 250 mg). These samples were massed to the nearest 0.1 mg using an APX-60 (Denver Instrument, Denver Colo.) balance as per the manufacturer's instructions. These gel samples were individually ground using a metal spatula and placed into 250 μL of Milli-Q water in microcentrifuge tubes. These gels were incubated at 37° C. for a period of 24 hours. After incubation, the gels were centrifuged on an Eppendorf 5415 microcentrifuge with an HA 45-18-11 rotor (Hamburg, Germany) at 18,000 rpm for 30 minutes. At the conclusion of this centrifugation step, the supernatant was used as the sample of interest according to the instructions provided by the kit manufacturer. Colorimetric analyses of the sample was performed at an absorbance of 570 nm using a spectrophotometer, and in conjunction with a standard curve, residual percentages of ethanol in the gel were calculated (Table 1, FIG. 2). It was shown in this process that the leeching step is capable of substantially removing residual ethanol from the silk gels, as none of these materials exhibited a residual ethanol component of greater than 5% ethanol by mass.

TABLE 1

Determination of Residual Ethanol by Colorimetric Analysis

| Silk Concentration | Enhancer Solvent | Enhancer Solute | Initial Ethanol Concentration | Final Ethanol Concentration Mean | Stdev |
|---|---|---|---|---|---|
| 2% | 90% | None | 68% | 2.49% | 0.06% |
| | | 3:1 23RDG:Silk | | 4.44% | 0.13% |
| | | 10:1 23RDG:Silk | | 4.77% | 0.29% |

TABLE 1-continued

Determination of Residual Ethanol by Colorimetric Analysis

| Silk Concentration | Enhancer Solvent | Enhancer Solute | Initial Ethanol Concentration | Final Ethanol Concentration Mean | Stdev |
|---|---|---|---|---|---|
| 4% | | None | 45% | 2.55% | 0.07% |
| | | 3:1 23RDG:Silk | | 2.86% | 0.08% |
| | | 10:1 23RDG:Silk | | 2.97% | 0.07% |
| 6% | | None | 22.5% | 3.12% | 0.05% |
| | | 3:1 23RDG:Silk | | 3.16% | 0.04% |
| | | 10:1 23RDG:Silk | | 2.99% | 0.10% |

Example 5

23RGD Quantification by HPLC

23RGD-infused gels were studied to quantify the amount of 23RGD bound to the silk-hydrogel device as well as the quantity of free 23RGD which might be rinsed free of the device under relevant conditions. Briefly, samples of 23RGD-infused gel were cast and rinsed according to the methods above, with samples of rinse buffer being collected from each rinse for subsequent analysis by HPLC. Additionally, subsequent to the last rinse, the gel samples were mechanically pulverized by means of a stainless steel stirring rod and the adsorbed 23RGD removed by incubation for 4 hours in a dissolving buffer. This mixture of gel and solvent was then centrifuged on an Eppendorf 5415C at 16,000 g RCF for 30 minutes. The supernatant was collected and centrifuged another 30 minutes at 16,000 g RCF after which time the supernatant was collected in a sample vial for HPLC analysis. Samples of rinse buffer from the first and last rinse were centrifuged in the same fashion after being diluted with the same solvent the gel was extracted with in a volumetric ratio of 1 part rinse buffer to 4 parts solvent. To ensure 23RGD-hydrogel device rinse-exposed surface area was not a limiting factor, the same rinse and extraction process was performed upon devices pulverized after gelation and before rinsing. The peak area consistent with 23RGD for each HPLC sample was taken and these data compared against a standard curve generated for 23RGD on the same HPLC unit under identical handling and run conditions.

The resultant data indicated levels of signal from 23RGD in samples collected from rinse buffer were just slightly higher than values for 23RGD solvent alone and were immeasurable by the standard curve, expected to resolve a relative 23RGD:silk ratio of 0.05:1. By comparison, the assay was able to detect a ratio of 3.35:1 in the final rinsed and extracted 23RGD-enhanced gel.

HPLC data confirmed complete retention of RGD on the silk hydrogel material after the rinse process. This provides not only a functional RGD component to this specific series of hydrogel formulations, but indication for use of amphiphilic peptides as candidates for introduction of other components into silk gels. This knowledge might be applied to a number of other biologically active peptide sequences, though additional work must be done to understand how these specific peptides might influence gelation and how gelation in turn impacts the functionality of these peptides.

Example 6

Silk Gel Dry Massing

Silk gel samples of various 23RGD-ethanol- and ethanol-enhanced formulations were cut into sample cylinders (N=4 of each type) of approximately 0.7 cm in height by 0.5 cm in diameter (approximately 500 mg). These samples were massed to the nearest 0.1 mg using an APX-60 (Denver Instrument, Denver Colo.) balance as per the manufacturer's instructions and placed into massed microcentrifuge tubes. After this, the samples were frozen to −80° C. for 24 hours. At the conclusion of this time, the samples were placed into a lyophilizer unit for a period of 96 hours to remove all water content. Following the completion of this 96 hour drying, the remaining protein components of the silk gel samples were massed again and the mass fraction of water in the samples determined.

Figure 3:
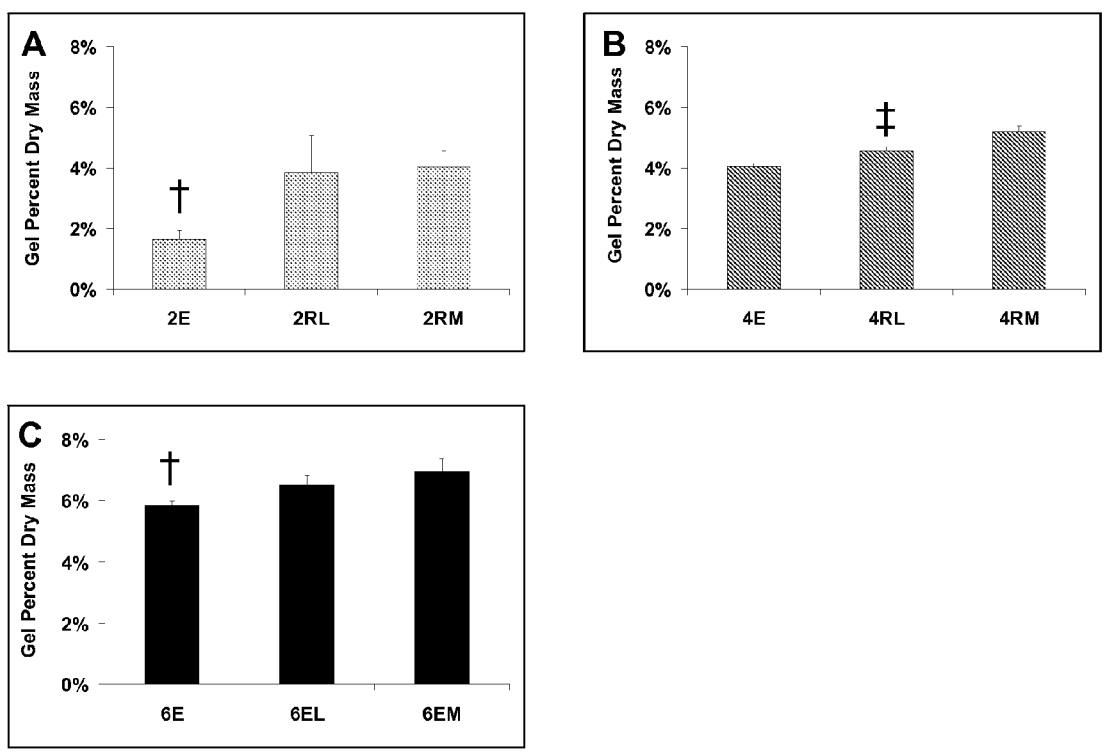
FIG. 3 is a graph comparing gel dry mass component at different RGD concentrations for 2% silk gels (A), 4% silk gels (B), and 6% gels (C). * Samples differ significantly, p<0.05; † sample differs significantly from all others; ‡ all samples differ significantly.

Gel dry massing showed an increasing percentage of dry mass as RGD component increased in each silk concentration group (FIG. 3). The dry mass of 2E was significantly less than 2RL and 2RM ($p \leq 0.05$) at 1.63±0.30%, 3.85±1.23% and 4.03±0.53% respectively (FIG. 3A). The dry masses of 4E, 4RL and 4RM all differed significantly from each other at 4.05±0.10%, 4.56±0.12%, and 5.19±0.18% respectively (FIG. 3B). The dry mass of 6E was significantly less than both 6RL and 6RM at 5.84±0.15%, 6.53±0.28%, and 6.95±0.40% respectively (FIG. 3C).

Figure 4:
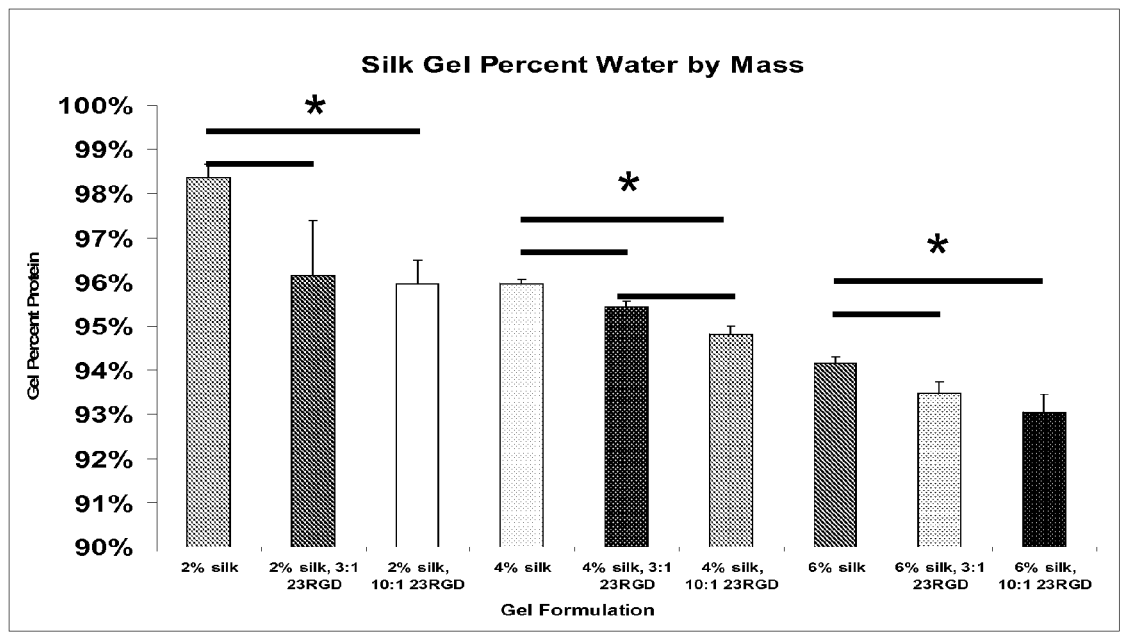
FIG. 4 illustrates the impact upon silk hydrogel water absorption and retention as identified in a gel drying assay. Data are shown as the percentage of mass retained by a silk gel sample (n=4 for each type) after being subjected to a 96-hour lyophilization process. Increasing concentrations of 23RGD enhancer caused increasing dry mass in the gel materials more substantial than the mass of the peptide itself. This phenomenon is likely due to structural differences in 23RGD-enhanced gels which do not permit a level of water entrainment equal to those of gels enhanced only with ethanol.

The gels, regardless of the silk concentration, showed a statistically significant trend toward decreasing percentage of water mass in each gel material as 23RGD component increased as determined by analysis of each silk concentration group with ANOVA (FIG. 4, Tukey post hoc, $p<0.05$). This phenomenon might be explained by the possibility that the 23RGD causes formation of a different secondary structure within the silk hydrogels and that this structure might be less hydrophilic than non-23RGD-enhanced material. It is possible that this may be manifested in a different ratio of β-sheet structure, α-helix structure, and unordered random coil for 23RGD-treated materials than their counterparts, tending to favor the more hydrophobic β-sheet conformation.

Silk gel dry mass data revealed that increasing concentrations of both silk and RGD in the silk gels increased the percentage of dry mass in these materials, though the increase from RGD was too large to attribute solely to additional peptide mass. This phenomenon might be explained by the hypothesized structure of the RGDEEG gels mentioned previously relative to PG and EEG gels. It is likely that the large regions of poorly-associated β-sheet structure in the RGDEEG gels do a poor job at integrating water into the structure. The inter-connecting regions of α-helix structures and unordered random coil are able to entrain water, but do so with less success than in the case of the more homogenous EEG gels. It may also be possible that the hydrophilic RGD sequence interfered with the dry massing procedure, causing rapid gain of water mass upon exposure of the samples to atmospheric conditions.

Example 7

Enzymatic Bioresorption

Gels specified were subjected to in vitro digestion by a solution consisting of non-specific protease mixture. Briefly, gel samples were cast to generate uniform, cylindrical samples of approximately 1 gram total weight (about 1 mL of gel). These samples were digested with a protease obtained from the bacteria *Streptomyces griseus* (Sigma catalog No. P-5147) suspended in phosphate buffered saline at a concentration of 1 mg/ml. A ratio of 3 mL of protease solution per 1 ml of initial gel was used for the purposes of this study. The protease solution was added to a sealed tube containing the gel and incubated for 24 hours at 37° C. with no mechanical mixing. After 24 hours, the solution was drained through a piece of 316 stainless steel woven wire cloth. This permitted retention of all gel particles greater than 50 µm in diameter (gap size was 43 µm by 43 µm), those smaller than that were considered to be "bioresorbed" for the purposes of this assay. After thorough draining of the solution, the mass of the gel was measured wet, but devoid of excess entrained moisture. The protease solution was then replaced and the sample incubated a further 24 hours at 37° C. This process was repeated until the samples were bioresorbed for a total of four days, changing solutions and massing each day.

Figure 5:
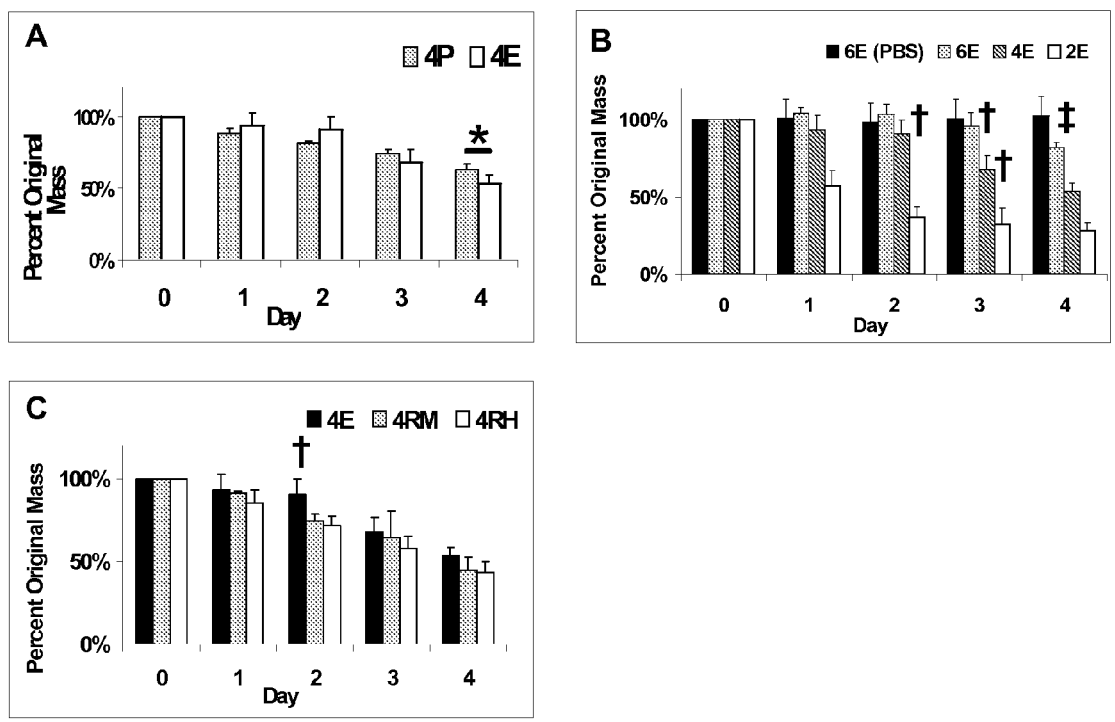
FIG. 5 shows a comparison of the percent mass loss over time due to bioresorption of samples cast by PG and EEG methods (A), cast from increasing silk concentrations (B), and cast using increasing RGD concentrations (C). * Samples differ significantly, p<0.05; † sample differs significantly from all others; ‡ all samples differ significantly.

PG samples and EEG samples bioresorbed similarly, differing significantly only at D4 where 4P samples retained 62.89±4.26% of the original mass and 4E samples retained 53.27±5.45% ($p \leq 0.05$) (FIG. 5A). 6E gels incubated in PBS showed no significant mass loss over the course of the 4 day incubation (FIG. 5B). EEG silk gels with high concentrations of fibroin exhibited higher mass retention than lower concentrations at all days. At Day 1 there were significant differences between 2E and all other gel types with 2E, 4E and 6E gels retaining 57.04±10.03%, 93.21±9.47%, and 103.98±3.65%, respectively while 6E in PBS retained 101.18%±12.01%. At Day 2, there were significant differences again between 2E and all other gel types with 2E, 4E and 6E gels retaining 36.59±7.07%, 90.60±9.24%, and 103.24±6.38% of the original mass while 6E in PBS retained 98.28%±12.38%. At Day 3 there were significant differences between all gel types in protease, with 2E, 4E and 6E gels retaining 32.36±10.48%, 67.85±8.82%, and 95.51±8.97% of the original mass. 6E samples incubated in PBS did not differ from those incubated in protease, retaining 100.39%±12.73% of the original mass. At Day 4 there were significant differences between all gel types with 2E, 4E, and 6E gels retaining 28.14±4.75%, 53.27±5.45%, and 81.76%±3.35% of the original mass while 6E in PBS retained 102.45%±12.50%. Addition of RGD to silk gels appeared to slightly decrease the mass retention of these materials when subjected to proteolytic bioresorption (FIG. 5C). 4E samples retained significantly more mass than 4RM and 4RH at Day 2 as they retained 90.6±9.24%, 74.47±4.55%, and 71.23±6.06% of the initial masses respectively. There were no further significant differences in 4E samples relative to 4RM and 4RH samples over the course of the bioresorption assay.

Figure 6:
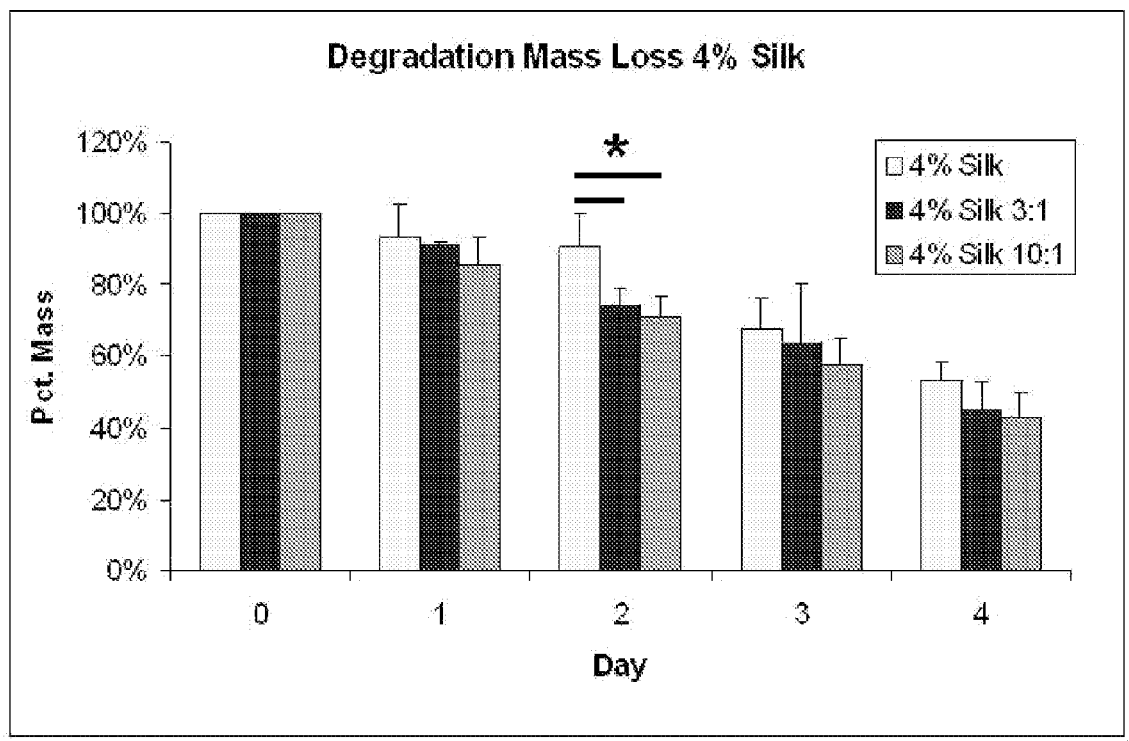
FIG. 6 illustrates wet mass loss due to proteolytic bioresorption of silk hydrogels enhanced by a combination of 23RGD and ethanol at increasing concentrations of 23RGD. As a general trend, gels enhanced with 23RGD tend to be bioresorbed more quickly based upon this assay.
Figure 7:
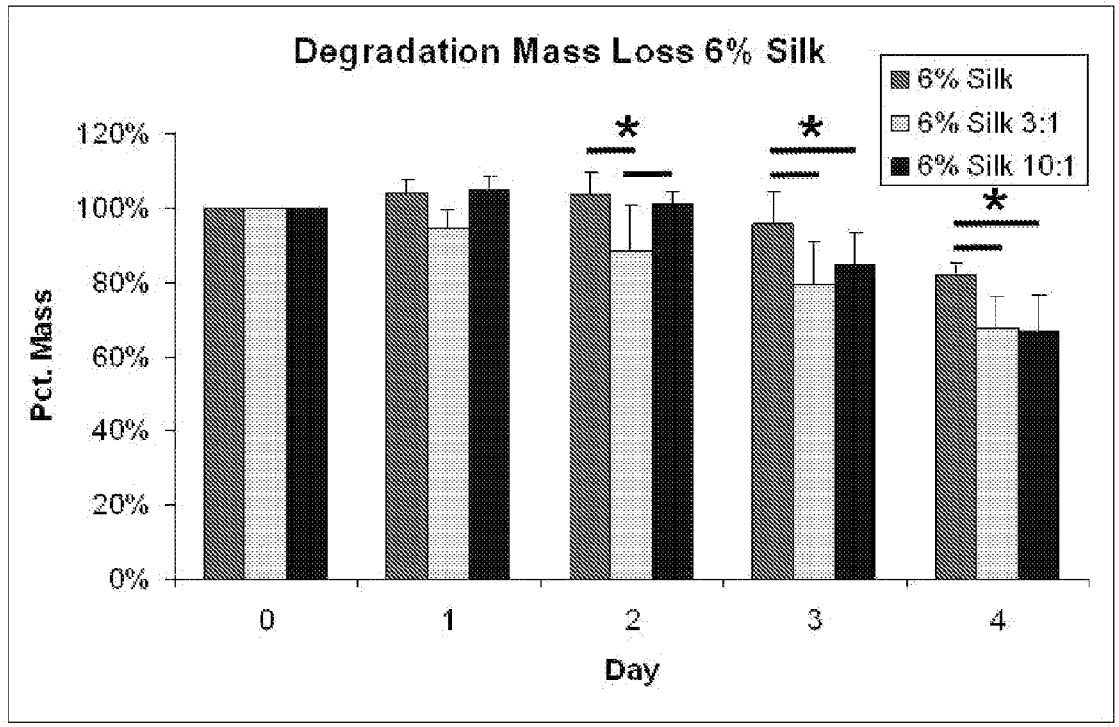
FIG. 7 is a second illustration of the bioresorption behavior of 23RGD-enhanced and non-23RGD-enhanced silk hydrogels when incubated in a protease solution. This bioresorption data serves to reinforce the trend, illustrated in FIG. 5, of a slightly more rapid rate of bioresorption of 23RGD-enhanced hydrogels in comparison to non-23RGD-enhanced gels. The figure also supports the more thorough removal of α-helix and random coil conformations from 23RGD-enhanced gels in FIG. 6 over four days of incubation in protease.
Figure 8A:
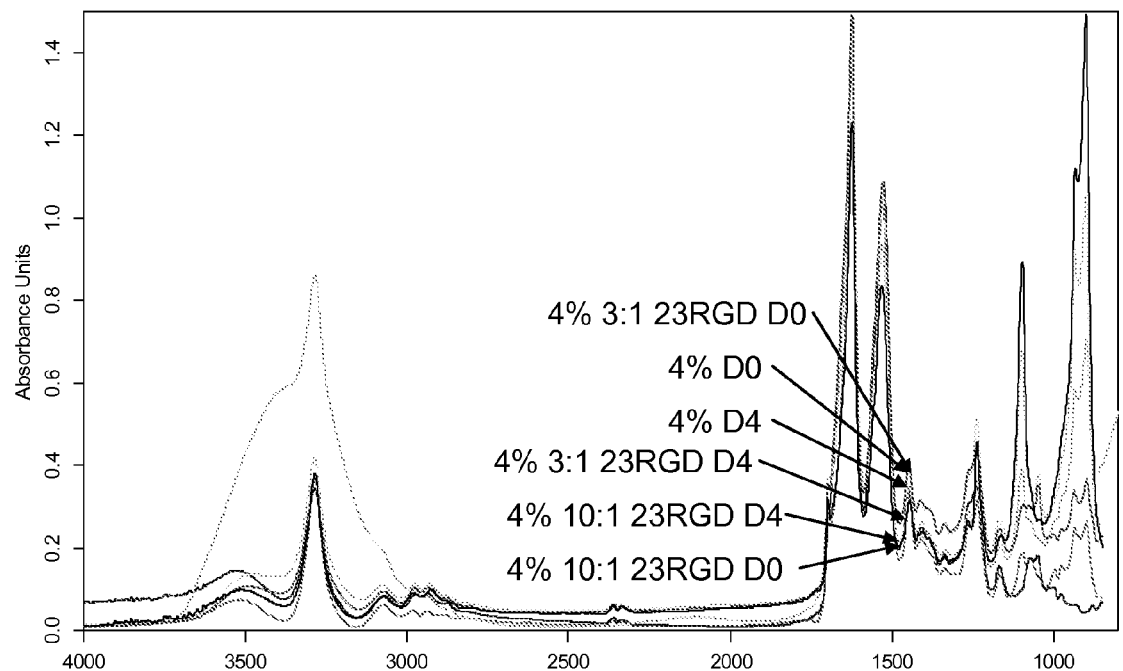
FIGS. 8A-8E show structural features observed by Fourier-Transform Infrared (FTIR) spectroscopy of 4% silk fibroin hydrogel devices which are enhanced by ethanol alone, and two 23RGD-ethanol enhancers. The full spectra (FIG. 8A) of the materials are compared and the Amide I Band (1700-1600 cm$^{-1}$) highlighted for particular attention (FIG. 8B) because of its relevance to secondary protein structure. Of specific interest is the commonality between all gels in their rich β-sheet structure (1700 cm$^{-1}$ and 1622 cm$^{-1}$ respectively, highlighted in FIGS. 8C and 8E) at all time points. These peaks become more pronounced after bioresorption, and begin to differentiate 23RGD-enhanced materials from materials enhanced with ethanol alone. This is evidenced in 23RGD-enhanced gels by a peak shift to lower wave numbers by the 1622 cm$^{-1}$ peak and dramatically increased prominence of the 1700 cm$^{-1}$ peak. Additional differences between bioresorbed and non-bioresorbed gels may be seen in regions of the spectrum known to correlate to α-helix and random coil conformations (1654 cm$^{-1}$ and 1645 cm$^{-1}$ respectively highlighted in FIG. 8D). These conformations are extensively digested in all gel types, but most completely in gels enhanced by 23RGD. This suggests that 23RGD-enhanced gels tend to bioresorb to a very β-sheet rich secondary structure in a more rapid fashion than non-23RGD-enhanced gels. Spectra shown were collected on a Bruker Equinox 55 FTIR unit using a compilation of 128 scans with a resolution of 4 cm$^{-1}$.
Figure 8B:
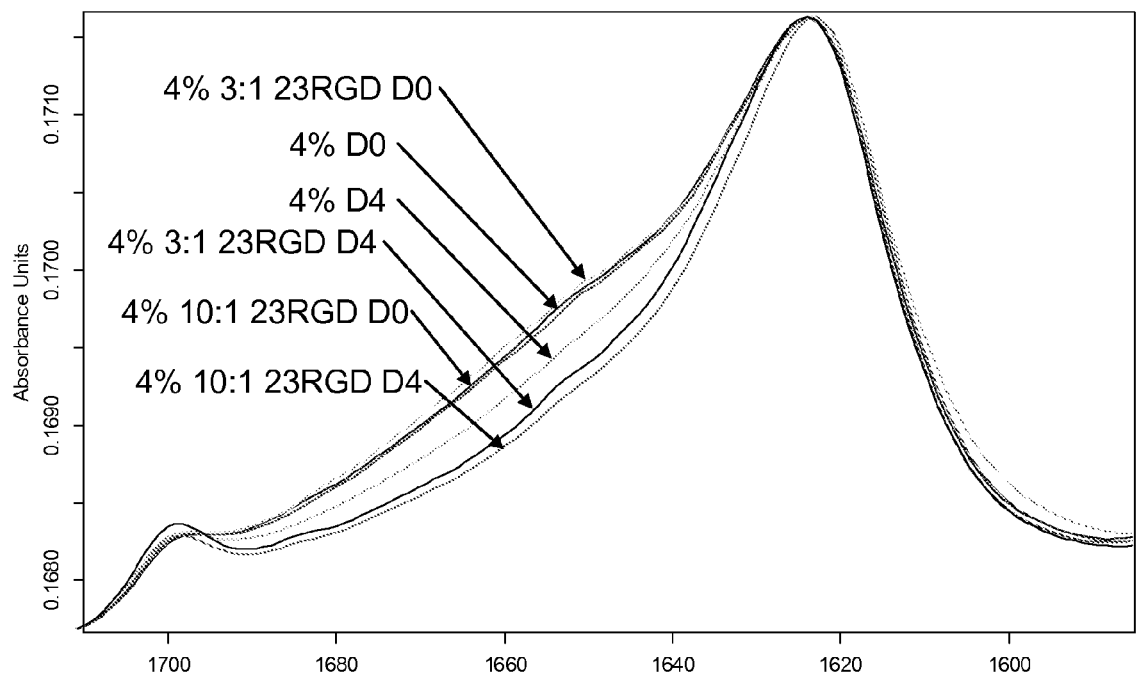
Figure 8C:
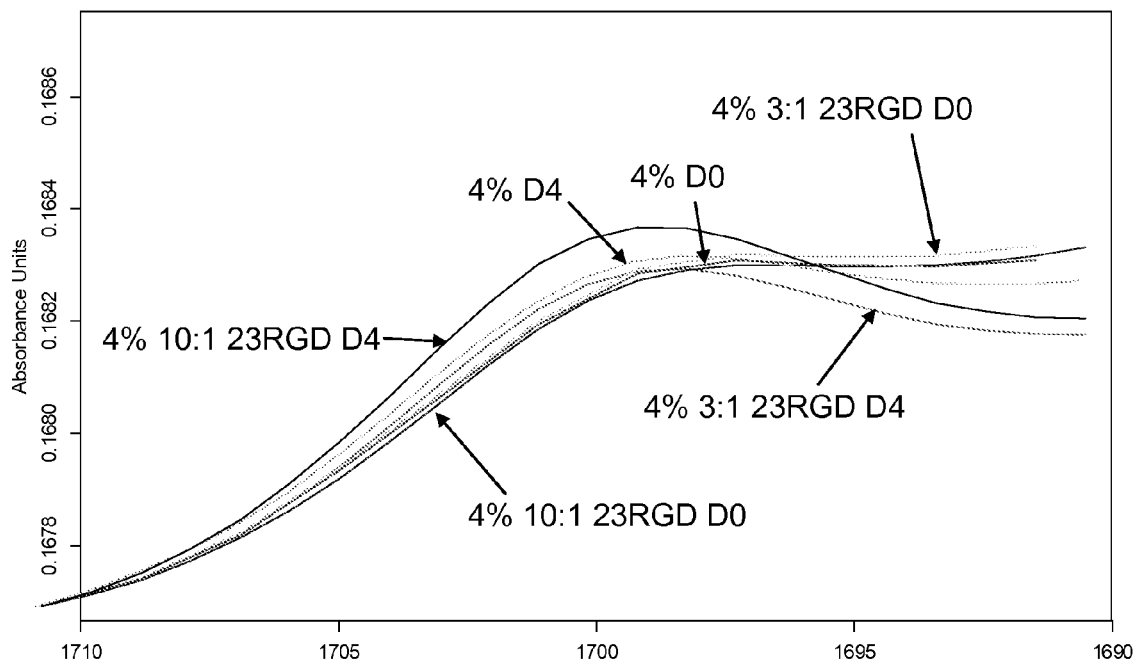
Figure 8D:
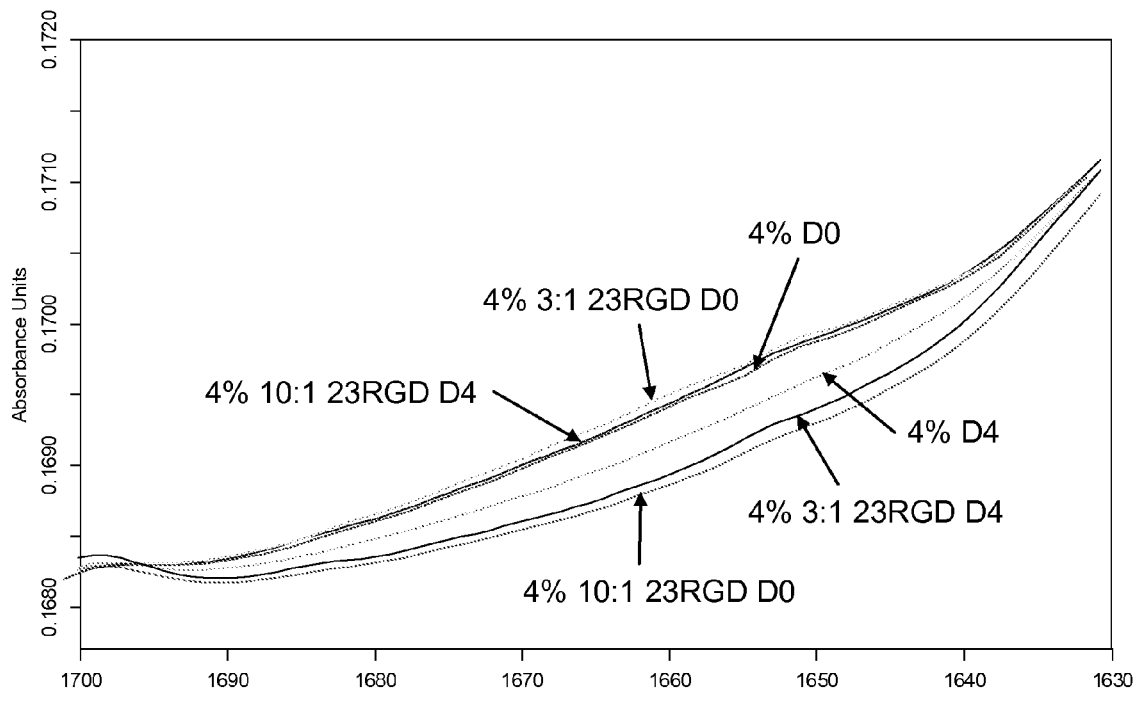
Figure 8E:
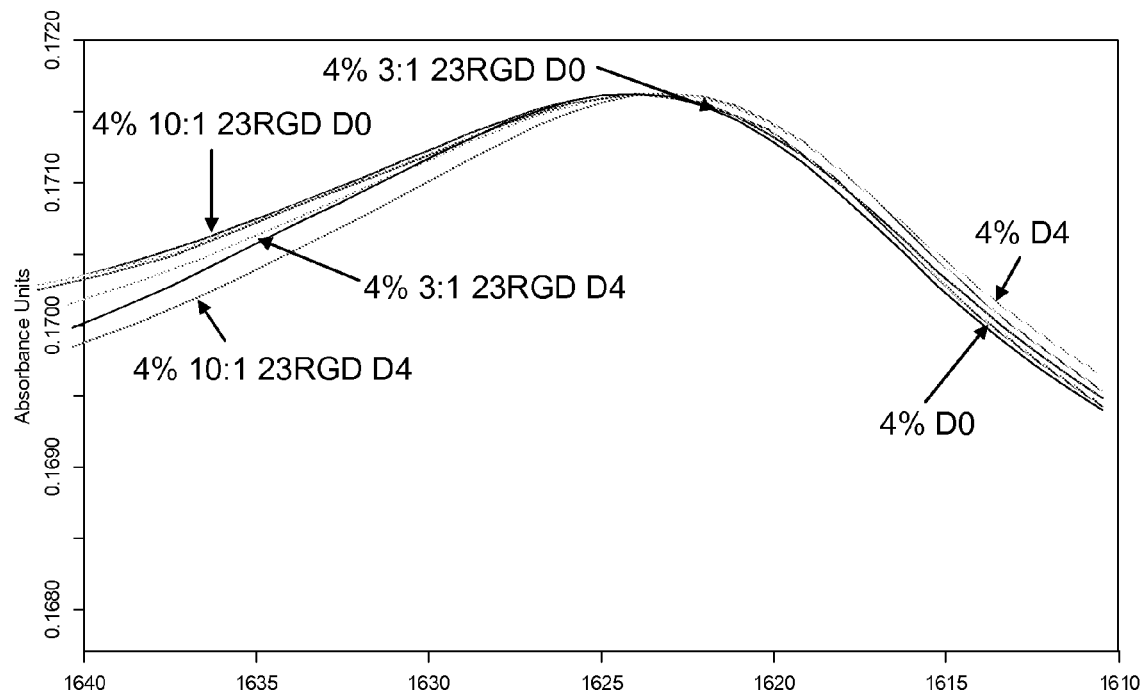

Gel samples treated with 23RGD exhibit a trend toward more rapid bioresorption within the constraints of this particular assay. This was illustrated at the 4% silk concentration (FIG. 6) and then confirmed at a concentration of 6% silk fibroin in the gel materials (FIG. 7). Significant differences in the bioresorption rates of 23RGD enhanced samples recorded by two-way ANOVA using a Bonferroni post test ($p<0.05$), particularly with 6% silk, reinforced the trend. The unique behavior attributed to 23RGD-enhanced materials may be due in part to its unique protein structure, as the bioresorption method considers particles below a size of 50 µm to be bioresorbed, regardless of their stability. It may be possible for a rich beta sheet structure to exist within 23RGD gels which is broken up into small, discrete regions by interfering regions of α-helix structure and random coil which bioresorb more quickly, creating a plethora of tiny, non-resorbed fragments in solution.

In vitro bioresorption of 4P and 4E samples showed both materials had a similar resistance to proteolysis (FIG. 5A). This is indicative that the basic process of ethanol-enhanced gelation is capable of generating a gel structure rapidly without sacrificing important material properties. It was also shown that increasing the concentration of silk in EEG gels from 2% to 4% to 6% in 2E, 4E, and 6E respectively, substantially decreased sample bioresorption mass loss (FIG. 5B). This may correlate to a more homogeneous, stable and resilient gel structure, or simply to a greater quantity of silk molecules to be cleaved by the proteases in order to bioresorb the samples. In either case, these data clearly indicate a potential for tailoring of bioresorption time scale of a silk gel material through alteration of the silk protein content of gels. It was also illustrated that a 4 day exposure to PBS did not appreciably alter the mass of 6E samples, providing a preliminary indication that EEG samples are not substantially degraded by hydrolysis. This is a further reinforcement of the stability and bulk integrity of these silk gels as many gel materials suffer from limited resilience in vivo due to high susceptibility to hydrolysis. Addition of increasing quantities of RGD to silk gels was shown to slightly increase the rates of bioresorption mass loss in comparing 4E, 4RM and 4RH (FIG. 5C). This behavior indicates that there may be some structural differences between RGDEEG and EEG gels which cause less mass loss in EEG gels as compared to RGDEEG in this bioresorption assay. This may relate directly to the previously proposed idea that RGDEEG materials consist of many small regions of robust β-sheet structure loosely bound together by a weak inter-connecting matrix of α-helix and unordered random coil structures. This stands in contrast to EEG materials, which are thought to assemble from similar, though less prominent and numerous, precipitates into a more homogeneous structure than RGDEEG gels as a result. The inter-connecting matrix of the RGDEEG gels is therefore more susceptible to rapid bioresorption through this proteolytic assay than that of EEG gels. While β-sheet regions may remain intact in RGDEEG gels, bulk material integrity is lost as the inter-connecting network is resorbed as are the residual β-sheet particles due to the sieving method used as a cutoff for degradation product particle size. This is indicative that it may be possible to use varying levels of RGD in order to further manipulate the structure and bioresorption profile of a silk gel.

Example 8

Fourier-Transform Infrared Spectrum Capture

Silk hydrogels, 23RGD-ethanol-enhanced 4% silk, 3:1 and 10:1, were cast as described above and subjected to proteolytic bioresorption as described above. Additionally, non-bioresorbed control samples were obtained for sake of analysis via FTIR in quantities of 0.5 ml each. Using a Bruker Equinox 55 spectrophotometer (Bruker Optics, Inc., Billerica, Mass.) coupled with a Pike MIRACLE™ germanium crystal (PIKE Technologies, Madison, Wis.), sample absorbance spectra were obtained. Samples were imaged by pressing them upon the crystal via a pressure arm until single sample scans indicated viable signal from the material then performing a 128-scan integration. Resolution was set to 4 $cm^{-1}$ with a 1 $cm^{-1}$ interval from a range of 4000 $cm^{-1}$ to 400 $cm^{-1}$.

Resultant spectra were subjected to analysis via OPUS 4.2 software (Bruker Optics, Inc). A peak-find feature was used to identify peaks between 4000 $cm^{-1}$ and 600 $cm^{-1}$, with the search criteria being automatic selection of local inflection points of a second-derivative, nine-point smoothing function. Program sensitivity was set to 3.5% for all spectra based upon operator discretion regarding magnitude of peaks identified and likely relevance to compound identification and "fingerprinting".

Each of the samples subjected to FTIR analysis exhibited a spectrum with very pronounced peaks at the Amide I band (1600-1700 cm$^{-1}$) (FIG. 8). Additionally, the specific wave numbers of these peaks are consistent between the 23RGD-infused silk fibroin hydrogel and other silk gel groups. All samples exhibit major peaks at ~1622 cm$^{-1}$ and a minor peak/toe region at ~1700 cm$^{-1}$, a pattern associated with a high degree of β-sheet structure within a sample (FIG. 8). There are also similarities across all samples types at the Amide II band with a major peak at ~1514 cm$^{-1}$.

Figure 9:
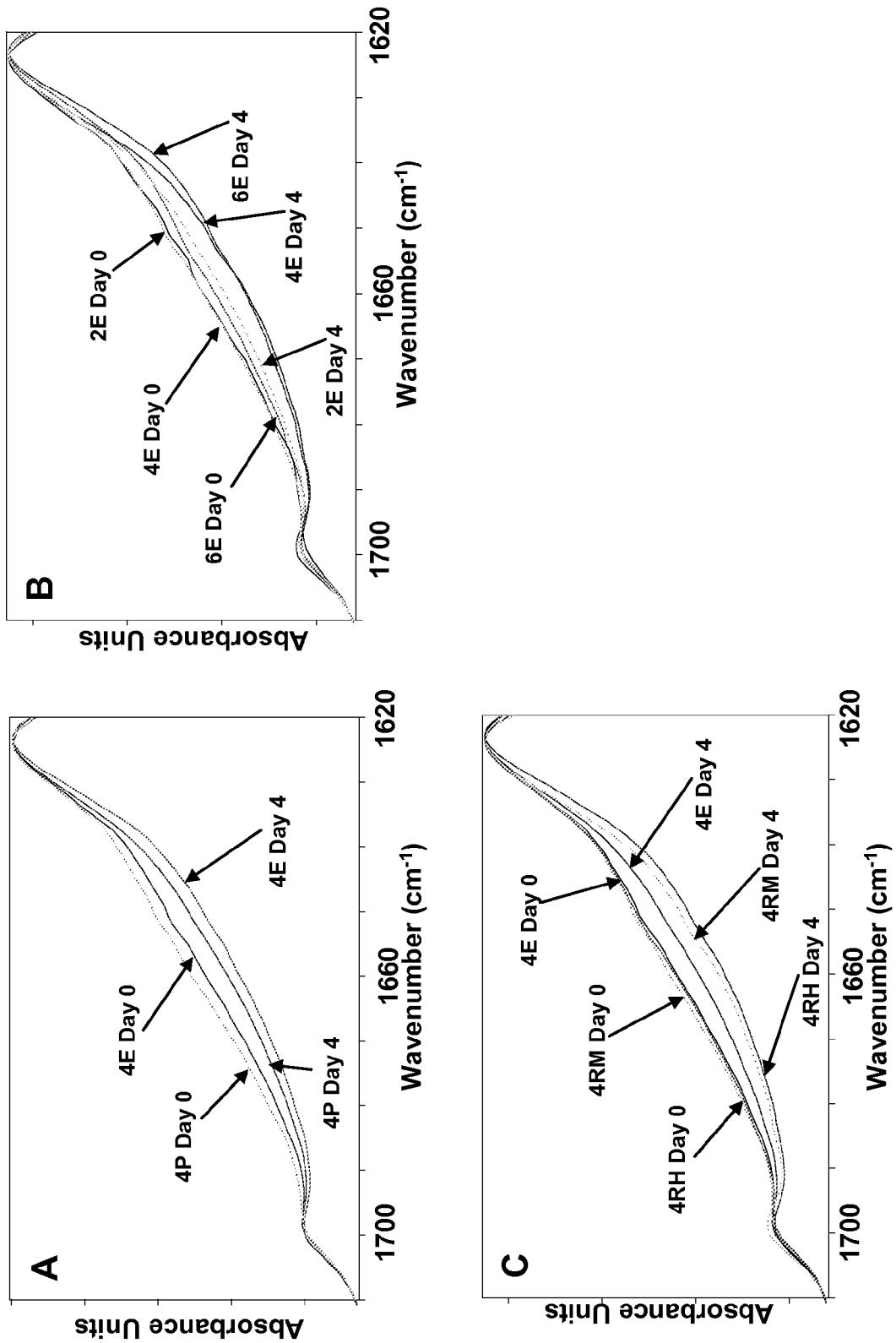
FIG. 9 shows a comparative FTIR spectra illustrating the effects of differing gelation techniques on gel protein structure before (Day 0) and after (Day 4) proteolytic bioresorption. Groups assessed included samples cast by PG and EEG methods (A), cast from increasing silk concentrations (B), and cast using increasing RGD concentrations (C).

Use of the EEG process to produce silk gels did not dramatically impact gel secondary structure but did slightly increase the resistance of the gel formulation to proteolytic bioresorption (FIG. 9A). Evaluation of characteristic FTIR spectra of 4P and 4E gels at Day 0 revealed few distinguishing characteristics as both formulations exhibited a characteristic β-sheet peak around 1622 cm-1 and toe region of β-turn at 1700 cm-1. Each sample also had additional portions of β-sheet, β-turn, α-helix, and unordered random coil at 1677 cm$^{-1}$, 1663 cm$^{-1}$, 1654 cm$^{-1}$, and 1645 cm$^{-1}$ respectively with higher relative quantities of α-helix and random coil appearing in 4P than 4E at Day 0. At Day 4, both samples showed pronounced decreases in 1677 cm$^{-1}$ β-sheet, β-turn, α-helix and random coil signal, though this 4P exhibited this to a greater extent than 4E, indicating preferential resorption of these motifs and greater resistance to this in 4E gels.

Increasing the final silk concentration of EEG gels had little impact on initial gel secondary structure, though there was a pronounced increase in β-sheet structures at Day 4 with greater silk concentrations (FIG. 9B). At Day 0, 2E, 4E, and 6E gels all showed strong signal for 1622 cm$^{-1}$ β-sheet and 1700 cm$^{-1}$ β-turn strong, with 6E having particularly prominent peaks in these regions. Each sample also had additional portions of 1677 cm$^{-1}$ β-sheet, 1663 cm$^{-1}$ β-turn, α-helix, and unordered random coil. At Day 4 all gels showed decreases in 1677 cm$^{-1}$ β-sheet, 1663 cm$^{-1}$ β-turn, α-helix and random coil peaks relative to 1622 cm$^{-1}$ β-sheet and β-turn peaks with this behavior being more marked in 4E and 6E than 2E. The Day 4 6E sample also showed a more stable β-sheet structure indicated by a peak shift to lower wave number at ~1620 cm$^{-1}$.

Pronounced differences in the 23RGD-ethanol-enhanced and ethanol-enhanced spectra only became evident after a four-day period of bioresorption in protease. The day 4 samples exhibited differences primarily in the order of magnitude of certain secondary structure modalities seen through slight differences in FTIR Amide I band shape. At day 4, the 23RGD-ethanol-enhanced samples exhibit higher levels of β-turn structure evidenced by far more pronounced and distinct peaks at ~1700 cm$^{-1}$ while also showing considerably lower levels of α-helix structure (1654 cm$^{-1}$) and unordered random coil (1645 cm$^{-1}$) structures. For example, FTIR spectra from 4E, 4RM and 4RH all show similar structures featuring 1622 cm$^{-1}$ β-sheet and 1700 cm$^{-1}$ β-turn prominently with indications of 1677 cm$^{-1}$ β-sheet, 1663 cm$^{-1}$ β-turn, α-helix, and unordered random coil secondary structures (FIG. 9C). At Day 4, 4RM and 4RH both show a less pronounced 1677 cm$^{-1}$ β-sheet, 1663 cm$^{-1}$ β-turn, α-helix, and random coil component than the 4E sample with 4RH also showing a more stable β-sheet structure, indicated by a peak shift to lower wave number at ~1620 cm$^{-1}$. Additionally, a peak shift occurred in both the 10:1 23RGD-ethanol-enhanced and ethanol-enhanced samples in the β-strand peak at 1622 cm$^{-1}$, indicative of increased β-sheet stability. Considered as a whole, the collective peak shifts and peak magnitudes observed in the spectra at day 4 compared to day 0, all gel types experienced substantial strengthening of β-sheet component, likely due to removal of less-stable α-helix and random coil. These effects were most pronounced in 23RGD-enhanced gel materials, likely due to intrinsic differences in the initial organization of the structural network of the gel materials.

FTIR analysis and comparison of PG, EEG and RGDEEG showed strong behavioral similarities across all gel groups. Each material exhibited β-sheet-dominated secondary protein structures, featuring elements of α-helical and random coil structures and each resorbed in such a fashion that the quantities of β-sheet-rich structure increased relative to α-helical and random coil structures. The selective bioresorption of α-helical and random coil structures indicates that they are likely favorably degraded by proteolysis relative to β-sheet structures, thus the bioresorption profile of a gel might be influenced by altering the balance between β-sheet motifs and the combination of α-helical and random coil structures. An evaluation of ethanol as an accelerant revealed a minimal effect on silk gel structure at Day 0 as both 4P and 4E had high β-sheet contents with α-helical and random coil structures (FIG. 9A). At Day 4 though, there was a slightly greater relative β-sheet content in 4E than 4P samples. This may be caused by structural differences in 4E and 4P formulations that were imperceptible at Day 0 by ATR-FTIR, possibly in the uniformity and homogeneity of the silk gels. It is possible that the same differences hypothesized between EEG and RGDEEG gels derived from their different extents of precipitate/nucleation point formation in early-phase gelation causes differences between PG and EEG materials as well. As PG samples are not accelerated, it is likely that very few nucleation points will form quickly and as a result, the gelation process occurs in a very slow but homogeneous fashion, allowing for an optimal stearic packing of silk molecules throughout the solution volume. This results in a consistent protein structure throughout the final gel volume, corresponding to good bulk material integrity. This would contrast with EEG gels, as the previously postulated nucleation phenomenon associated with RGDEEG materials likely occurs with EEG materials as well, though in a less prominent fashion. This results in a non-uniform distribution of highly organized regions of β-sheet held together by α-helical and random coil structures in the EEG materials relative to the PG materials, with α-helical and random coil degraded more rapidly than β-sheet. This is in keeping with previous studies which have shown that more poorly packed β-sheet structures and α-helix structures are more susceptible to degradation. Increasing silk concentration in EEG gels from 2E to 4E to 6E revealed the most prominent β-sheet structures in 6E at both Day 0 and Day 4 while 2E had considerably more α-helix and random coil at both days than 2E and 4E (FIG. 9B). This would seem to indicate that dilute concentrations of silk in the final hydrogel result in a less densely packed secondary structure, possibly due to stearic freedom within the gel volume relative to 4% and 6% states. This indicates that silk concentration may be used to manipulate the secondary structure of silk gel to influence bioresorption. A study of the effect of increasing RGD concentration indicated that while gels were virtually identical at Day 0, the α-helix structure and unordered random coil in 4RM and 4RH gels were less resilient to bioresorption than in 4E as seen at Day 4 (FIG. 9C). This might also be explained by inhomogeneities within the 4RM and 4RH gels relative to 4E as mentioned previously. This may be particularly likely in light of the formation of precipitates observed in RGDEEG samples. This data may be indicative that RGD or a similar peptide could be used to further tailor the nature of the bioresorption profile of silk gels.

These results indicate that silk gels produced through PG, EEG, and RGDEEG result from a two-phase assembly process consisting of nucleation and aggregation. Silk gels contain predominantly β-sheet structure which is more resistant to in vitro bioresorption than α-helix and random coil. EEG gels form more quickly than PG, likely due to a more rapid precipitation and nucleation event mediated by the effects of ethanol on the solution solvent phase. EEG gels form a non-homogeneous structure likely consisting of localized, initially-precipitated β-sheet regions inter-connected by α-helix and random coil assembled subsequently. RGDEEG gels form a non-homogeneous structure likely consisting of localized, initially-precipitated β-sheet regions inter-connected by α-helix and random coil assembled subsequently. RGDEEG gels reach completion more slowly than EEG gels due to stearic RGD-mediated interference encountered in gel assembly following nucleation. RGDEEG gels are less homogeneous than EEG gels due to these difficulties associated with late-phase assembly.

Example 9

Injectable Gel Processing

Silk hydrogels were prepared as described above in Examples 1-4. Gels were then comminuted by grinding the silk gel to a paste using a stainless steel spatula. Gel formulations including PBS were massed with an SI-215 balance (Denver Instrument, Denver Colo.) and the correct volume percentage of PBS (Invitrogen Corporation, Carlsbad, Calif.) was blended in with the assumption that both the gel and PBS had a density of 1 g/ml. Silk hydrogels to be used for in vivo assessment were subjected to vigorous mechanical pulverization by means of a stainless steel stir rod. When specified as containing a saline component, gels were blended with saline at volumetric ratios based upon the original volume of gel (i.e., prior to mechanical disruption) following pulverizing by the stainless steel bar. This addition of phosphate buffered saline serves to regulate tonicity of the gel as well as improve injectability. Following this initial pulverizing, the gel was further disrupted by means of repeated injection through a 26-gauge needle in order to decrease overall particle size within the gel and improve injectability characteristics. In some samples, gel was further disrupted by means of repeated injection first through an 18 g needle repeatedly until the gel flowed readily, and then the material was then cycled in like fashion through a 23 g needle and 26 g needle.

Example 10

In Vivo Investigation of Silk Hydrogel in Rodent Models

Samples of silk gel which had been processed for implantation or injection in vivo as described in Example 9 were double-bagged with appropriate sterilization bags for gamma irradiation and sterilized by exposure to a dose of 25 kGy of gamma radiation.

In one trial silk hydrogel samples, both 23RGD-enhanced and native were implanted subcutaneously in male Lewis rats having an average weight of 400 g. This was done according to protocol# 86-04 on file with New England Medical Center's Department of Laboratory Animal Medicine (DLAM) and approved by the Institutional Animal Care and Use Committee (IACUC). On the day of surgery, animals were anesthetized via a ketamine/xylazine solution injected IM in the animals' hind legs. Following administration of anesthesia, the skin of the rats was shaved closely and swabbed with alcohol, allowed to dry, swabbed with BETADINE® microbicide (Purdue Pharma, Stamford, Conn.) then draped with sterile towels. In the case of implanted devices, two dorsal midline incisions were made directly over the spine, the first 0.5 cm below the shoulders and the second 2.5 cm above the pelvic crest, each 1 cm long each. The incisions were expanded into 1 cm deep pockets using a blunt dissection technique beneath the panniculus carnosus at each side yielding 4 potential implant sites. Implants, 3 per animal; each 1 cm×1 cm×0.3 cm in size were inserted into the pockets without fixation with the final site undergoing the same dissection but replacing the implant with 0.5 mL of sterile saline solution. The skin was closed with interrupted absorbable sutures. Depending on study, samples were harvested at 7 days, 14 days, 28 days, and/or 57 days after implantation surgery. Gross observations were collected semi-weekly regarding implant site appearance. After sample harvest, gross observations of the implants were conducted and samples were processed for histological evaluation. Analysis of histology slides was provided by a trained veterinary pathologist.

Sections were scored for presence (0=none, 1=present) of implant mineralization, cyst formation, fibrosis, sebaceous cell hyperplasia, and focal follicular atrophy. Additionally, the density of inflammatory response (0=none . . . 5=extensive) and extent epidermal hyperplasia (0=none . . . 3=extensive) were graded. These data were reported as percentages of the highest score possible for the group of slides. Sections were also examined for presence of any particular characteristic cell types including lymphocytes, neutrophils, eosinophils, mononuclear giant cells, macrophages, and fibroblasts. Additional commentary relevant to the host response was included at the discretion of the reviewing pathologist. Prism 4.03 (GraphPad Software Inc., San Diego, Calif.) was used to perform analysis of variance (ANOVA) with a significance threshold set at $p \leq 0.05$. One-way ANOVA was used to compare differences average extrusion forces for comminuted gels. For all tests, Tukey's post-hoc test was also performed for multiple comparisons.

Figure 10:
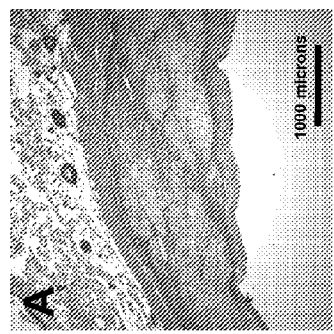
FIG. 10 shows representative micrographs of H&E-stained histological sections collected from silk gels implanted subcutaneously in rats. Samples of 4% silk fibroin hydrogel formed by passive gelation (4P), 4% silk fibroin hydrogel formed by ethanol-enhanced gelation (4E), and 6% silk fibroin hydrogel formed by ethanol-enhanced gelation (6E) were compared at 7 days (A, B, and E respectively) with 4E and 6E samples compared again at days 28 (C and F) and 57 (D and G).
Figure 10:
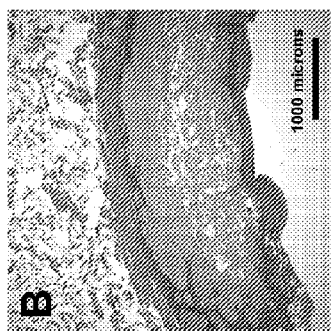
Figure 10:
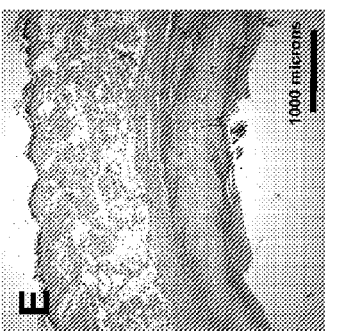
Figure 10:
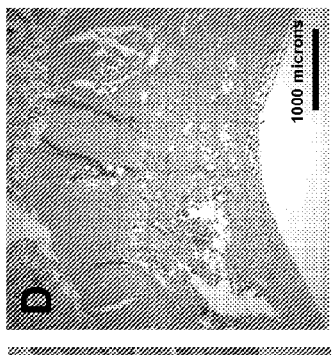
Figure 10:
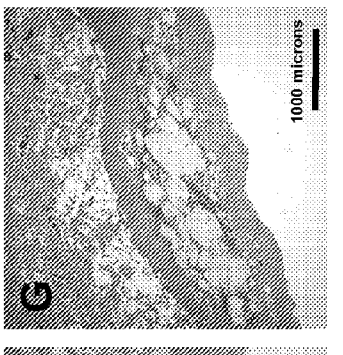
Figure 10:
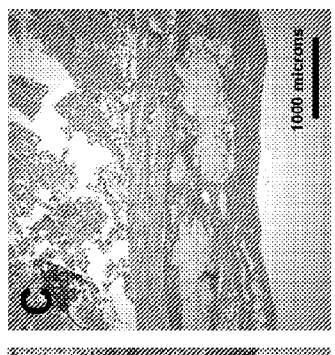
Figure 10:
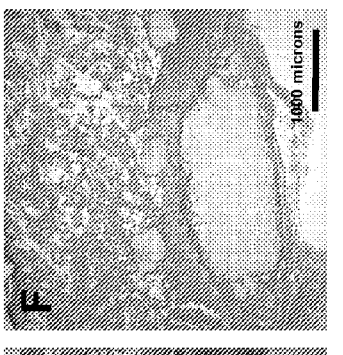

Table 2 lists the formulations of silk gel, both 23RGD-ethanol-enhanced and ethanol-enhanced developed and assessed intradermally in a rat model. Silk gels explanted from rats at Day 7 were visibly well-defined and easily identifiable with no gross indications of edema, erythema, or transdermal elimination of material. It was not possible to differentiate sites of PBS control implantation from surrounding tissue. H&E sections of 4% silk fibroin hydrogels formed by passive gelation (4P), 4% silk fibroin hydrogels formed by ethanol-enhanced gelation (4E) and 6% silk fibroin hydrogels formed by ethanol-enhanced gelation (6E) all appeared similar, with mild inflammation in all cases characterized by lymphocytes, macrophages, some neutrophils and fibroblasts (FIG. 10). Cellular infiltration was observed in all sample types with complete penetration in 4P and peripheral ingrowth to a depth of about 100 μm in both EEG gels with no evidence of cyst formation observed. In all gels, early bioresorption was indicated by implant edge erosion with residual implant material remaining localized into large lakes. Host integration of implanted gel had progressed in Day 28 samples of 4E and 6E evidenced by greater cellular ingrowth into the material with complete implant penetration in 4E samples and robust peripheral ingrowth in 6E samples. The cellular response at this time point was characterized by fibroblasts, lymphocytes and macrophages with the addition of a few multi-nucleated giant cells.

TABLE 2

Silk Hydrogel Formulations

| Group Name | Silk Concentration | Enhancer | Saline Component |
|---|---|---|---|
| 4E10 | 4% | 90% Ethanol | 10% |
| 4R10 | | 90% Ethanol, 1:1 23RGD | |
| 4RH10 | | 90% Ethanol, 3:1 23RGD | |
| 4E25 | | 90% Ethanol | 25% |
| 4R25 | | 90% Ethanol, 1:1 23RGD | |
| 4RH25 | | 90% Ethanol, 3:1 23RGD | |
| 6E10 | 6% | 90% Ethanol | 10% |
| 6R10 | | 90% Ethanol, 1:1 23RGD | |
| 6E25 | | 90% Ethanol | 25% |
| 6R25 | | 90% Ethanol, 1:1 23RGD | |
| 6RH25 | | 90% Ethanol, 3:1 23RGD | |

Day 57 samples of 4E and 6E showed continued host bioresorption of the gel material as there was little residual 4E and while 6E remained visible in large, intact lakes, the gel had been completely penetrated with host tissue. The host response to 4E had dramatically decreased in cellularity between Day 28 and Day 57 with very little evidence of hypercellularity at Day 57 with some scattered macrophages and fibroblasts around the implant site. The pathology of the host response of 6E was similar to the Day 28 response to 4E, with fibroblasts as the predominant cell type and scattered lymphocytes, macrophages and multi-nucleated giant cells. This was viewed as a low-grade, persistent, fibrotic-type inflammatory response to the material.

Figure 11:
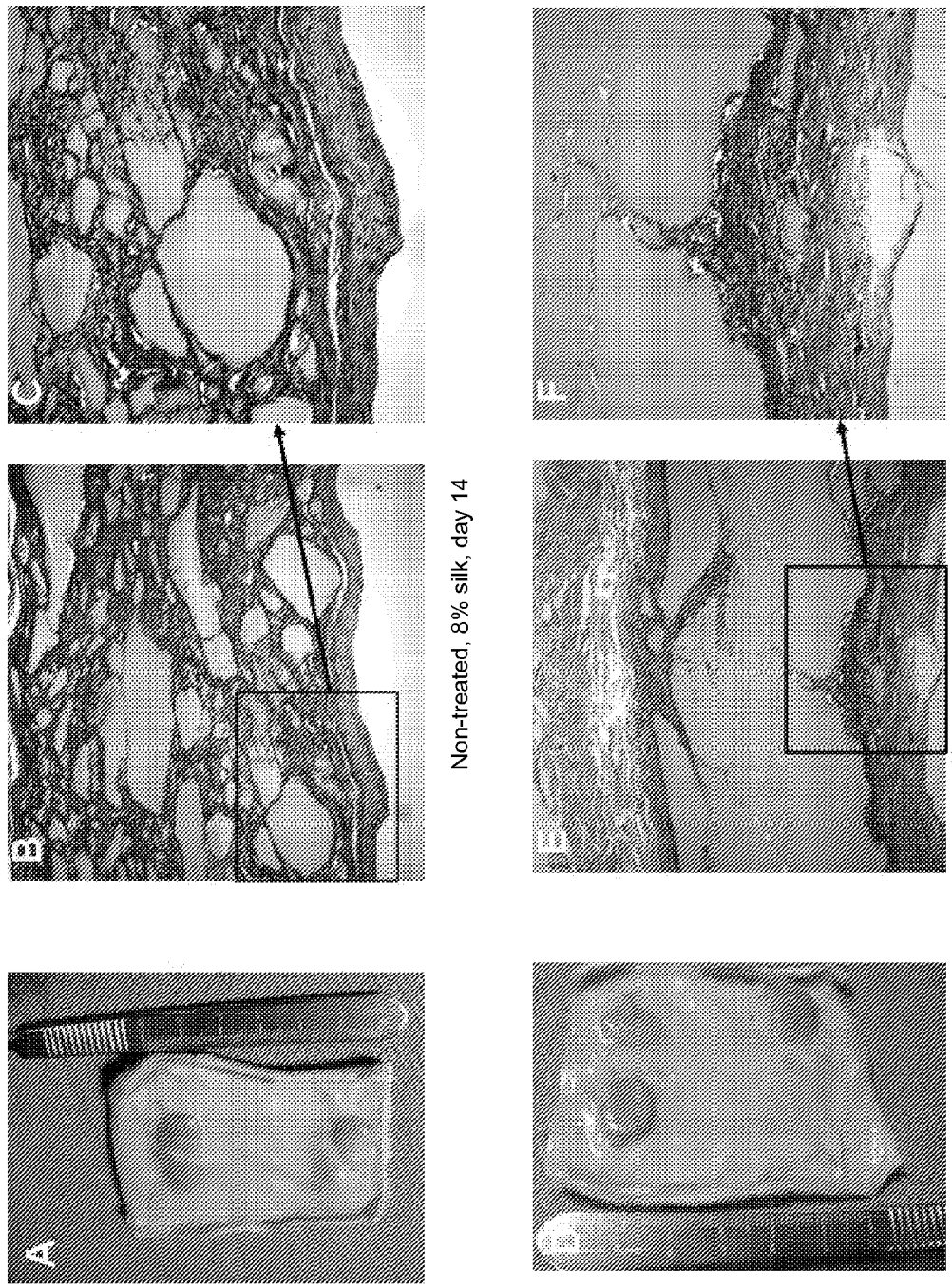
FIG. 11 shows representative gross photographs of 8% silk fibroin hydrogel devices both unmodified (A) and 23RGD-enhanced (D) after a two-week subcutaneous incubation in Lewis rats. Also shown are micrographs resultant from H & E stains of the unmodified (B and C) and 23RGD-coupled (E and F) samples at 10× and 20× magnification. These gross images coupled with the histological micrographs provide evidence of a less extensive inflammatory response during early device integration being associated with 23RGD-enhanced gel than non-23RGD-enhanced gel.

Samples of 23RGD-enhanced gel exhibited a less robust inflammatory response at the 14 day time point in comparison to non-23RGD-enhanced gel (FIG. 11). This is observed through an appreciable decrease in hyper-cellularity proximal to the gel implant and an accompanying decrease in the fragmentation of the implant material. It is possible that this improvement in implant integrity is due to a less robust foreign body response by the host animal and it may also be evidence that there is less mechanical contraction of the implant site, a commonly observed phenomenon with biomaterials including the "RGD" motif. These effects indicate that 23RGD-enhancement of silk gels leads to a more biocompatible material with better implant outcomes.

In a second trial, intradermally-injected samples of silk hydrogel, both ethanol enhanced and 23RGD-ethanol enhanced and relevant control materials were investigated using male Hartley guinea pigs. This was done according to protocol# 29-05 on file with New England Medical Center's Department of Laboratory Animal Medicine (DLAM) and approved by the Institutional Animal Care and Use Committee (IACUC). Briefly, male Hartley guinea pigs weighing 300-350 g were anesthetized via a ketamine/xylazine cocktail injected intramuscularly into the animals' hind legs. The dorsal skin of the guinea pigs was then shaved closely and swabbed with alcohol, allowed to dry, swabbed with BETADINE® microbicide or Chloraprep (Enturia, Inc., Leawood, Kans.), then draped with sterile towels. A 50 μL volume of the desired material was injected through a 26 g needle at six different sites along the left side of the animal's back. Further injections of an appropriate silk gel control were made at the six contralateral sites. Explanation of the silk gels was performed at 28 days after implantation. Gross observations were collected semi-weekly regarding implant site appearance. After sample harvest, gross observations of the implants were conducted and samples were processed for histological evaluation. Analysis of histology slides was provided by a trained veterinary pathologist. Scoring and statistical analysis was performed as described above.

Table 3 lists the formulations of silk gel, both 23RGD-ethanol-enhanced and ethanol-enhanced developed and assessed intradermally in a guinea pig model in a twenty-eight day screen. Although no statistically significant differences were identified, the data for both gross observations and histology (Tables 4 and 5) indicate a general trend supporting the previous data that 23RGD-enhancement of gel improves material biocompatibility. Among sites implanted with silk gel, gross outcomes varied. Ulceration and hair loss rates were lower in groups with 25% PBS compared to 10% saline, 6% silk compared to 4% silk and RGDEEG casting as compared to just EEG casting (Table 4). Site redness rates followed a similar pattern with the exception that RGDEEG samples induced more site redness than EEG samples. All silk gels showed evidence of epidermal cyst formation, fibrosis, epidermal hyperplasia and pronounced inflammation with traces of follicular atrophy in all EEG samples. Sebaceous cell hyperplasia was present to a limited extent in all formulations with the exception of 6% silk, 10% saline, 1:1 23RGD (Table 5). This is particularly evident in the case of silk gels of 4% silk with 25% saline added and either enhanced with an ethanol-based enhancer or an 23RGD-ethanol-based enhancer, and more specifically, in the case of site ulcerations (Table 5). This material indicated strong improvements with increasing 23RGD concentration in the number of sites ulcerating throughout the course of the trial. These results are indicative that use of 23RGD in conjunction with an ethanol enhancer provides an improved outcome when compared to an ethanol enhancer alone.

TABLE 3

Silk Hydrogel Formulations

| Group Name | Silk Concentration | Enhancer | Saline Component |
|---|---|---|---|
| 4E10 | 4% | 90% Ethanol | 10% |
| 4R10 | | 90% Ethanol, 1:1 23RGD | |
| 4E25 | | 90% Ethanol | 25% |
| 4R25 | | 90% Ethanol, 1:1 23RGD | |
| 4RH25 | | 90% Ethanol, 3:1 23RGD | |
| 6E10 | 6% | 90% Ethanol | 10% |
| 6R10 | | 90% Ethanol, 1:1 23RGD | |
| 6E25 | | 90% Ethanol | 25% |
| 6R25 | | 90% Ethanol, 1:1 23RGD | |

TABLE 4

Gross Evaluation of Guinea Pigs

| Group Name | Site Redness | Hair Loss | Palpability | Ulceration |
|---|---|---|---|---|
| 4E10 | 38% | 58% | 65% | 33% |
| 4R10 | 57% | 49% | 67% | 33% |
| 4E25 | 28% | 34% | 49% | 28% |
| 4R25 | 44% | 34% | 64% | 17% |
| 4RH25 | 50% | 23% | 66% | 6% |
| 6E10 | 63% | 52% | 68% | 33% |
| 6R10 | 78% | 51% | 68% | 22% |
| 6E25 | 33% | 31% | 69% | 11% |
| 6R25 | 56% | 30% | 68% | 13% |
| HYLAFORM ™ | 6% | 12% | 63% | 0% |
| ZYPLAST ™ | 17% | 10% | 52% | 0% |

TABLE 5

Histological Evaluation of Guinea Pigs

| Group Name | Epidermal Cyst Formation | Fibrosis | Inflammation | Epidermal Hyperplasia | Follicular Atrophy | Sebaceous Hyperplasia |
|---|---|---|---|---|---|---|
| 4E10 | 22% | 100% | 70% | 59% | 11% | 22% |
| 4R10 | 74% | 100% | 62% | 67% | 0% | 14% |
| 4E25 | 50% | 100% | 69% | 67% | 13% | 13% |
| 4R25 | 29% | 100% | 39% | 62% | 0% | 14% |
| 4RH25 | 14% | 100% | 64% | 50% | 0% | 43% |
| 6E10 | 44% | 100% | 70% | 56% | 11% | 33% |
| 6R10 | 25% | 100% | 63% | 38% | 0% | 0% |
| 6E25 | 30% | 100% | 60% | 40% | 10% | 20% |
| 6R25 | 29% | 100% | 64% | 33% | 0% | 14% |
| HYLAFORM ™ | 0% | 0% | 3% | 6% | 0% | 0% |
| ZYPLAST ™ | 0% | 25% | 28% | 31% | 0% | 0% |

Figure 12:
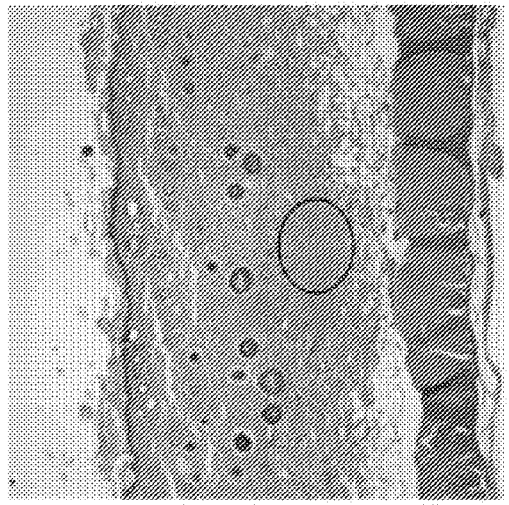
FIG. 12 shows representative histology collected from a thirteen-week study of 4% 3:1 23RGD-enhanced silk hydrogel blended with 25% saline (left panels, H&E stain Trichrome stain) and ZYPLAST™ (right panels H&E stain, Trichrome stain) and injected into the intradermis of guinea pig. Each material type exhibited some clear evidence of implanted device in 75% of their respective implant sites. These micrographs indicate strong similarities not only between the long-term bioresorption characteristics but also long-term host tissue response between collagen-derived biomaterials and this particular 23RGD-enhanced silk hydrogel formulation.
Figure 12:
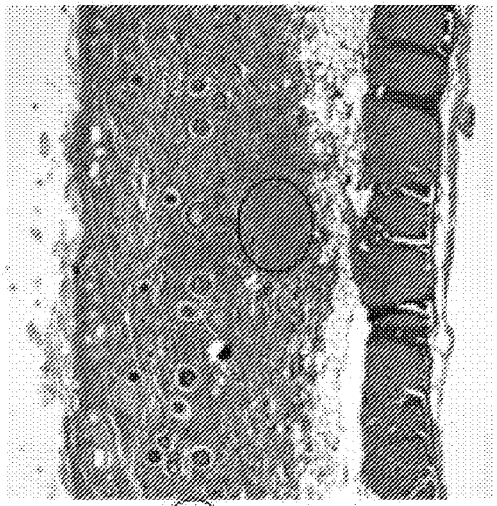
Figure 12:
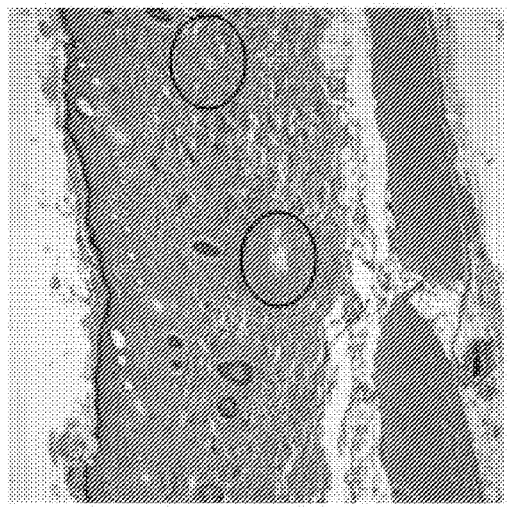
Figure 12:
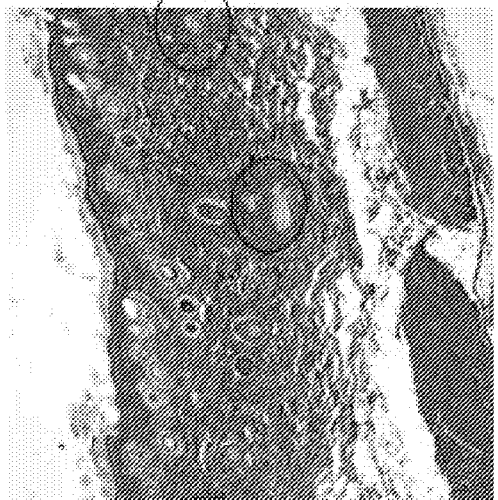

A third trial also used male Hartley guinea pigs to investigate intradermally injected samples of silk hydrogel as described above, comparing samples of 4% and 6% silk, 25% saline 3:1 23RGD-ethanol enhanced silk gels with a collagen-based control material, ZYPLAST™ (Allergan Inc., Irvine Calif.) and HYLAFORM™ (Allergan Inc., Irvine Calif.). Explanation of the silk gels was performed at 92 days after implantation. Gross observations were collected semi-weekly regarding implant site appearance. After sample harvest, gross observations of the implants were conducted and samples were processed for histological evaluation. During the course of the 92 day trial, none of the 24 implant sites, either 23RGD-ethanol-enhanced hydrogel or ZYPLAST™, ulcerated. Histology revealed that 75% of all ZYPLAST™ sites had residual material as did 75% of all 23RGD-ethanol-enhanced silk gel sites (both 4% and 6%). Both materials exhibited very similar chronic phase cellular responses, as the sites were characterized by a mild fibrotic reaction with abundant deposition of collagen in and around the implant site (FIG. 12). The collagen appears less ordered than does that in the surrounding dermal reticulum based upon the color density when viewed with Trichrome staining and also when viewed under polarized light. Silk gel sites had similar palpability scores to both control materials but exhibited higher rates of site redness, hair loss and ulceration than did ZYPLAST™ and HYLAFORM™. These results not only reinforce that 23RGD-ethanol-enhanced silk gel is biocompatible, but also indicate that it is comparable to collagen biomaterials in terms of its persistence and long-term behavior in vivo.

Figure 13:
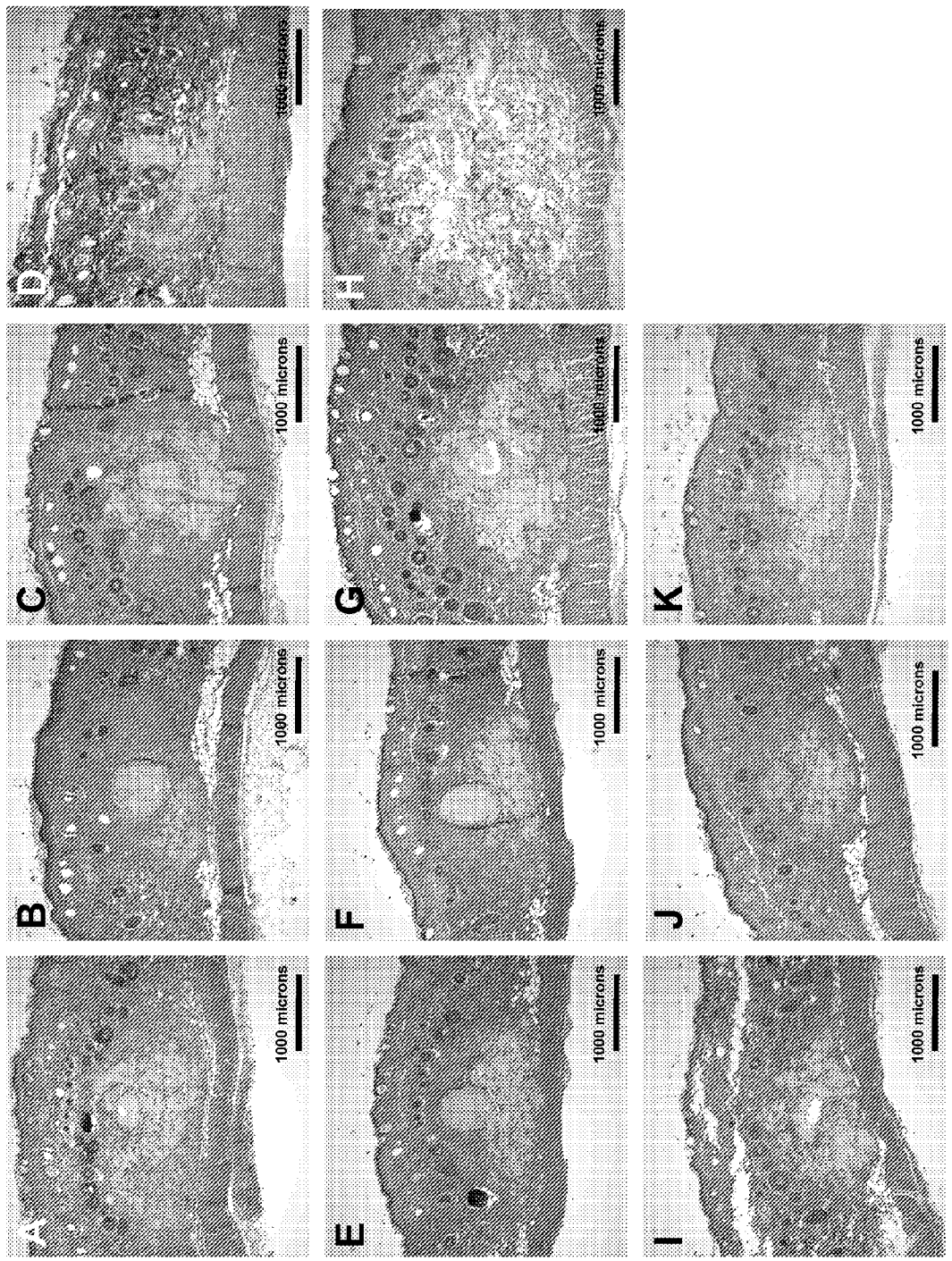
FIG. 13 shows representative micrographs of H&E-stained histological sections collected from Day 28 explants of 4% silk fibroin, 10% saline (A); 4% silk fibroin, 1:1 23RGD, 10% saline (B); 6% silk fibroin, 1:1 23RGD, 10% saline (C); ZYPLAST™ (D); 4% silk fibroin, 25% saline (E); 4% silk fibroin, 1:1 23RGD, 25% saline (F); 6% silk fibroin, 10% saline (G); HYLAFORM™ (H); 6% silk fibroin, 25% saline (I); 4% silk fibroin, 3:1 23RGD, 25% saline (J); and 6% silk fibroin, 1:1 23RGD, 25% saline (K).

ZYPLAST™ exhibited no epidermal cysts, follicular atrophy, or sebaceous cell hyperplasia, though it did show small levels of fibrosis, inflammation and epidermal hyperplasia. Examination of histological sections showed residual silk gel material which stained in a mildly eosinophilic fashion and appeared as large lakes of material at a central location with smaller masses of material distributed more widely throughout the reticular dermis (FIG. 13). These smaller masses were typically surrounded by fibroblasts and macrophages with occasional multi-nucleated giant cells present. Eosinophils were located proximal to these smaller masses of implant as well. In general, host response to the silk fibroin gels was characterized as mildly fibrotic and included populations of fibroblasts, lymphocytes, macrophages, multi-nucleated giant cells and eosinophils. Little difference was evident between silk gel types except in terms of the extent of eosinophilia. Larger eosinophil populations were observed for 6% as compared to 4% silk gels and were also observed to increase with RGD concentration in the silk gel samples in both 4% and 6% groups. ZYPLAST™ exhibited strong eosinophilic staining and was distributed as large lakes in the reticular dermis with smaller masses throughout the area. Hypercellularity near the injection site was lessened in ZYPLAST™ samples when compared to silk gel. Fibroblasts, lymphocytes, macrophages, multi-nucleated giant cells and eosinophils were present with less tendency to localize at the implant periphery. HYLAFORM™ samples examined showed many very small masses of material throughout the reticular dermis. HYLAFORM™ exhibited no epidermal cysts, fibrosis, follicular atrophy, or sebaceous cell hyperplasia with extremely limited instances of inflammation and epidermal hyperplasia. There was no observable hypercellularity near the implanted material or other evidence of inflammation at the implant sites.

Figure 14:
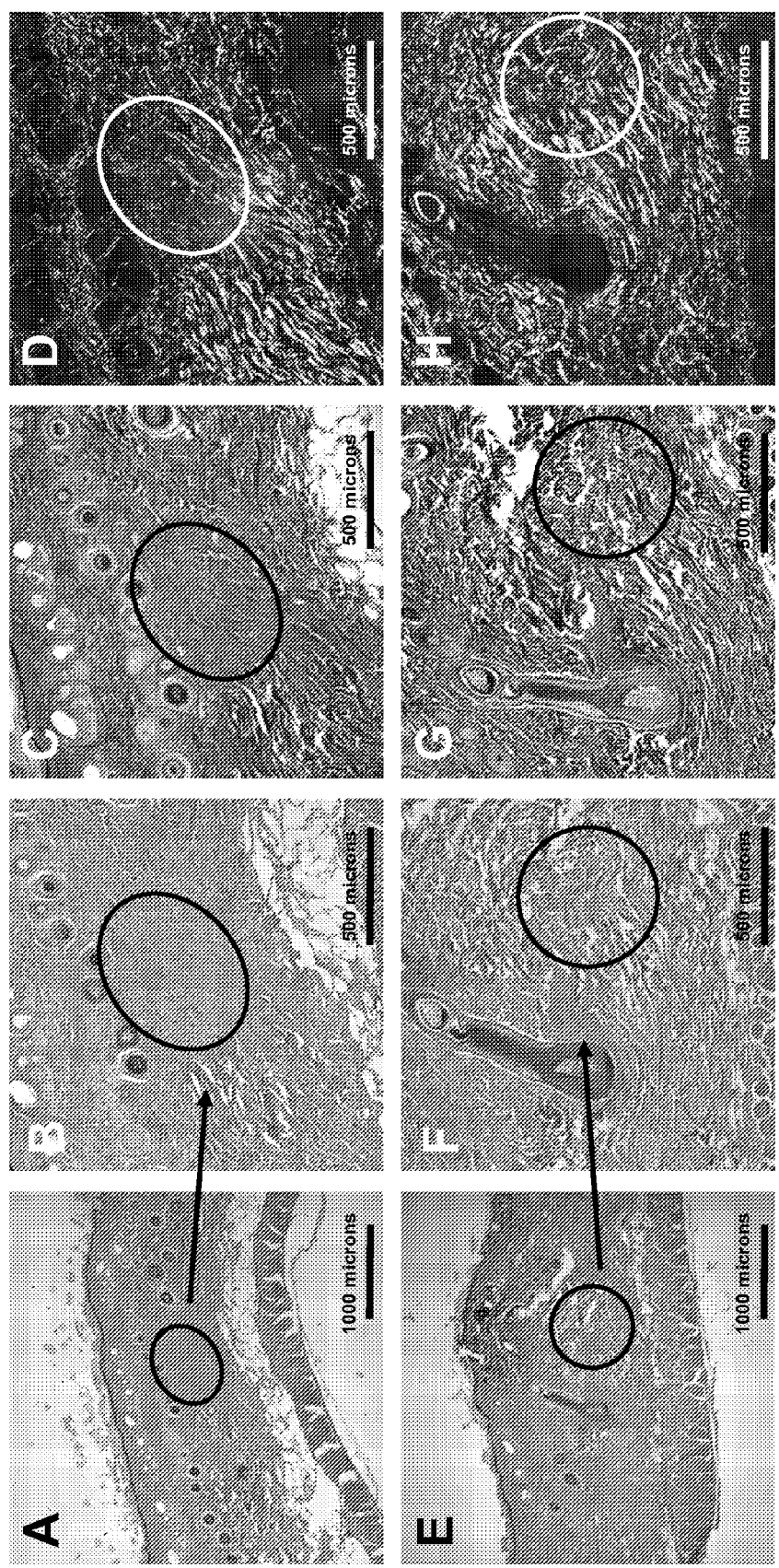
FIG. 14 shows representative micrographs of Day 92 histological sections of 4% silk fibroin, 3:1 23RGD, 25% saline (A-D) and ZYPLAST™ samples (E-H) stained with H&E at 4× (A and E), 10× (B and F), stained with Masson's Trichrome at 10× (C and G) and under polarized light at 10× (D and H).

At day 92, histological evaluation of 4% silk fibroin hydrogel, 3:1 23RGD, 25% saline (4RH25) samples and ZYPLAST™ samples showed similar material persistence and host response (FIG. 14). Very little implant material remained visible in the dermis of the animals with no hypercellularity present at this time point, evidence of hyperplasia or cellular inflammation. The eosinophils found at day 28 in the ZYPLAST™ and silk gel samples were not observed at day 92. Of particular interest, 4RH25 also exhibited residual disruption to the reticular dermis in the form of an irregular collagen pattern near the implant material. The disorganization of the collagen was seen as a region of stained collagen seen to be devoid of the typical cross-hatch pattern of normal reticular dermis (FIG. 14C). This disorganization was confirmed when viewing the histological sections under polarized light with the disorganized collagen appearing as an interruption in the birefringence associated with the surrounding reticular dermis (FIG. 14D).

Example 11

Enhanced Injectable Gel Formulation

Silk hydrogels were prepared as described above in Examples 1-4. Once processed, the gels were sized into coarse or fine particles using a sieving step (Table 6). Gel materials were pressed through a 316SS stainless steel wire cloth sieve with a stainless steel spatula and into clean polystyrene Petri dishes. Sieves with gap sizes of 711 μm×711 μm, 295 μm×295 μm, 104 μm×104 μm and 74 μm×74 μm were used. After passing through the 74 μm×74 μm gap sieve, the material was considered processed to a "coarse" state. Samples to be processed to a "fine" state were further forced through a 43 μm×43 μm sieve in the same fashion. This sieving was conducted four separate times for each sample type, each sieving using an approximate quantity of 0.5 mL of gel material.

TABLE 6

Particle sizing

| Nominal Silk Mass Percentage | 23RGD Molar Ratio with Silk | Fineness | Group Name |
|---|---|---|---|
| 2% | 1:1 | Fine | 2RF |
| 4% | 0 | | 4F |
| | 1:1 | Coarse | 4RC |
| | 3:1 | Fine | 4RF |
| | 10:1 | | RHRF |
| | | | 4VHRF |
| 8% | 1:1 | Coarse | 8RC |
| | | Fine | 8RF |

Samples of silk gel material (N=4 of each type) were evaluated under light microscopy. Briefly, a 100 mg portion of silk gel or control device was massed using an SI-215 Summit series balance. This material was loaded into the open back end of a 3 mL syringe using a stainless steel spatula. The plunger was replaced in the syringe, an 18 g needle was attached to the end of the syringe and approximately 900 µL of ultra-pure water was drawn up. This mixture of water and silk gel was mixed through gentle shaking. After mixing to suspend evenly, a sample of approximately 30 µL of dilute silk gel was placed on a 75 mm×25 mm single frosted, pre-cleaned micro slide (Fisher Scientific Co., Waltham, Mass.) and covered with a 22 mm×40 mm premium cover glass (Corning Inc., Corning, N.Y.). This sample slide was then be imaged with a microscope. Sample slides were imaged using a System Microscope Model BX41 (Olympus, Melville, N.Y.) in conjunction with a Microscope PC MACROFIRE™ Model S99831 Camera (Optronics, Goleta, Calif.) and PICTUREFRAME™ 2.1 software (Optronics, Goleta, Calif.). Briefly, slides were scanned for clearly separated gel particles using the 4× objective lens and locations determined for a series of 3 representative images of the sample slide. Each of these locations was imaged after first switching the microscope objective lens to 10×. Micrograph image files were subjected to analysis with IMAGE-PRO® Plus 5.1 software (Media Cybernetics, Inc., Silver Spring, Md.). Image files were checked for particle size distribution, average particle size, average aspect ratio, maximum particle size, minimum particle size and standard particle size deviation. A compilation of the data is presented in Table 7.

TABLE 7

Particle Comminution Data

| Group Name | Min to Max Object Area ($\mu m^2$) | Mean Object Area ($\mu m^2$) |
|---|---|---|
| 2RF | 5.33 to $1.32 \times 10^4$ | 52.43 ± 261.82 |
| 4F | 5.33 to $8.07 \times 10^3$ | 27.82 ± 129.34 |
| 4RC | 5.33 to $8.52 \times 10^3$ | 38.41 ± 196.67 |
| 4RF | 5.33 to $5.29 \times 10^3$ | 34.12 ± 135.31 |
| 4HRF | 5.33 to $7.51 \times 10^3$ | 40.62 ± 166.61 |
| 4VHRF | 5.33 to $3.14 \times 10^3$ | 35.4 ± 105.43 |
| 8RC | 5.33 to $8.04 \times 10^3$ | 46.57 ± 225.43 |
| 8RF | 5.33 to $2.85 \times 10^3$ | 35.26 ± 129.63 |
| ZYPLAST ™ | 5.33 to $1.95 \times 10^3$ | 22.08 ± 41.71 |

Examination of the particles under light microscopy revealed some clumped gel particles which were removed from particle sizing data manually. Particle sizes ranged from 5.3 to $1.3 \times 10^4$ $\mu m^2$, comparable in range to commercially available ZYPLAST™ which ranged from 5.3 to $1.95 \times 10^3$ $\mu m^2$. The data also revealed mean particle sizes ranging from 27.8 $\mu m^2$ to 52.4 $\mu m^2$, again, comparable to ZYPLAST™ with a mean particle size of 22.1 $\mu m^2$. These data illustrate that silk gel may be successfully comminuted to small and functionally useful particle sizes in a fashion similar to presently utilized injectable gel materials. The basic forced-sieving method could easily be replaced with more sophisticated, reproducible methods for purposes of scale-up.

After comminution and blending, samples of silk gel emulsions were subjected to extrusion force testing. Gel materials prepared as described in Examples 1-4 were blended with appropriate ratios of saline in order to evaluate injection (extrusion) force profiles relative to a control material, ZYPLAST™ (Table 8). This was accomplished by massing 5 g of gel material in a large weighing boat using an SI-215 balance (Denver Instrument, Denver, Colo.). An appropriate quantity of saline will be added to constitute the correct volume percentage making the assumption that both the gel material and saline have a density of 1 g/mL. This material was then blended to an even consistency using a stainless steel spatula and loaded into the back end of a 10 mL syringe with an 18 g needle attached for subsequent use.

TABLE 8

Silk Gel Injection Force Profile Generation

| Nominal Silk Mass | 23RGD Molar Ratio with Silk | Fineness | Saline Content | Group Name |
|---|---|---|---|---|
| 2% | 1:1 | Fine | 25% | 2RF25 |
| 4% | 0 | | 25% | 4F25 |
| | 1:1 | Coarse | 25% | 4RC25 |
| | | Fine | 0% | 4RFO |
| | | | 25% | 4RF25 |
| | | | 50% | 4RF50 |
| | 3:1 | | 25% | 4HRF25 |
| | 10:1 | | 25% | 4VHRF25 |
| 8% | | Fine | 25% | 6RF25 |

Figure 15:
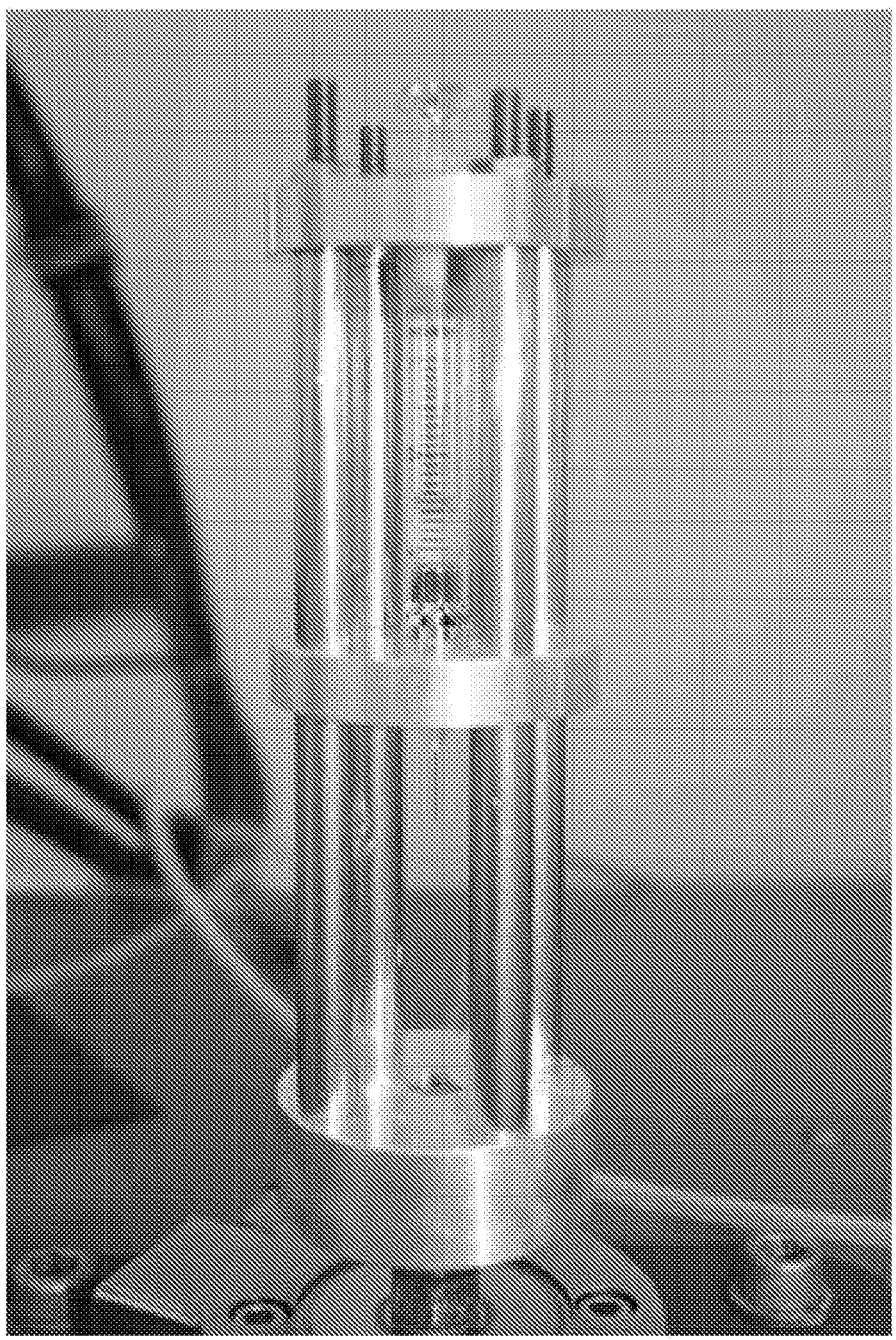
FIG. 15 is a photograph of a custom-built testing jig used in conjunction with an Instron 8511 (Instron Corporation, Canton Mass.) in conjunction with Series 1× software and a 100 N load cell for characterizing the injection forces associated with forcing silk gel through a 30 g needle.
Figure 16:
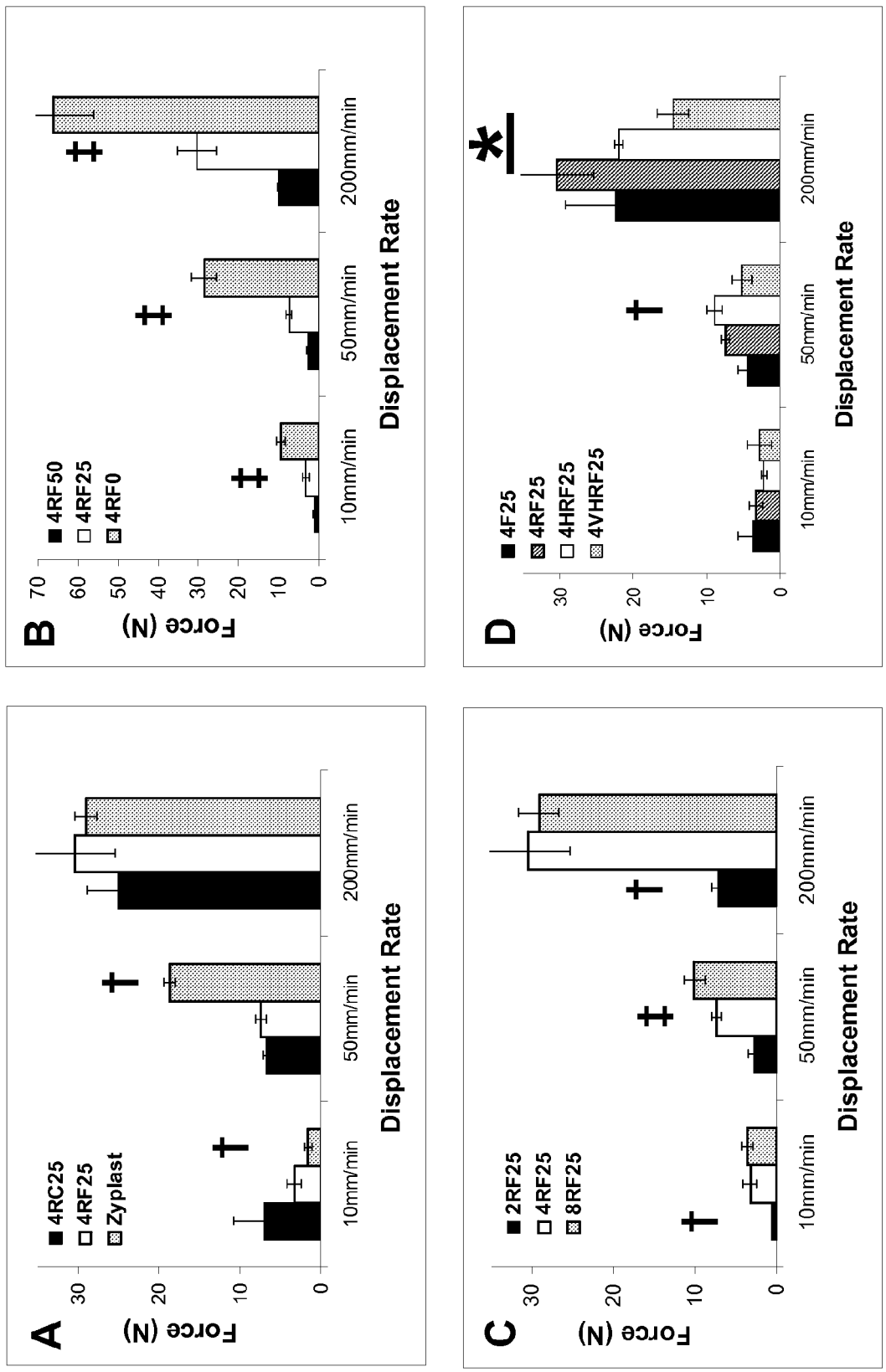
FIG. 16 illustrates the average extrusion force data from mechanical testing of various silk gel formulations illustrating the effects of changing comminution method (A), saline concentration (B), silk concentration (C), and RGD content (D). Values are reported as an average of n=4 tests at each displacement rate with standard deviation illustrated as error bars. * Samples differ significantly, $p<0.05$; † sample differs significantly from all others in group at same strain rate; ‡ all samples in group differ significantly from all others in group at same strain rate.

These samples were tested using an Instron 8511 (Instron Corp., Canton, Mass.) in conjunction with Series IX software and a custom-designed aluminum frame attached to a 100 N load cell (FIG. 15). For the material testing, 1 mL of the sample material of interest was loaded into a 1 mL gas-tight glass syringe. The sample syringe was mounted in the custom-designed aluminum frame mounted on the Instron unit and the material extruded. The sample was then checked for the force required to extrude the gel at each of 3 strain rates, 10 mm/minute, 50 mm/minute, and 200 mm/minute with total actuator displacement set at 7 mm. A series of four tests were run on each material type at each piston displacement rate. Load-displacement data was collected at a frequency of 100 Hz and are presented as the mean±the standard deviation of the 4 average extrusion forces experienced of each gel type at each strain rate. The average extrusion force was defined as the average load measured in the plateau region of the load-displacement curve resultant from each extrusion test. The data were reported as the average amount of force required for extrusion of the sample material and are compiled in Table 9 and FIG. 16.

TABLE 9

Average Force (N) to Extrude Silk Gel from 30 g Needle

| Group Name | Plunger Displacement Rate | | | | | |
|---|---|---|---|---|---|---|
| | 10 mm/min | | 50 mm/min | | 200 mm/min | |
| | Ave | Stdev | Ave | Stdev | Ave | Stdev |
| 2RF25 | 0.6 | 0.0 | 2.9 | 0.6 | 7.3 | 0.7 |
| 4RF25 | 3.7 | 2.0 | 4.5 | 1.3 | 22.4 | 6.7 |
| 4RD25 | 7.1 | 3.7 | 6.7 | 0.5 | 25.1 | 3.9 |
| 4RF0 | 9.5 | 1.0 | 28.5 | 3.1 | 66.2 | 10.0 |
| 4RF26 | 3.2 | 0.9 | 7.4 | 0.6 | 30.4 | 5.0 |
| 4RF50 | 1.2 | 0.2 | 2.7 | 0.1 | 10.1 | 0.3 |
| 4HRF25 | 2.2 | 0.4 | 8.9 | 1.0 | 22.0 | 0.6 |
| 4VHRF25 | 2.8 | 1.6 | 5.2 | 1.4 | 14.6 | 2.1 |
| 8RF25 | 3.6 | 0.7 | 10.1 | 1.3 | 29.2 | 2.4 |
| ZYPLAST™ | 1.6 | 0.5 | 18.7 | 0.7 | 29.1 | 1.4 |

A comparison between milling techniques revealed that there were no significant differences between 4RC25 and 4RF25, having average extrusion forces of 7.1±3.7N and 3.2±0.9N at 10 mm/min, 6.7±0.5N and 7.4±0.6N at 50 mm/min, and 25.1±3.9N and 30.4±5.0N at 200 mm/min respectively (Table 6, FIG. 16A). Both of these formulations differed significantly (p≧0.05) from ZYPLAST™ at strain rates of 10 and 50 mm/min, which had extrusion forces of 1.6±0.5 N, 18.7±0.7 N, and 29.1±1.4 N at 10, 50, and 200 mm/min strain rates.

Data regarding the extrudability of silk gel formulations clearly illustrated that the addition of saline as a carrier fluid to the comminuted silk particles offers an improved degree of extrudability, substantially reducing the force necessary to extrude silk gel at all strain rates. Adding increasing concentrations of saline to the comminuted silk gels significantly decreased the extrusion force required for silk gels at each strain rate, with gels again exhibiting shear-thickening behavior (Table 9, FIG. 16B). At all strain rates, 4RF0 required significantly more force to extrude than 4RF25, which in turn required significantly more than 4RF50. At a strain rate of 10 mm/min, 4R0, 4R10, and 4R25 showed a significant decrease (p≧0.05) in extrusion force with increasing PBS concentration, having average forces of 9.5±3.1 N, 6.1±0.5 N, and 4.7±0.7 N respectively (Table 9). At 50 mm/min, these relationships were more pronounced with average extrusion forces of 14.0±0.9 N, 5.4±0.7 N, and 3.9±0.2 N respectively and all differed significantly (Table 6, FIG. 16). At 200 mm/min, the trend remained as average extrusion forces were 26.4±4.5 N, 10.6±1.6 N, and 6.4±0.5 N respectively with 0% PBS differing significantly from the other two groups. Samples of 6R25 had an average extrusion force of 29.3±4.8 N at 10 mm/min, significantly higher than 4R25 (Table 9). At 50 mm/min and 200 mm/min, the force to extrude the 6R25 was greater than 80 N, causing the test to abort in order prevent damage to the load cell.

The data also illustrate that use of very low concentrations of silk may improve the extrudability of gel relative to higher concentrations as in the case of 2RF25 as compared to 4RF25 and 8RF25. Increasing the concentration of silk in the comminuted silk gels increased the extrusion force required for silk gels at each strain rate, with significant increases between 2RF25 and both 4RF25 and 8RF25 at 10 mm/min and 200 mm/min (Table 9, FIG. 16C). All groups differed significantly at the 50 mm/min strain rate and gels continued to exhibit shear-thickening behavior, seen in the increased extrusion forces associated with increased strain rates. At 10 mm/min 2RF25 and 8RF25 required 0.6±0.0 N and 3.6±0.7 N respectively, at 50 mm/min they required 2.9±0.6 N and 10.1±1.3 N, and at 200 mm/min 7.3±0.6 N and 29.2±2.4 N.

The data further indicated that use of 23RGD to enhance the silk gel material did not appreciably impact the force necessary to extrude silk gel formulations. Adding increasing concentrations of RGD did not have a consistent effect upon the extrusion force necessary for the gel materials (Table 9, FIG. 16D). At a 10 mm/min strain rate there were no significant differences between 4F25 at 3.7±2.0 N, 4R25, 4HR25 at 2.2±0.4 N, and 4VHR25 at 2.8±1.6 N. At a 50 mm/min strain rate 4HR25 was significantly higher than all other extrusion forces at 8.9±1.0 N as compared to 4F25 at 4.5±1.3 N, 4R25, and 4VHR25 at 5.2±1.4N. At a 200 mm/min strain rate 4HR25 at 22.0±0.6 N was significantly higher than only 4VHR25 at 14.6±2.1 N as compared to 4F25 at 22.4±6.7 N and 4R25.

Lastly, the data showed that silk gels blended with saline had very similar extrudability to ZYPLAST™, a material already proven to be readily handled as an injectable material. Based upon this data it is believed that through careful manipulation of the carrier species associated with the silk gel, modulation of silk concentration, and control of particle size, silk gel materials may be made to behave as a readily injectable material.

These results indicate that silk gels may be comminuted to a particle range of about 25-50 µm² in cross-sectional area. Silk gels may be comminuted to a size similar to ZYPLAST™. Silk gel particle size can be decreased by increasing silk concentration or by changing the method of comminution. Increasing concentrations of RGD did not develop a clear trend in silk particle size. Silk gels may be extruded at a relevant strain rate of 50 mm/min at a force comparable to or less than ZYPLAST™. Silk gel extrusion force may be decreased by adding increased quantities of saline carrier or decreased concentrations of silk in the original gel. Changes of comminution method attempted in this study did not substantially affect the amount of force necessary for silk extrusion. Increasing concentrations of RGD did not develop a clear trend in silk gel extrusion force.

Example 12

Silk Gel Precipitates

The silk gel precipitate materials outlined in Table 10 were generated for analysis. Silk solution of the specified concentration was generated using the stock solution of 8% (w/v) aqueous silk and diluting with purified water (Milli-Q purified). 23RGD/ethanol accelerant was prepared by generating a solution of ethanol and purified water, then dissolving the specified 23RGD quantity by vortexing. Silk precipitates were generated by directly adding the specified volume of accelerant solution to that of silk solution in 50 mL centrifuge tubes, shaking once to mix and allowing the mixture to stand for 5 additional seconds before adding about 45 mL purified water to halt the gelation process. This material stood for 24 hours under ambient conditions and was then strained through stainless steel cloth with 150 µm×150 µm pores to recover precipitates. These precipitates were rinsed twice for 24 hours in 50 mL of purified (Milli-Q) water at room conditions, strained a final time and used for evaluation.

TABLE 10

Silk Gel Precipitate Types Generated

| | Initial Silk Solution | | 23RGD/ethanol Accelerant | | | Final | |
| --- | --- | --- | --- | --- | --- | --- | --- |
| | Silk | | | | Accelerant | Precipitate | |
| Group Name | Silk Concentration (mg/mL) | Solution Volume (mL) | Ethanol Concentration (%) | 23RGD Concentration (mg/mL) | Solution Volume (mL) | Final Silk Concentration (mg/mL) | RGD:Silk Molar Ratio |
| BASE | 80 | 1 | 90 | 2.45 | 1 | 40 | 5.0 |
| RHI | 80 | 1 | 90 | 4.90 | 1 | 40 | 10.0 |
| RVLO | 80 | 1 | 90 | 0.49 | 1 | 40 | 1.0 |
| RLO | 80 | 1 | 90 | 1.47 | 1 | 40 | 3.0 |
| SCLO | 80 | 1 | 90 | 2.45 | 1 | 30 | 6.7 |
| SCVLO | 80 | 1 | 90 | 2.45 | 1 | 20 | 10.0 |
| ECLO | 80 | 1 | 80 | 2.45 | 1 | 40 | 5.0 |
| ECVLO | 80 | 1 | 70 | 2.45 | 1 | 40 | 5.0 |
| AVHI | 80 | 0.67 | 90 | 2.45 | 1.33 | 27 | 10.0 |
| AVLO | 80 | 1.33 | 90 | 2.45 | 0.67 | 53 | 2.5 |

Figure 17:
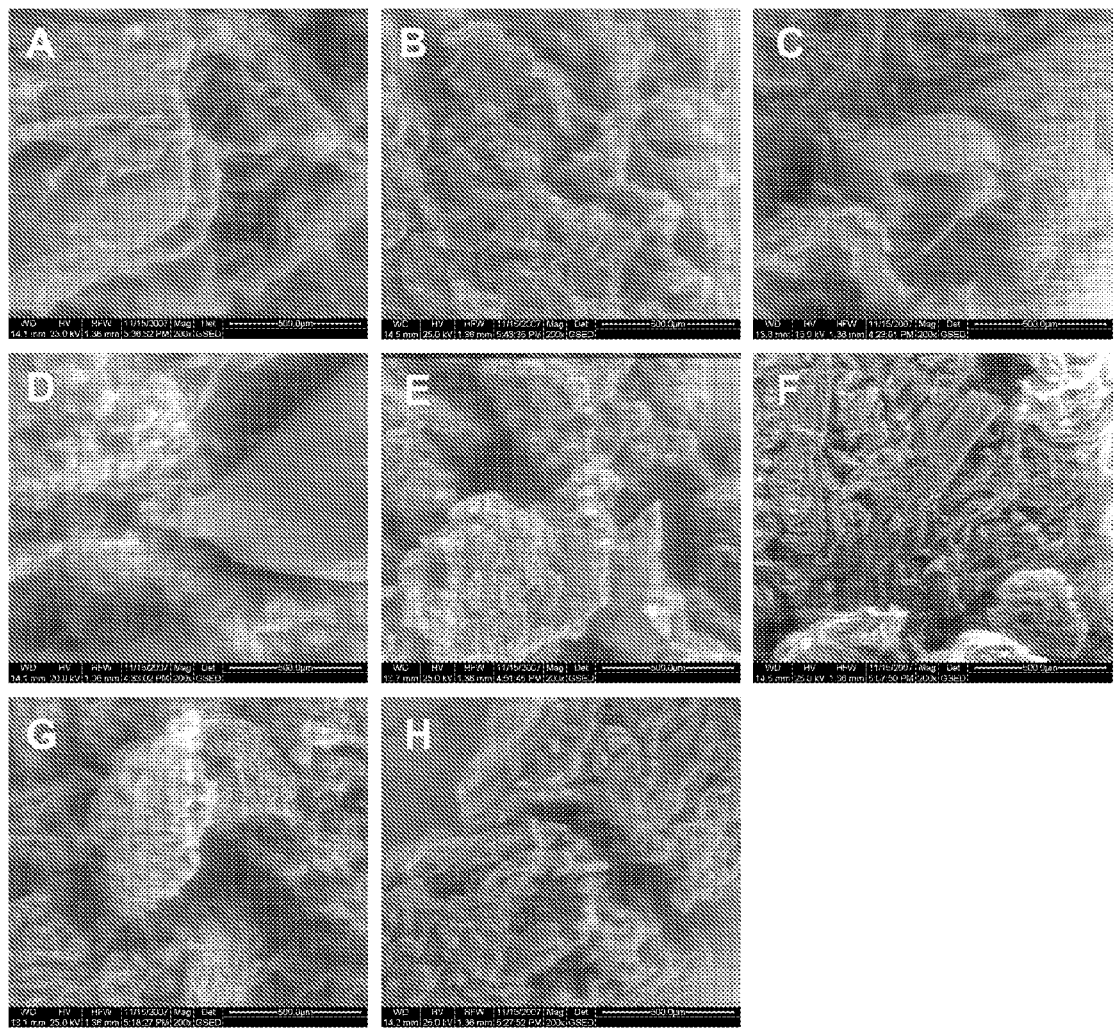
FIG. 17 shows representative ESEM micrographs of selected RGD/ethanol-induced silk precipitates generated from the previously mentioned formulations. BASE (A), SCVLO (B), RHI (C), RLO (D), AVHI (E), ECLO (F), AVLO (G), and 3R 6.7:1 (H) are shown at 200× magnification.

Samples of gel were examined under low-vacuum conditions (~1 Torr) on a Quanta 200 (FEI Co., Hillsboro, Oreg.) environmental scanning electron microscope with images collected at magnifications of 200×. Representative images were taken to illustrate surface topography characteristics of silk precipitate samples (FIG. 17). All silk precipitate types appeared similar under ESEM analysis. Each sample exhibited a mixture of both granular and filamentous regions with occasional appearance of large, contiguous masses of smooth material.

Example 13

Silk Gel Precipitate Massing

Silk precipitate samples, as described in Example 12, were isolated after rinsing by straining through stainless steel wire cloth with a pore size of 104 μm×104 μm and gently blotted with a clean, lint-free wipe. Samples were massed to the nearest 0.01 mg using an S-215 balance (Denver Instrument, Denver, Colo.). These samples were frozen to −80° C. for 24 hours and placed into a Labconco lyophilizer unit (Labconco Corp., Kansas City, Mo.) for 96 hours to remove all water content. The precipitate residual solids were massed again and the dry mass fraction in the samples determined. One-Way analysis of variance (ANOVA) was used to test for significant differences caused by changing silk concentration, 23RGD concentration and accelerant volume. A Student's t-test was used to test the significance of differences resulting from altered ethanol concentrations.

Increasing silk fibroin concentration increased precipitate dry mass with Increasing the percentage of ethanol in the accelerant solution also increased dry mass of the precipitates with ECVLO produced only trace quantities of precipitate (visible, but not recoverable in measurable quantities).

Figure 18:
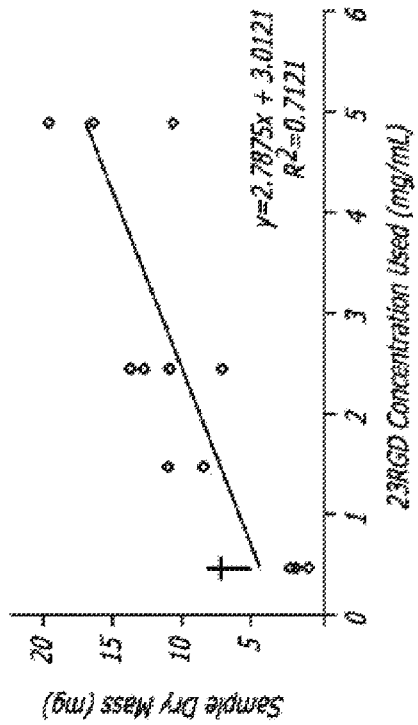
FIG. 18 shows a comparison of the total dry mass of precipitate recovered from each silk precipitate formulation (n=4 for each type) after being subjected to a 96-hour lyophilization process. Data are grouped to compare the effects of changing volume ratio of accelerant added (A), concentration of 23RGD in the accelerant (B), changing the initial silk concentration (C), and changing the concentration of ethanol in the accelerant (D). It was shown that increasing any of these volumes or concentrations resulted in greater quantities of precipitate, though none appear to have substantially greater impact than another. This phenomenon is likely due to basic kinetics of the assembly reaction, with each reagent in turn appearing both as an excess and as limiting dependent upon the specific formulation. *—significant difference, $p<0.05$; †—Group differs significantly from all others.
Figure 18:
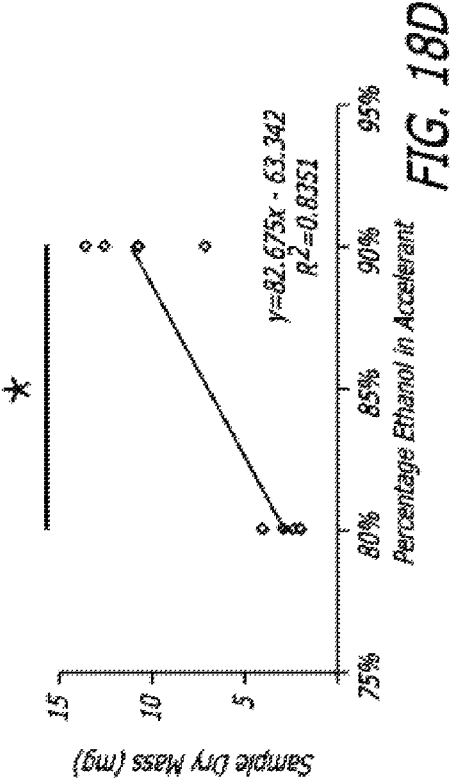
Figure 18:
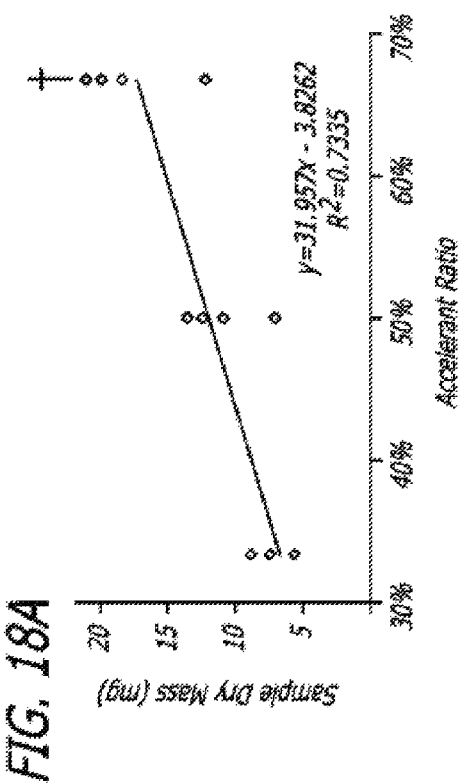
Figure 18:
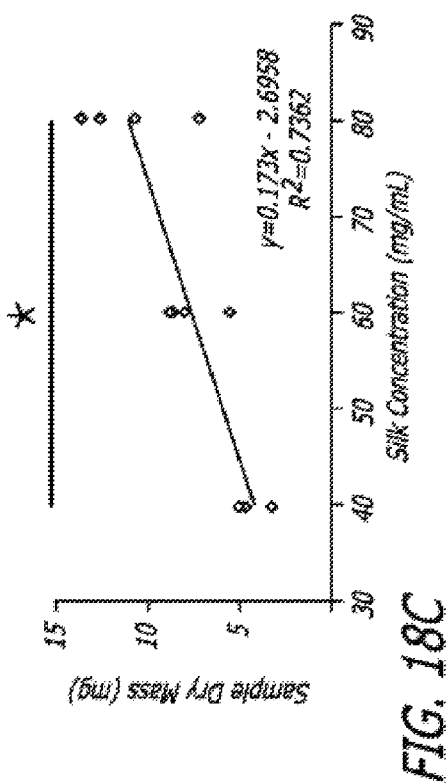

Increasing accelerant volume significantly increased precipitate dry mass as AVHI was significantly greater than both AVLO and BASE ($p \geq 0.05$, FIG. 18A). For example, AVHI (18.02±3.9 mg) was significantly greater than both AVLO (7.37±1.33 mg) and BASE (11.07±2.86 mg). Increasing concentrations of 23RGD in the accelerant also increased the dry mass of precipitate with BASE and RHI both significantly higher than RVLO at (FIG. 18B). Fore example, BASE at 11.07±2.86 mg, RHI at 15.61±3.62 mg, and RMED at 10.2±1.42 mg were all significantly higher than RLO at 1.9±0.6 mg. Increasing silk fibroin concentration increased precipitate dry mass with BASE being greater than SCLO and significantly greater than SCVLO (FIG. 18C). For example, BASE was greater than SCLO at 7.84±1.49 mg and significantly greater than SCVLO at 4.15±1.0 mg. Increasing the percentage of ethanol in the accelerant solution also increased dry mass of the precipitates with BASE producing significantly more than ECLO (FIG. 18D). For example, BASE produced significantly more than ECLO at 2.8±0.91 mg. ECVLO produced only trace quantities of precipitate (visible, but not recoverable in measurable quantities). These results indicate that greater concentrations of reactants (i.e., accelerant solution, RGD, silk and ethanol) all increased the quantity of precipitant resultant.

Figure 19:
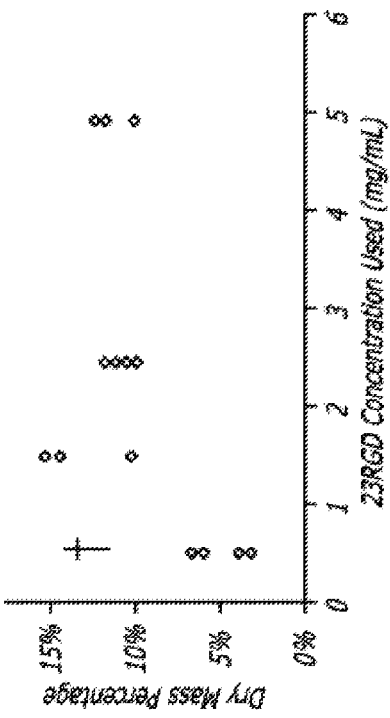
FIG. 19 shows a comparison of the percentage of dry mass in each of precipitate recovered (n=4 for each type) after being subjected to a 96-hour lyophilization process. Data are grouped to compare the effects of changing volume ratio of accelerant added (A), concentration of 23RGD in the accelerant (B), changing the initial silk concentration (C), and changing the concentration of ethanol in the accelerant (D). Increasing the concentration of 23RGD used increased the dry mass percentage of precipitates, while increasing the ethanol percentage in the accelerant decreased dry mass. These changes may stem from formation of altered gel network structures caused by manipulation of these variables, likely more crystalline in the case of 23RGD increases and less crystalline in the case of ethanol concentration increases. *—significant difference, $p<0.05$; †—Group differs significantly from all others.
Figure 19:
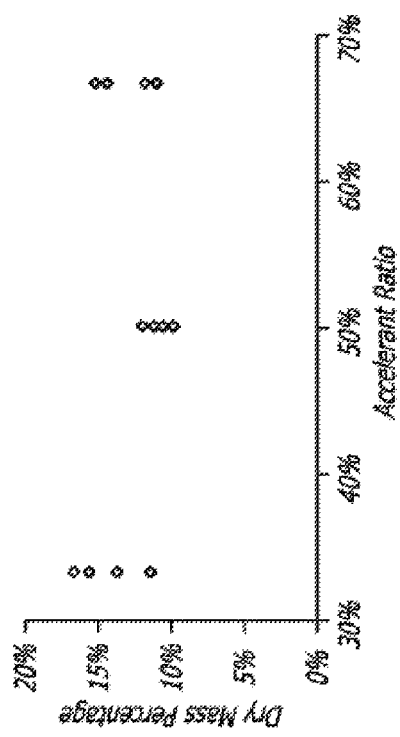
Figure 19:
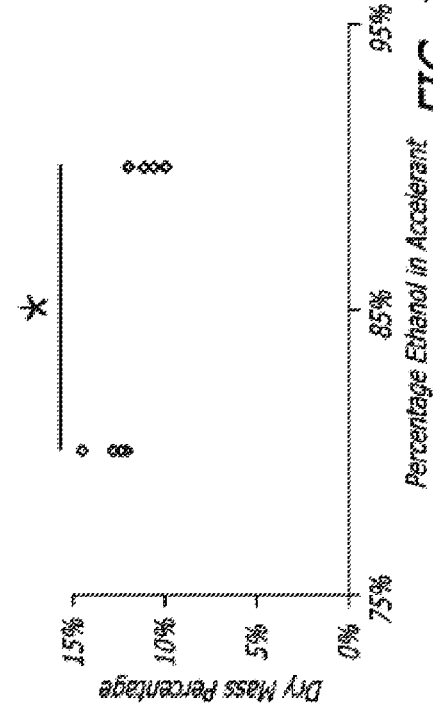
Figure 19:
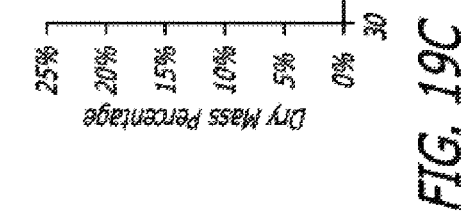

The percent water in silk precipitates was determined as the percentage of mass lost after silk precipitates of each formulation types were subjected to a lyophilization step. Increasing the volumetric fraction of accelerant added to make silk precipitates did not significantly ($p \geq 0.05$) affect the dry mass fraction of the resultant precipitates (FIG. 19A). For example, AVLO at (85.57±2.32%, BASE at 88.99±0.8%, and AVHI was 86.83±1.95%. Increasing concentrations of 23RGD in the accelerant showed a significant increase in dry mass percentage with RVLO significantly less than RLO, RHI, and BASE (FIG. 19B). For example, RLO at 95.01±1.76% retained significantly more water than RMED at 86.52±2.67%, RHI at 88.39±0.98%, and BASE. Increasing concentrations of silk fibroin did not result in a clear trend although SCLO was significantly greater than both SCVLO and BASE (FIG. 19C). For example, SCLO at 80.77±1.97% was significantly less than both SCVLO at 86.94±1.98% and BASE. Increasing the percentage of ethanol in the accelerant solution significantly decreased the dry mass percentage with ECLO compared to BASE (FIG. 19D). For example, ECLO at 86.97±1.16% compared to BASE. In summary, greater concentrations of reactants (i.e., accelerant solution, 23RGD, silk and ethanol) increased the quantity of resultant precipitate. It is also of interest that there were significant differences between the dry mass fractions of BASE and both RVLO and ECLO, possibly indicating different protein structures. These differing protein structures might be more hydrophobic than BASE in the case of ECLO and more hydrophilic in the case of RVLO. These properties might used to affect the stability of the gels in an in vivo environment with more hydrophilic materials being more readily bioresorbed by the host while more hydrophobic materials prove more resistant.

In examining the percent of water in the precipitates it is of particular interest that there were significant differences between BASE and both RLO and ECLO. This may result from structural motifs different than other precipitate types generated by RLO and ECLO. With respect to ECLO, it has a greater proportion of β-sheet structure than BASE and would be expected to entrain less water. However, the difference observed between RLO and base is difficult to explain. RLO has a greater extent of β-sheet structure with less α-helix and random coil motifs than BASE, yet it entrains a greater quantity of water. In fact, this same trend is seen when comparing RLO to RMED, BASE, and RHI. The situation is further confounded in examining the relationship between the initial secondary structures of RMED, BASE and RHI, as all initially exhibit greater quantities of α-helix and random coil than RLO, yet all entrain significantly less water. SCLO samples also had a significantly higher dry mass percentage as compared to BASE and SCVLO sample with no clear trend or reason for this occurrence. These data indicate that there may be a structural difference in these precipitates not apparent in the secondary structure of the materials which is affecting the manner in which the precipitates associate with water. It may be the case that the RGD bound to these precipitates has altered in some fashion the manner in which the silk molecules are presented to water, enhancing their ability to associate with it.

Example 14

Gel Precipitate FTIR Spectrum Capture

Gel precipitates of each type, as described in Example 12, were analyzed by attenuated total reflectance Fourier-transform infrared (ATR-FTIR) spectroscopy using a Bruker Equinox 55 spectrophotometer (Bruker Optics, Inc., Billerica, Mass.) coupled with a Pike MIRACLE™ germanium crystal (PIKE Technologies, Madison, Wis.). Sample ATR signal spectra were obtained by performing a 128-scan integration. Resolution was set to 4 $cm^{-1}$ with a 1 $cm^{-1}$ interval from a range of 4000 to 400 $cm^{-1}$. FTIR spectra of pure water were also collected and subtracted manually from the gel spectra to remove confounding water signal at a ratio conducive to flattening the region between 1800 $cm^{-1}$ and 1700 $cm^{-1}$ on the spectrum. After subtraction, the Amide I bands (1700-1600 $cm^{-1}$) of representative spectra were evaluated against characteristic peaks commonly accepted to be associated with secondary protein structures.

Figure 20:
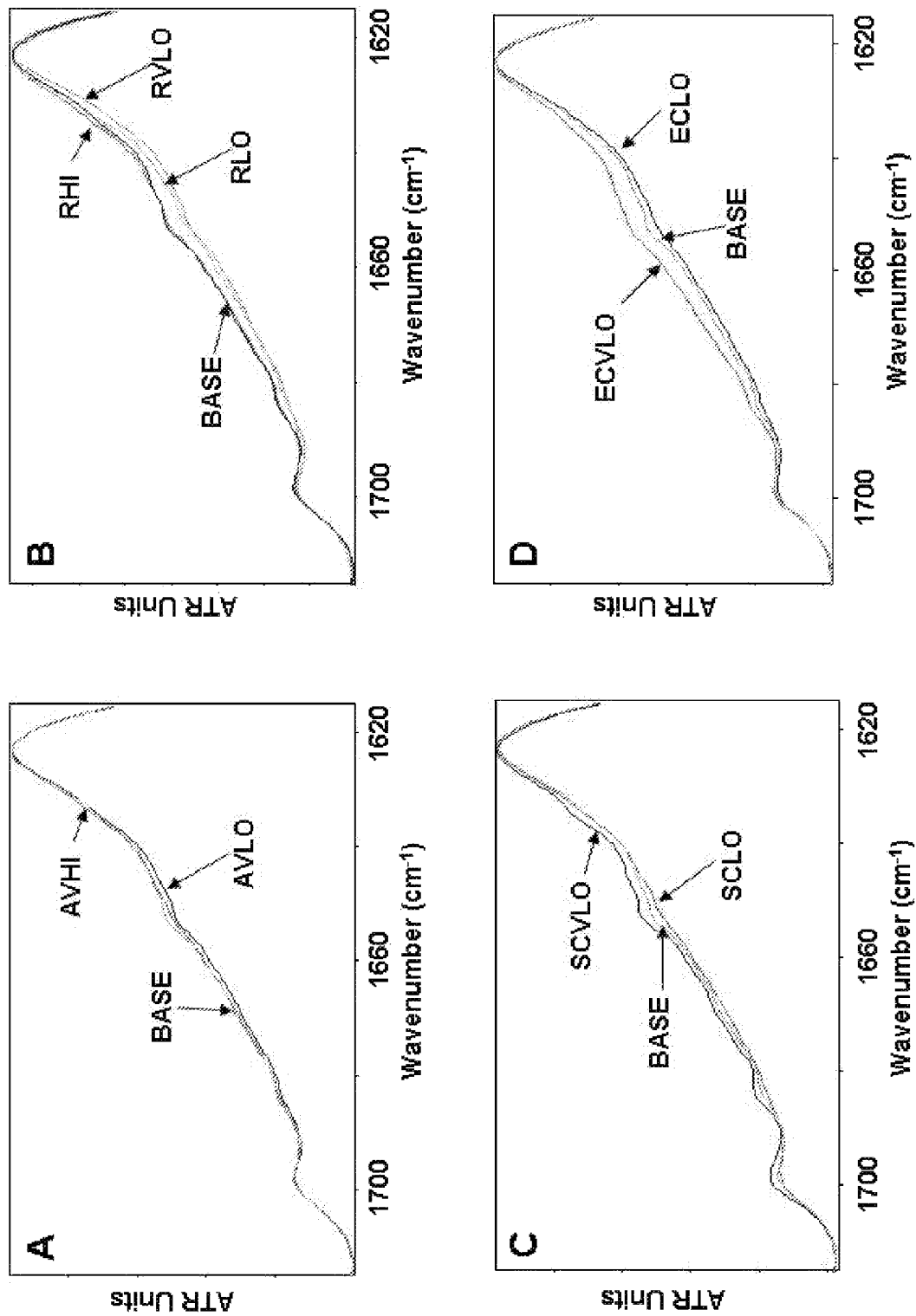
FIG. 20 shows representative FTIR spectra of the Amide I band for 23RGD/ethanol-induced silk precipitates immediately after processing (D0). Spectra are grouped to compare the effects of changing volume ratio of accelerant added (A), concentration of 23RGD in the accelerant (B), changing the initial silk concentration (C), and changing the concentration of ethanol in the accelerant (D). These spectra illustrate that similarities exist between all groups although changing 23RGD concentrations and ethanol concentrations may substantially impact precipitate structure. Increasing concentrations of decreased β-sheet seen in a peak shift from ~1621 $cm^{-1}$ in RVLO to ~1624 $cm^{-1}$ in RLO. A further increase in 23RGD concentration in both BASE and RHI caused this weakened β-sheet again along with increased signal values in the 1654 $cm^{-1}$ and 1645 $cm^{-1}$ range, correlating to increased random coil and α-helical content. An increased percentage of ethanol decreased the content of α-helical and random coil shown by decreased signal between 1670 $cm^{-1}$ and 1630 $cm^{-1}$ in both ECLO and BASE samples relative to ECVLO. This decrease in α-helical and random coil is accompanied by an increase in β-sheet structure. The findings relating to 23RGD and ethanol concentrations reinforce the trends observed in the percent dry mass of the precipitates, supposing that α-helical and random coil motifs entrain more water than β-sheet regions.

Examination of the silk precipitates under FTIR revealed that increasing the volumetric ratio of accelerant added to the silk solution had little effect on their protein secondary structure (FIG. 20A). AVLO, BASE, and AVHI all exhibited similar characteristics with characteristic peaks around 1624 $cm^{-1}$ and a toe region at 1698 $cm^{-1}$ indicating a predominance of β-sheet and β-turn structure respectively. Each sample also exhibited additional structures at 1677 $cm^{-1}$, 1663 $cm^{-1}$, 1654 $cm^{-1}$ and 1645 $cm^{-1}$ denoting additional interspersed β-sheet, β-turn, α-helical and random coil conformations respectively. Increasing concentrations of 23RGD in the accelerant decreased β-sheet stability indicated by a peak shift from ~1621 $cm^{-1}$ in RVLO to ~1624 $cm^{-1}$ in RLO (FIG. 20B). Further increasing the concentration of 23RGD in BASE and RHI caused this weakened β-sheet again accompanied by an increase in higher signal values in the 1654 $cm^{-1}$ and 1645 $cm^{-1}$ ranges, indicating increased random coil and α-helical constituents. Otherwise, RVLO, RLO, BASE, and RHI revealed similar structures with dominant peaks in the 1620 $cm^{-1}$ range and a toe region at 1698 $cm^{-1}$ with additional structures at 1654 $cm^{-1}$ and 1645 $cm^{-1}$. Increasing concentrations of silk fibroin had little perceptible effect on protein secondary structure (FIG. 20C). The spectra for SCVLO, SCLO, and BASE each exhibited similar characteristic peaks around 1624 $cm^{-1}$ with toe regions at 1698 $cm^{-1}$ indicating a predominant β-sheet structure with additional α-helical and random coil conformations interspersed. Increasing the percentage of ethanol in the accelerant solution resulted in less evidence of α-helical and random coil conformations indicated by a decrease in the signal between 1670 $cm^{-1}$ and 1630 $cm^{-1}$ in both ECLO and BASE samples relative to ECVLO (FIG. 20D). This decrease in α-helical and random coil is accompanied by an increase in β-sheet structure.

Substantial similarity existed between all groups except for RVLO and ECVLO, which each differ from BASE formulation. Each of these material types exhibited a different secondary structure from both each other and from BASE, reinforcing the trend observed previously in the percent dry mass of the precipitates. Higher concentrations of 23RGD yielded less organized β-sheet structures and lower concentrations of ethanol yielded greater quantities of α-helix and random coil motifs. It is possible that used in conjunction with one another, these two phenomena could be adjusted to develop silk structures resulting from silk solutions in any of a variety of different protein conformations. These conformations could, in turn, be tailored based upon the desired ultimate bulk properties of the silk material.

It is expected that higher β-sheet components might provide the gel with greater resistance to bioresorption and compressive loading, while at the same time, making the material more rigid.

Example 15

Congo Red Staining of Gel Precipitates

Silk precipitate samples were stained with 100 μM Congo red in purified water. Silk precipitate samples weighing 5-10 mg were vortexed with 500 μL of this solution for 15 seconds, allowed to stand at room temperature (~20-24° C.) for 10 minutes, then centrifuged at 16,000 g (RCF) for 10 minutes. The supernatant was discarded and the pellet re-suspended by vortexing for 30 seconds in 1 mL of purified water. The process of soaking, centrifugation, aspirating and rinsing was repeated 3 times. The final pellet was removed, smeared on a glass microscope slide, and imaged under white and polarized light using a Microscope PC MACROFIRE™ Model S99831 Camera (Optronics, Goleta, Calif.) and PICTUREFRAME™ 2.1 software (Optronics, Goleta, Calif.) and a System Microscope Model BX41 (Olympus, Melville, N.Y.).

Figure 21:
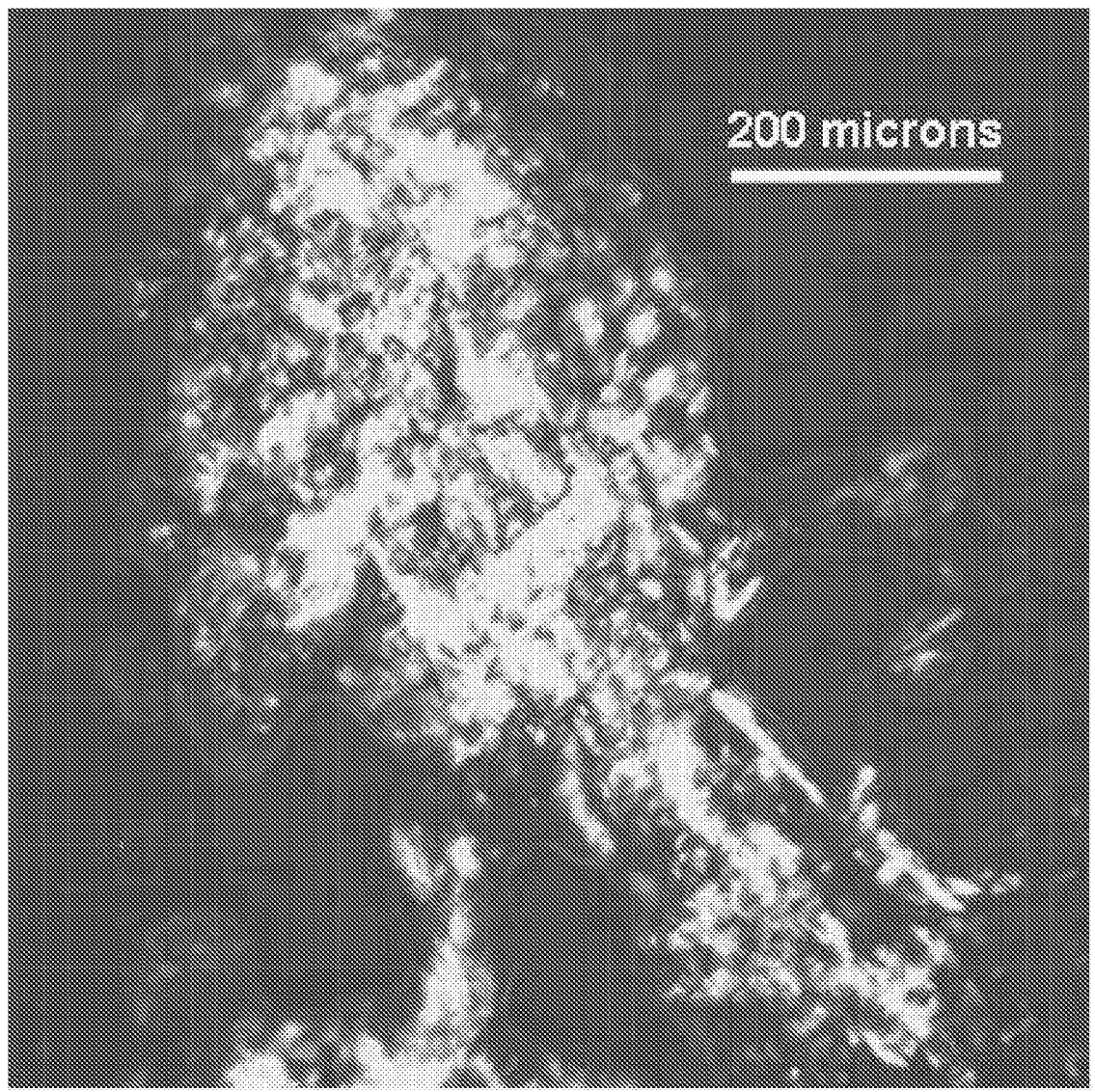
FIG. 21 is a representative micrograph of Congo red-stained 23RGD/ethanol-induced silk precipitates under polarized light at 20× magnification. A lack of emerald-green birefringence indicates a negative result in testing for amyloid fibril formation.

None of the silk precipitate types exhibited the emerald luminescence typically associated with amyloid fibrillar structures (FIG. 21). All precipitate types did exhibit bright white luminescence, indicative of a robust crystalline structure. The extent of this brightness does not appear to vary substantially by formulation, but only by sample quantity on the slide. Based on these results, it is unlikely that any of these precipitate types is amyloid in nature, a positive sign, as amyloid fibrils are associated with a number of negative pathologies in humans.

Example 16

23RGD Quantification in Gel Precipitates by HPLC

The amount of 23RGD bound to silk precipitates was quantified by analyzing lyophilized samples. The 23RGD was removed by incubating the samples for 4 hours in a dissolving buffer, then centrifuging on an Eppendorf 5415C (Eppendorf North America Inc., Westbury, N.Y.) at 16,000 g (RCF) for 30 minutes and the supernatant collected. This supernatant was then centrifuged in identical fashion and the final supernatant collected for HPLC analysis using a PerkinElmer Series 200 (PerkinElmer, Waltham, Mass.). The 23RGD peak areas from each curve were compared against a standard curve. 1-Way ANOVA was used to test for significant differences caused by changing silk concentration, 23RGD concentration, and accelerant volume. A Student's t-test was used to test the significance of differences resulting from altered ethanol concentrations.

Figure 22:
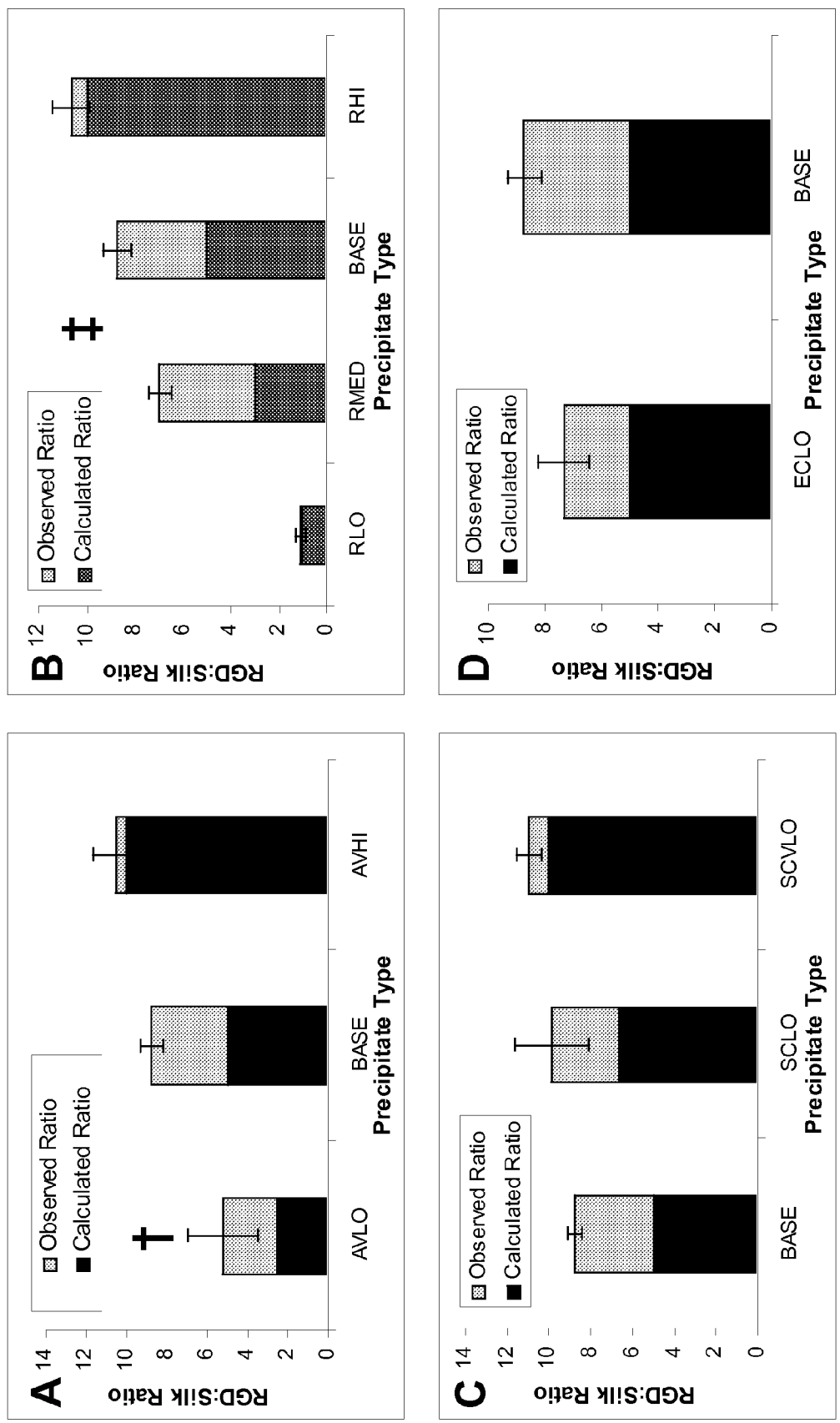
FIG. 22 shows comparison of 23RGD:silk molar ratio in each of precipitate recovered. Data are grouped to compare the effects of changing volume ratio of accelerant added (A), concentration of 23RGD in the accelerant (B), changing the initial silk concentration (C), and changing the concentration of ethanol in the accelerant (D). In examining the 23RGD bound to the precipitates, all materials contained more 23RGD than predicted by initial calculations aside of AVHI, RVLO, RHI, and SCVLO. In the cases of AVHI and ECLO the 23RGD quantity was substantially more than was expected. In the cases of BASE, RLO, SCVLO, and SCLO the 23RGD quantities were approximately double that expected. This may be indicative of the formation of a 23RGD dimer in the 90% ethanol accelerant solution. The RVLO samples were made with a 23RGD concentration of 0.49 mg/mL in the accelerant, the lowest used in this study and potentially within the solubility range of 23RGD in 90% ethanol. RLO samples used 1.47 mg/mL and most other formulations were made with a 23RGD accelerant concentration of 2.45 mg/mL, above the 23RGD concentration at which dimerization became favorable in the solution. Further highlighting the possibility of 23RGD dimerizing in the ethanol solution is the behavior of ECLO precipitation. The 23RGD concentration remains 2.45 mg/mL as with BASE and AVLO but the water concentration in the accelerant is increased to 20% and results in a binding of about 1.5-fold the expected total of 23RGD instead of 2-fold. This may be due to dissolution of a greater quantity of 23RGD, causing coexistence between dimeric and monomeric 23RGD in solution reflected in the subsequent binding ratios. *—significant difference, p<0.05; †—Group differs significantly from all others; ‡—All groups differ significantly.

Increasing the quantity of 23RGD/ethanol accelerant added resulted in a significant increase ($p \geq 0.05$) in 23RGD: silk ratio for both BASE and AVHI as compared to AVLO (FIG. 22A). For example, BASE at 8.7±0.6 and AVHI at 10.5±1.2 were significantly increased as compared to AVLO at 5.2±1.8. Increasing the quantity of 23RGD in the accelerant solution resulted in significant increases in 23RGD:silk ratio for each of RVLO, RLO, BASE, and RHI relative to each other (FIG. 22B). For example, RLO at 1.1±0.2, RMED at 6.95±0.49, BASE and RHI at 10.7±0.8 relative to each other. Changing the starting concentration of silk in solution prior to precipitation did not affect 23RGD:silk ratio as those in SCVLO, SCLO, and BASE did not differ significantly (FIG. 22C). For example, SCVLO at 11.0±0.4, SCLO at 9.9±1.8, and BASE did not differ significantly. Decreasing the ethanol content in the accelerant did not produce a significant effect as observed by comparing ECLO and BASE (FIG. 22D).

Reviewing this data in light of the precipitate dry massing data, none of the conditions explored resulted in isolation of silk (~10-35% precipitated) nor 23RGD (~5-30% precipitated) as limiting reagents in the reaction. Precipitate samples generated at a calculated 10:1 23RGD:silk ratio consistently generated a "correct" molecular binding ratio. In the case of AVHI, this runs contrary to the trend of bound 23RGD concentrations being approximately double the projected values as indicated by AVLO and BASE (about 5:1 and about 9:1, respectively). This might be explained by saturation of the silk with 23RGD in the case of 10:1 23RGD precipitates. This is further reinforced by the behavior of SCVLO and 0.6S 3R 10:1, both of which were produced using 2.45 mg/mL 23RGD in 90% ethanol as the AVHI was. Both materials projected to have greater than 10:1 ratios of bound 23RGD (20:1 and 13.4:1, respectively) based on the behavior of AVLO and BASE, but which both reached only about 10:1 ratios. RHI, generated using a 4.5 mg/mL 23RGD concentration in the accelerant which conceivably should have been high enough to induce the postulated dimeric 23RGD reached only the expected 23RGD ratio of about 10:1 not the postulated 20:1.

Figure 23:
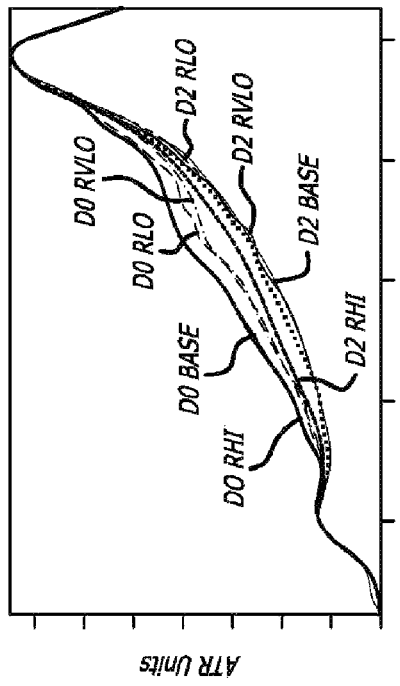
FIG. 23 shows a representative FTIR spectra of the Amide I band are shown for 23RGD/ethanol-induced silk precipitates initially (D0) and after proteolytic bioresorption (D2). Spectra are grouped to compare the effects of changing volume ratio of accelerant added (A), concentration of 23RGD in the accelerant (B), changing the initial silk concentration (C), and changing the concentration of ethanol in the accelerant (D). Accelerant quantity added did not substantially affect the bioresorption behavior of the materials as BASE, AVHI and AVLO all featured decreased levels of α-helix and random coil motifs. This decrease was slightly larger in the case of AVLO which also featured a peak shift from 1624 cm$^{-1}$ to 1622 cm$^{-1}$, indicating a more stable β-sheet structure. 23RGD concentration did not appear to affect bioresorption behavior of the materials either as RVLO, RLO, BASE and RHI all showed decreased in α-helix and random coil motifs, though a greater portion of α-helix and random coil remained intact in RHI. Silk concentration did not substantially affect the bioresorption behavior of the materials as BASE and SCLO exhibited decreased levels of α-helix and random coil motifs and featured slight peak shifts from 1624 cm$^{-1}$ to 1623 cm$^{-1}$.
Figure 23:
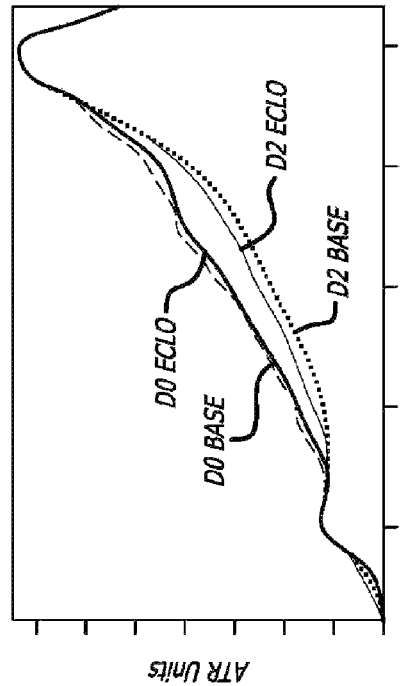
Figure 23:
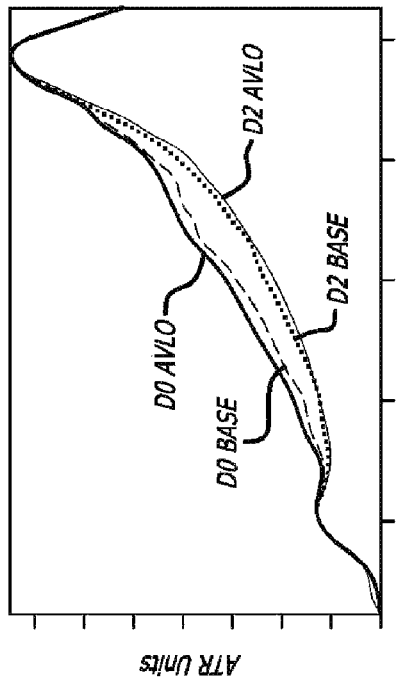
Figure 23:
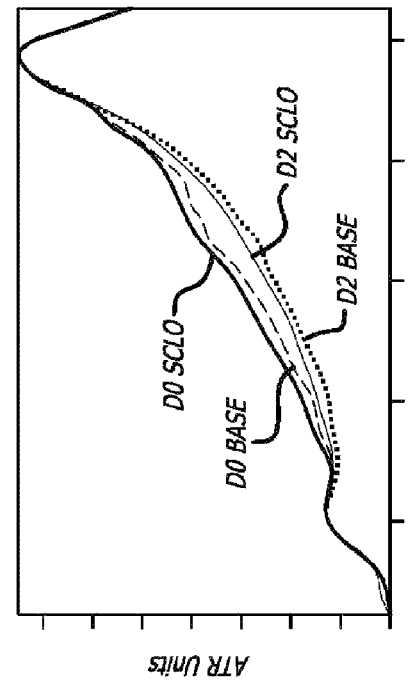

Few of the silk precipitates entrained a molar ratio similar to what was initially calculated (FIG. 23). Four groups, SCVLO, AVHI, RHI, and RLO contained ratios similar to their calculated values of RGD per mole of silk. The six remaining groups contained ratios substantially greater than their calculated values. In the cases of AVLO, BASE, RMED, and SCLO, the RGD quantities were about 2-fold greater than expected. Although not wishing to be limited by theory, this greater observed molar ratio may be indicative of the formation of a RGD bi-layer. It may be the case that either micelles or lamellar structures of RGD existed in the 90% ethanol solution prior to addition to the silk, upon contacting the aqueous phase, micellar stability was disrupted. As a result, a bi-layer of RGD was formed at the solution interface, where these molecules began to interact with the silk molecules. The RLO samples were made with a RGD concentration of 0.49 mg/mL in the accelerant, the lowest used in this study and potentially within the solubility range of RGD in 90% ethanol. RMED samples used 1.47 mg/mL and most other formulations were made with a RGD accelerant concentration of 2.45 mg/mL, above the RGD concentration at which dimerization became favorable in the solution. Further highlighting the possibility of RGD dimerizing in the ethanol solution is the behavior of ECLO precipitation. The RGD concentration remains 2.45 mg/mL as with BASE and AVLO but the water concentration in the accelerant is increased to 20% and results in a binding of about 1.5-fold the expected total of RGD. This may be due to a decreased driving force for RGD bi-layer formation at the solution interface caused by the lower ethanol content. This might in turn cause disruption to fewer micellar structures in the initial accelerant solution. It could also be explained by altered micellar structure, varying between a single peptide layer and a multi-lamellar structure depending upon the concentrations of water and ethanol in the accelerant phase.

Precipitate samples generated at a calculated 10:1 RGD: silk ratio consistently generated a "correct" molecular binding ratio. In the case of AVHI, this runs contrary to the trend of bound RGD concentrations being approximately double the projected values as indicated by AVLO and BASE (about 5:1 and about 9:1 respectively). It is possible that this might be explained by saturation of the silk with RGD in the case of 10:1 RGD precipitates. This is further reinforced by the behavior of SCVLO and 0.6S 3R 10:1, both of which were produced using 2.45 mg/mL RGD in 90% ethanol as was AVHI. Both materials projected to have greater than 10:1 ratios of bound RGD (20:1 and 13.4:1 respectively) based on the behavior of AVLO and BASE, but which both reached only about 10:1 ratios. RHI, generated using a 4.5 mg/mL RGD concentration in the accelerant which conceivably should have been high enough to induce the postulated dimeric RGD, reached only the expected RGD ratio of about 10:1 not the postulated 20:1. This may be attributed to the mode of binding between the silk molecules and the RGD molecules. It is expected that RGD will bind through a hydrophobic association mechanism and despite the largely hydrophobic sequence of silk, it may be possible that there are approximately 5 sites which offer preferable RGD binding stability. This presumption stems from the apparent saturation at 10:1 RGD molecules per molecule of silk. Dependent upon the nature of RGD self-association at the solution boundary, it may be a case where single RGD molecules or RGD dimers bind to these sites.

There are a series of properties further indicating the possibility of a specific molecular assembly interaction between the silk and 23RGD accelerant. Conspicuously, that 23RGD does localize to the precipitates in a greater-than-calculated ratio but that it binds at intuitive concentrations which can be related quickly to the initially calculated molar ratios. The fact that this occurs without fully depleting either the 23RGD or the silk fibroin molecules is of further interest. The FTIR data also indicated that use of 0.49 mg/mL 23RGD in RVLO precipitates induced formation of distinctly different structures than use of 2.45 mg/mL in BASE or 4.9 mg/mL in RHI which appeared similar to each other. RMED precipitates generated with 1.47 mg/mL of 23RGD contained characteristics of both RVLO and BASE/RHI material spectra. FTIR indicated a different structure from a 2.45 mg/mL of 23RGD in 70% ethanol accelerant in the case of ECVLO. These outcomes were both reinforced in examining the percentage of dry mass from the resultant precipitates (though ECLO is used to illustrate the trend in 23RGD solubility in ethanol solution instead of ECVLO). Both of these assays indicate the formation of different precipitate structures based upon the extent of 23RGD saturation in the ethanol solution, conceivably resulting from dimeric 23RGD binding or monomeric 23RGD binding.

This phenomenon likely results from the amphiphilic nature of 23RGD and the varied chemistry of the solution phase between heavily ethanolic and heavily aqueous. It is possible that the hydrophilic ends of two 23RGD molecules associate in the 90% ethanol solution, exposing the two hydrophobic ends to solution. Addition of this accelerant solution with dimeric 23RGD causes rapid association of the exposed hydrophobic ends of the 23RGD with hydrophobic domains of the silk molecules, rapidly precipitating them. This process occurs until the 90% ethanol accelerant solution is sufficiently diluted with the aqueous silk solution to cause the dimeric assembly of the 23RGD molecules to no longer be favorable, as a result stopping precipitation. Based upon the apparent saturation at about 10 for 23RGD:silk ratio, there may also be a maximum of 5 binding sites for the 23RGD dimer per molecule of silk. This knowledge may be used to bind specific quantities of 23RGD to silk, while at the same time dictating silk gel structure and resultant behavior. Additionally, this method may also potentially be applied to other amphiphilic peptides of interest during their integration into a silk gel material.

These results indicate that silk precipitate quantity may be increased by increasing the quantity of any reactant in the RGDEEG system. Silk precipitates occurring during RGDEEG gelation are unlikely to be amyloid. Silk precipitate β-sheet structure may be increased by higher concentrations of ethanol accelerant or lower concentrations of RGD. RGD molecules may self-associate into micelles, lamellar structures, or dimers when placed into a strongly ethanolic solution, in turn, assembling with silk in a dimeric fashion during RGDEEG gelation. Silk molecules may become saturated with RGD once they have bound about 10 molecules. Silk precipitate structures may be altered by changing RGD concentrations added, though the extent and nature of these changes remains unclear, as they are not perceptible in material secondary structure. These altered structures may account for otherwise unexplained increased appearance of α-helix and random coil motifs at high RGD concentrations in precipitates. These altered structures may account for otherwise unexplained increased resistance to proteolytic bioresorption of α-helix and random coil motifs at high RGD concentrations in precipitates Example 17

Enzymatic Bioresorption of Gel Precipitates

A single sample of precipitate types selected for distinctly different behaviors from BASE in the previously listed assays including RVLO, RLO, BASE, RHI, ECLO, 0.6S 3R 5:1 weighing approximately 60 mg were massed using an S-215 balance. These samples were placed in a solution of Protease Type XIV from *Streptomyces griseus* (Sigma catalog no. P-5147) in phosphate buffered saline (PBS) was generated at a concentration of 0.3 mg/mL (activity was 4.5 U/mg) at a ratio of 1 mL of protease solution per 100 mg of silk precipitate. The gel and protease solution were incubated for 24 hours at 37° C. with no mechanical mixing. After 24 hours, the residual precipitate was isolated by straining through stainless steel cloth as before and the specimens analyzed by FTIR as described.

Accelerant quantity added did not substantially affect the bioresorption behavior of the materials as BASE, AVHI and AVLO all featured decreased levels of α-helix and random coil motifs (FIG. 23A). This decrease was slightly larger in the case of AVLO which also featured a peak shift from 1624 $cm^{-1}$ to 1622 $cm^{-1}$, indicating a more stable β-sheet structure. The 23RGD concentration did not appear to affect bioresorption behavior of the materials either as RVLO, RLO, BASE and RHI all showed decreased in α-helix and random coil motifs, though a greater portion of α-helix and random coil remained intact in RHI (FIG. 23B). However, a greater portion of α-helix and random coil remained intact in RHI at Day 2 relative to the other samples. Silk concentration did not substantially affect the bioresorption behavior of the materials as BASE and SCLO exhibited decreased levels of α-helix and random coil motifs and featured slight peak shifts from 1624 $cm^{-1}$ to 1623 $cm^{-1}$ (FIG. 23C).

Despite differences in initial structures, all precipitate types bioresorbed in a similar fashion with α-helix and random coil motifs degraded preferentially to β-sheet. Only increasing the concentration of 23RGD, as in the case of RHI, appeared to have any appreciable effect on the final secondary structure of the precipitates. This appears to be a case where there is simply more α-helix and random coil structure upon initial formation of these materials and they take more time to degrade to a similar extent of β-sheet structure as the other formulations. Use of this knowledge in conjunction with an ability to manipulate the secondary protein structures of these materials could lead to biomaterials with very specific lifetimes in vivo.

The invention claimed is:

1. A method of breast reconstruction or augmentation, the method comprising the steps of
   a) implanting a silicone or saline filled breast implant into a site of breast tissue of an individual; and
   b) implanting a hydrogel scaffold at the site of implantation, the hydrogel scaffold comprising a substantially sericin-depleted silk fibroin and adipose cells, the hydrogel scaffold formed by:
      extracting sericin from a silk fibroin thereby forming the substantially sericin-depleated silk fibroin;
      digesting a mixture including the substantially sericin-depleated silk fibroin, thereby forming a digested mixture;
      collecting a supernatant of the digested mixture after centrifugation, wherein the supernatant comprises depolymerized silk fibroin;
      gelling the supernatant in an ethanol solution comprising ethanol as a gelation enhancer and porogens, thereby forming a silk fibroin hydrogel;
      removing the porogens from the silk fibroin hydrogel to form the hydrogel scaffold defined by an array of interconnected pores; and
      seeding the hydrogel scaffold with adipose cells,
   wherein the adipose cells are autologous with the individual.

2. The method of claim 1, wherein the hydrogel scaffold is implanted so as to support a lower pole position of the breast implant.

3. The method of claim 1, wherein the method further comprising the step of at least partially covering the breast implant with the hydrogel scaffold prior to the steps of implanting.

4. A method of breast reconstruction or augmentation, the method comprising the steps of
   (a) implanting a silicone or saline filled breast implant into an individual, and;
   (b) implanting a hydrogel scaffold at the site of implantation, the hydrogel scaffold comprising a substantially sericin-depleted silk fibroin and adipose cells autologous to the individual, the hydrogel scaffold formed by:
      (i) extracting sericin from a silk fibroin thereby forming the substantially sericin-depleated silk fibroin;
      (ii) digesting a mixture including the substantially sericin-depleated silk fibroin, thereby forming a digested mixture, wherein the digested mixture comprises depolymerized silk fibroin;
      (iii) gelling the depolymerized silk fibroin in an ethanol solution thereby forming a silk fibroin hydrogel, and;
      (iv) seeding the silk fibroin hydrogel with adipose cells autologous to the individual.

* * * * *

UNITED STATES PATENT AND TRADEMARK OFFICE
CERTIFICATE OF CORRECTION

PATENT NO. : 8,420,077 B2
APPLICATION NO. : 12/764033
DATED : April 16, 2013
INVENTOR(S) : Gregory H. Altman et al.

Page 1 of 2

It is certified that error appears in the above-identified patent and that said Letters Patent is hereby corrected as shown below:

On the Title page, in item (75), under "Inventors", in column 1, line 3, delete "Westminister," and insert -- Westminster, --, therefor.

On the Title page, in item (56), under "Other Publications", in column 2, line 9, delete "Plypeptide" and insert -- Polypeptide --, therefor.

On Title page 2, in column 1, under "Other Publications", line 5, delete "Biomatericals" and insert -- Biomaterials --, therefor.

On Title page 2, in column 1, under "Other Publications", line 6, delete "Biomatericals," and insert -- Biomaterials, --, therefor.

On Title page 2, in column 2, under "Other Publications", line 17, delete "Evalution" and insert -- Evaluation --, therefor.

On Title page 2, in column 2, under "Other Publications", line 71, delete "biologcal" and insert -- biological --, therefor.

On Title page 3, in column 1, under "Other Publications", line 7, delete "Interatcion" and insert -- Interaction --, therefor.

In the Specification:
In column 4, line 22, delete "lidocane." and insert -- lidocaine. --, therefor.
In column 10, line 27, delete "Saturnidae," and insert -- Saturniidae, --, therefor.
In column 32, lines 15-16, delete "Cholamidopropyhdimethylammonio" and insert -- Cholamidopropyl)dimethylammonio --, therefor.
In column 32, line 36, delete "Cholamidopropyhdimethylammonio" and insert -- Cholamidopropyl)dimethylammonio --, therefor.
In column 35, line 34, delete "specifciation." and insert -- specification. --, therefor.

Signed and Sealed this
Twenty-first Day of October, 2014

Michelle K. Lee
*Deputy Director of the United States Patent and Trademark Office*

In column 36, line 32, after "space" delete "fillers". (Second Occurrence)

In column 41, line 9, delete "of" and insert -- soft --, therefor.

In column 46, line 62, delete "protelolytic" and insert -- proteolytic --, therefor.

In column 47, line 14, delete "flourescence" and insert -- fluorescence --, therefor.

In column 50, line 5, delete "lidocane" and insert -- lidocaine --, therefor.

In column 51, line 58, delete "form" and insert -- from --, therefor.

In column 53, line 54, delete "pyridydithio" and insert -- pyridyldithio --, therefor.

In column 54, line 13, delete "dinitrobenezene" and insert -- dinitrobenzene --, therefor.

In column 54, line 14, delete "1ethyl" and insert -- 1-ethyl --, therefor.

In column 63, line 15, delete "cm-1" and insert -- $cm^{-1}$ --, therefor.

In column 63, line 16, delete "cm-1" and insert -- $cm^{-1}$ --, therefor.

In column 73, line 25, delete "(p≥0.05)" and insert -- (p≤0.05) --, therefor.

In column 73, line 42, delete "(p≥0.05)" and insert -- (p≤0.05) --, therefor.

In column 75, line 59, delete "(p≥0.05," and insert -- (p≤0.05, --, therefor.

In column 75, line 64, delete "Fore" and insert -- For --, therefor.

In column 76, line 39, delete "(p≥0.05)" and insert -- (p≤0.05) --, therefor.

In column 79, line 15, delete "(p≥0.05)" and insert -- (p≤0.05) --, therefor.

In column 81, line 48, delete "precipitates" and insert -- precipitates. --, therefor.

In the Claims:

In column 93, line 27, in claim 1, delete "depleated" and insert -- depleted --, therefor.

In column 93, line 29, in claim 1, delete "depleated" and insert -- depleted --, therefor.

In column 94, line 33, in claim 4, delete "depleated" and insert -- depleted --, therefor.

In column 94, line 35, in claim 4, delete "depleated" and insert -- depleted --, therefor.